(12) United States Patent
Sandvang et al.

(10) Patent No.: US 10,959,942 B2
(45) Date of Patent: Mar. 30, 2021

(54) ANIMAL FEED COMPOSITIONS AND USES THEREOF

(71) Applicants: Novozymes A/S, Bagsvaerd (DK); DSM IP Assets B.V., Heerlen (NL)

(72) Inventors: Dorthe Hoej Sandvang, Slangerup (DK); Esben Gad, Lyngby (DK); Nicholas Michael Kelly, Bagsvaerd (DK); Mikkel Klausen, Copenhagen (DK); Juliane Charlotte Gregaard Thoegersen, Vedbaek (DK); Peter Bjarke Olsen, Copenhagen (DK); Preben Nielsen, Horsholm (DK); Marianne Thorup Cohn, Copenhagen (DK)

( * ) Notice: Subject to any disclaimer, the term of this patent is extended or adjusted under 35 U.S.C. 154(b) by 123 days.

(21) Appl. No.: 15/580,081

(22) PCT Filed: Jul. 4, 2016

(86) PCT No.: PCT/EP2016/065682
§ 371 (c)(1),
(2) Date: Dec. 6, 2017

(87) PCT Pub. No.: WO2017/001701
PCT Pub. Date: Jan. 5, 2017

(65) Prior Publication Data
US 2018/0296475 A1    Oct. 18, 2018

(30) Foreign Application Priority Data
Jul. 2, 2015  (EP) .................................. 15174931

(51) Int. Cl.
| | | |
|---|---|---|
| *A61K 9/00* | (2006.01) | |
| *A23K 20/189* | (2016.01) | |
| *A61K 38/46* | (2006.01) | |
| *A61K 38/47* | (2006.01) | |
| *A23K 50/75* | (2016.01) | |
| *A61P 1/14* | (2006.01) | |
| *A61K 9/16* | (2006.01) | |
| *C12N 9/16* | (2006.01) | |
| *C12N 9/36* | (2006.01) | |

(52) U.S. Cl.
CPC .......... *A61K 9/0056* (2013.01); *A23K 20/189* (2016.05); *A23K 50/75* (2016.05); *A61K 9/0053* (2013.01); *A61K 9/16* (2013.01); *A61K 38/465* (2013.01); *A61K 38/47* (2013.01); *A61P 1/14* (2018.01); *C12N 9/16* (2013.01); *C12N 9/2462* (2013.01); *C12Y 301/03026* (2013.01); *C12Y 302/01017* (2013.01)

(58) Field of Classification Search
None
See application file for complete search history.

(56) References Cited

U.S. PATENT DOCUMENTS

| | | | | |
|---|---|---|---|---|
| 8,445,250 B2 * | 5/2013 | Isaksen | ................ | C12N 9/16 435/195 |
| 8,460,656 B2 * | 6/2013 | De Maria | ................ | C12N 9/16 424/94.65 |
| 9,663,775 B2 * | 5/2017 | Schnorr | ................ | C12N 9/2462 |
| 10,119,130 B2 * | 11/2018 | Schnorr | ................ | C12N 9/2462 |

FOREIGN PATENT DOCUMENTS

| | | |
|---|---|---|
| CN | 103652476 | 3/2014 |
| WO | 00/21381 A1 | 4/2000 |
| WO | 2005/080559 A1 | 9/2005 |
| WO | 2008/097619 A2 | 8/2008 |
| WO | 2011/104339 A1 | 9/2011 |
| WO | 2013/076253 A1 | 5/2013 |

OTHER PUBLICATIONS

Masschalck et al., Journal of Food Protection, vol. 65, No. 12, pp. 1916-1923 (2002).
Selle et al., Anim Feed Science and Technology, vol. 135, pp. 1-41 (2007).
Selle et al., Livestock Science, vol. 113, pp. 99-122 (2008).
Torok et al., Applied and Environmental Microbiology, vol. 77, No. 17, pp. 5868-5878 (2011).
Santos et al., Feed Additives, vol. 13, pp. 38-40 (2013).

* cited by examiner

Primary Examiner — Anand U Desai
(74) Attorney, Agent, or Firm — Elias Lambiris

(57) ABSTRACT

The present invention relates to animal feed compositions comprising polypeptides having lysozyme activity and polypeptides having phytase activity and uses thereof.

Figure 1:
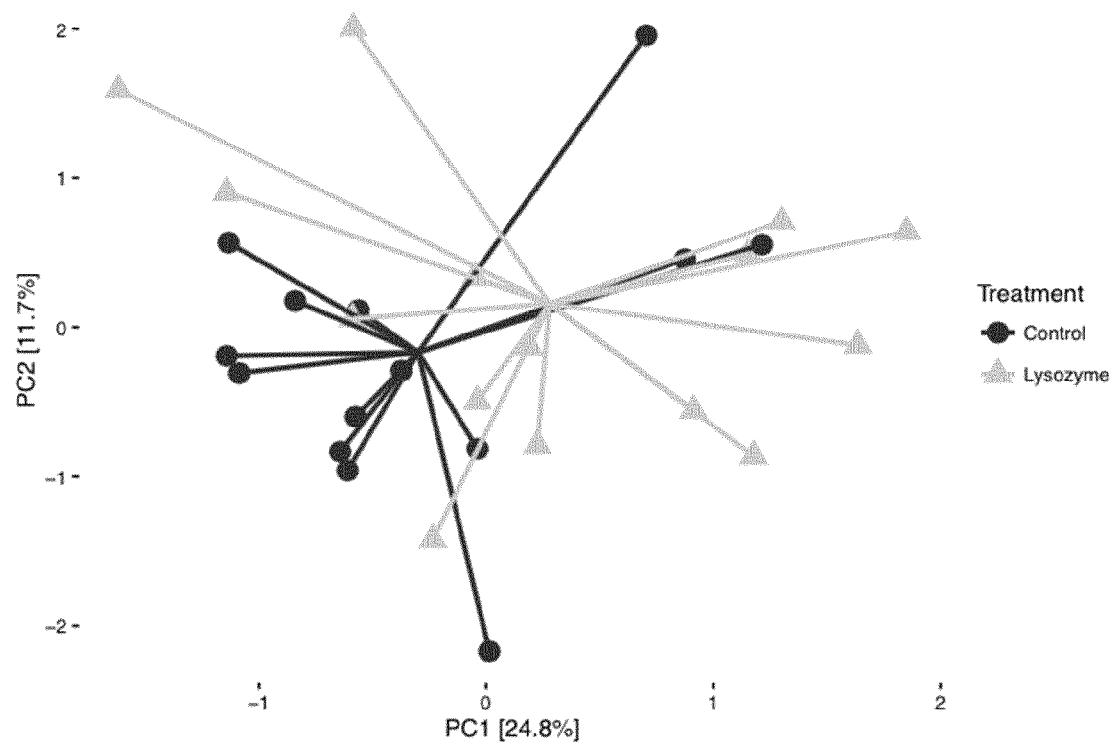
Figure 2:
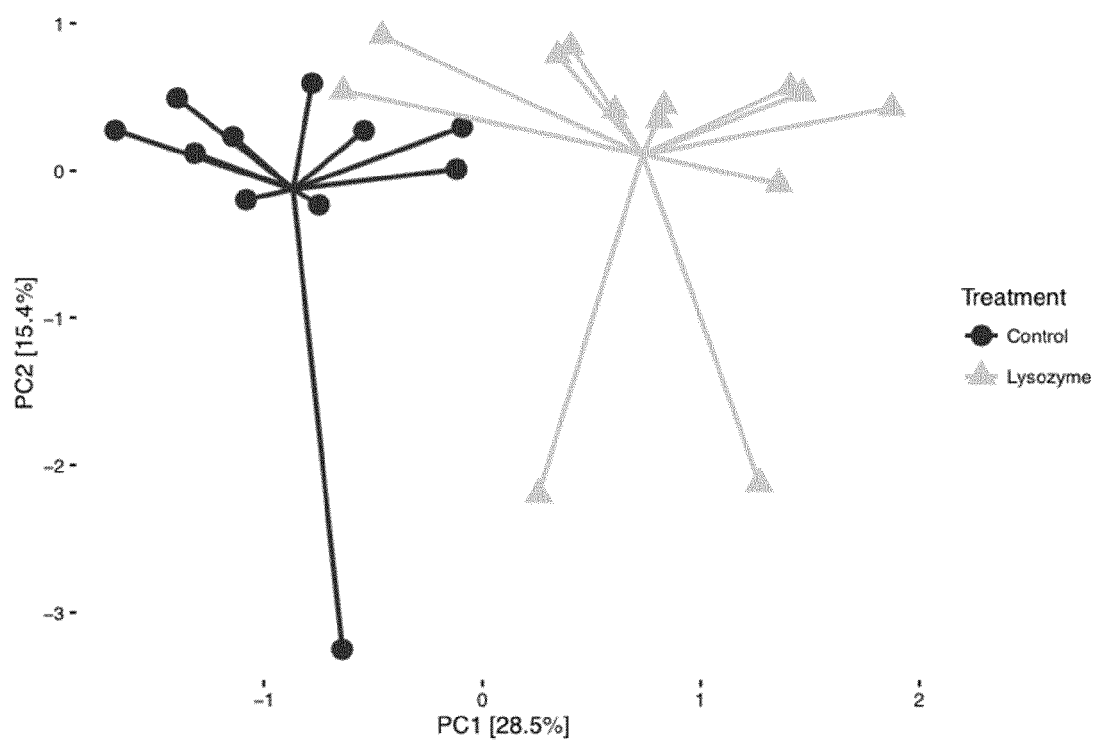
Figure 3:
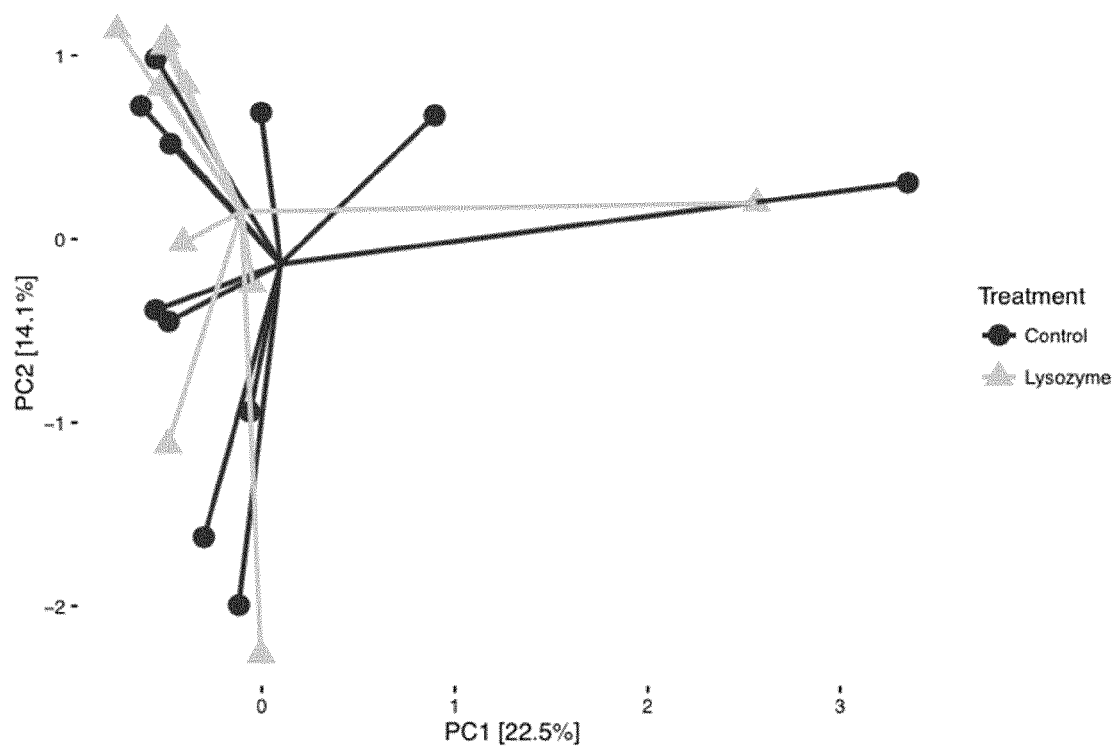
Figure 4A:
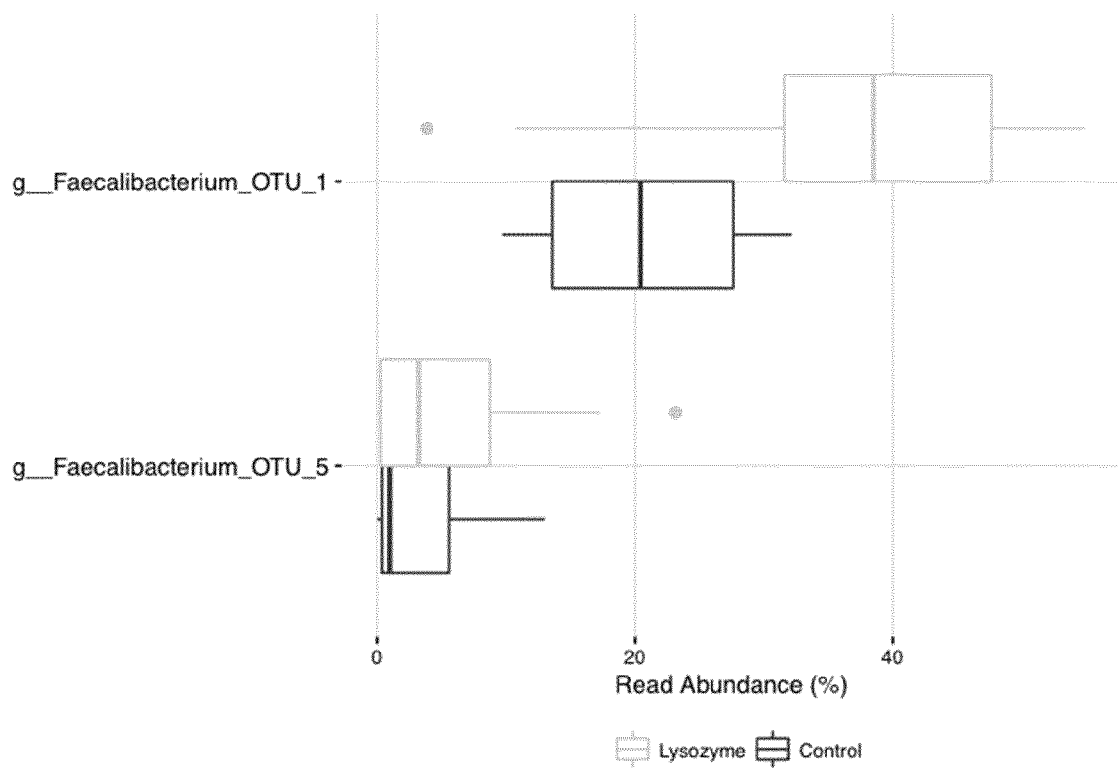
Figure 4B:
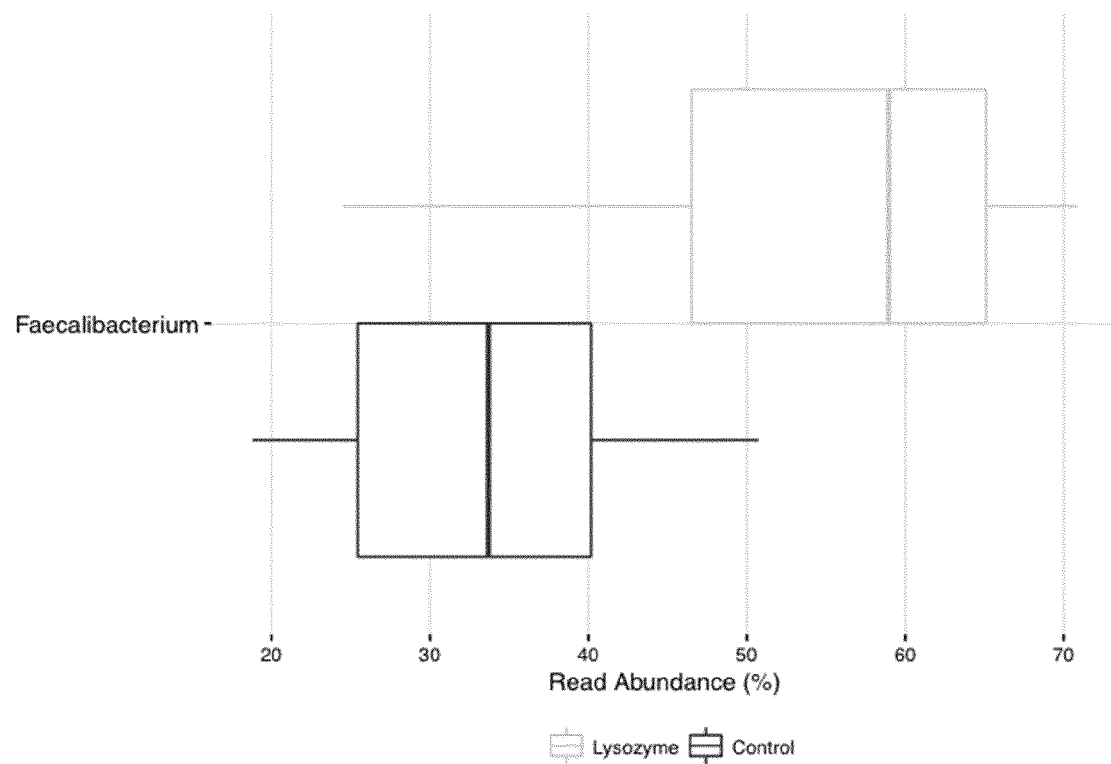
Figure 4C:
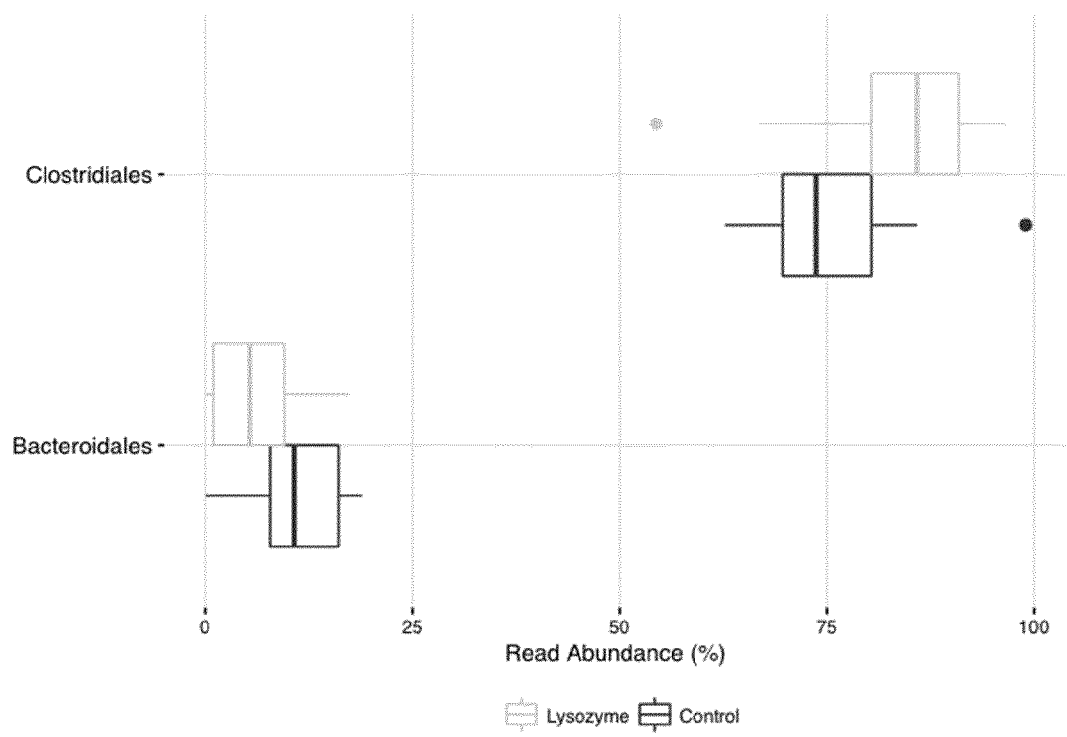
Figure 5A:
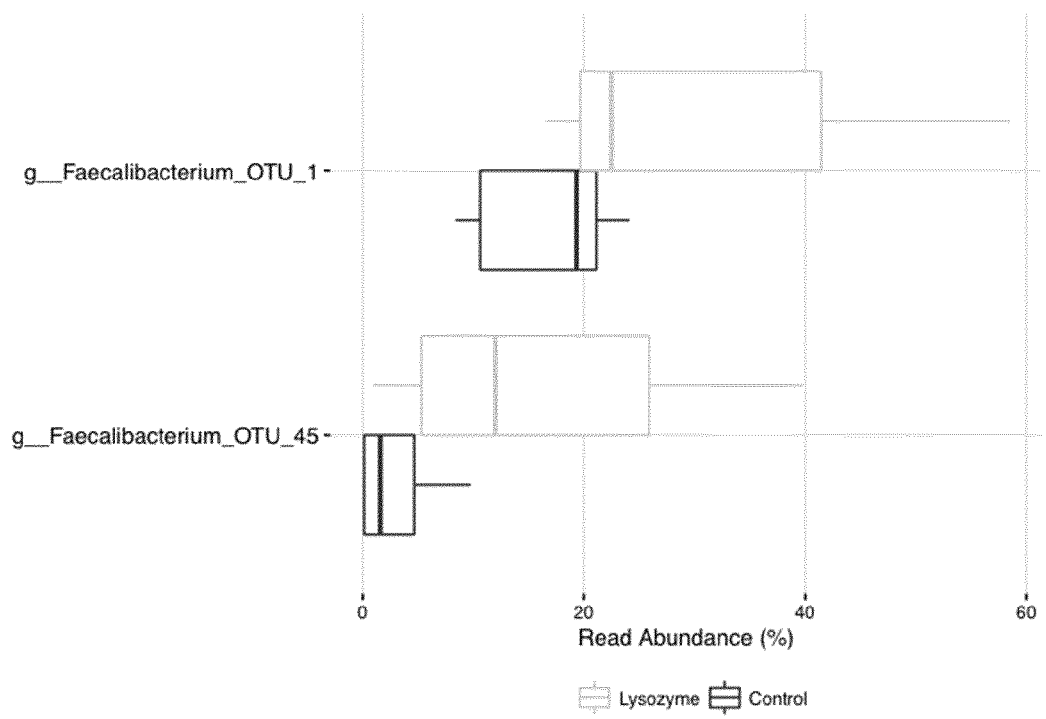
Figure 5B:
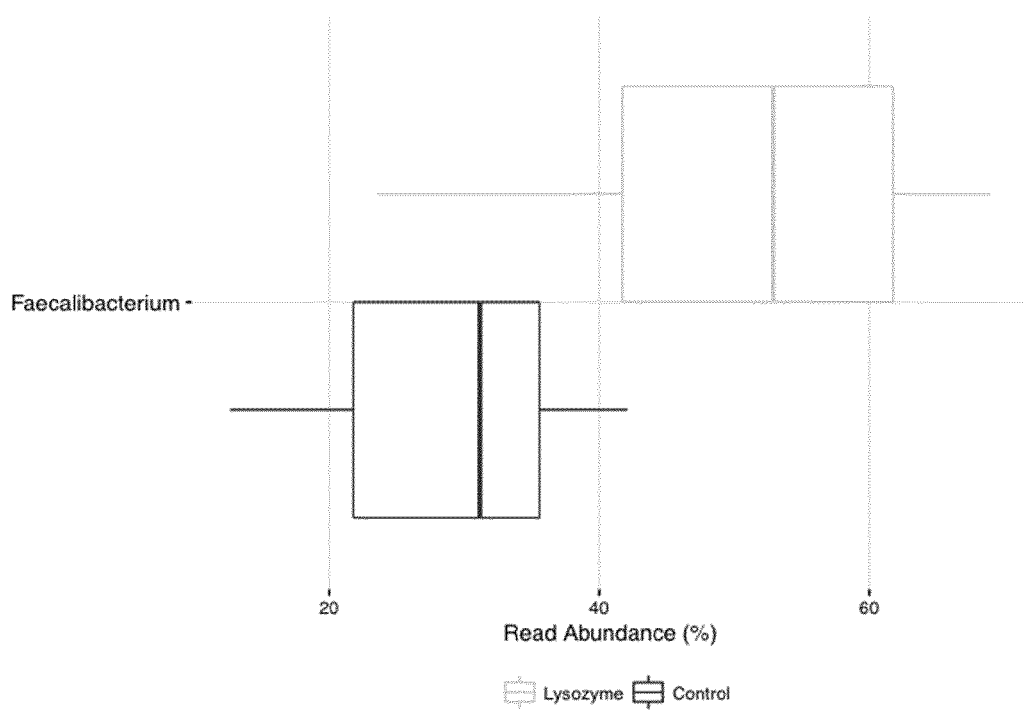
Figure 5C:
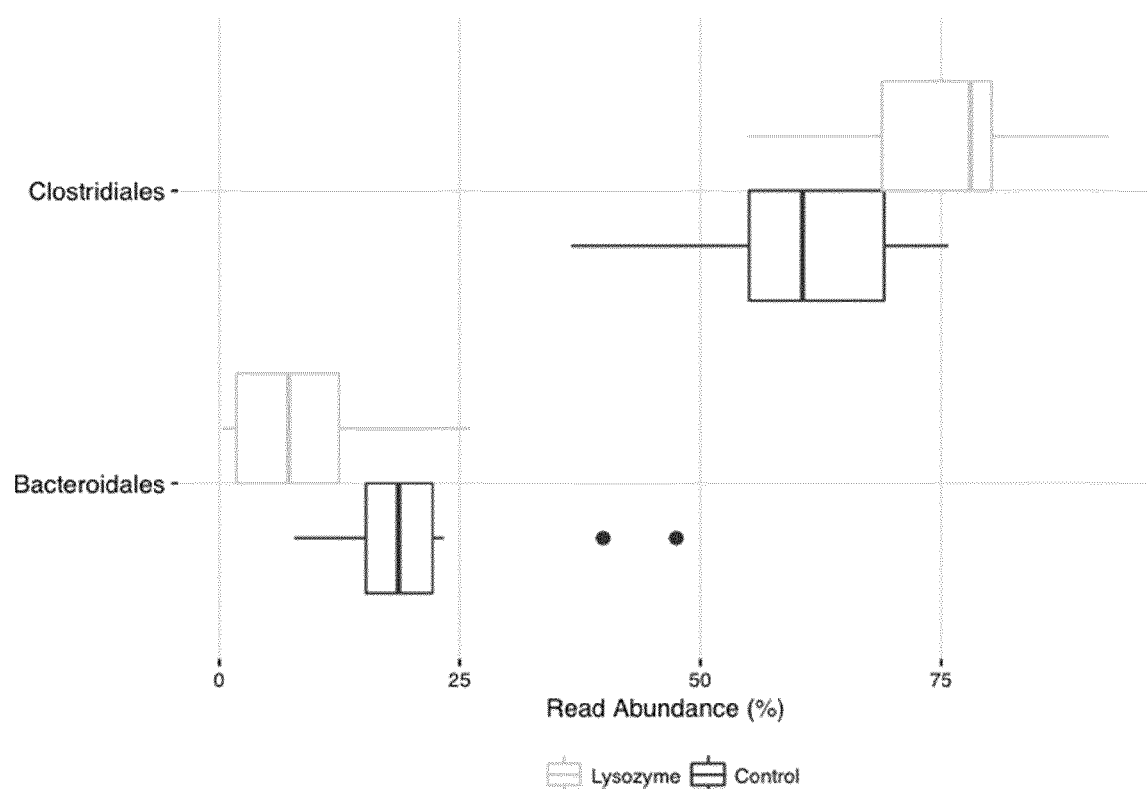

12 Claims, 9 Drawing Sheets
Specification includes a Sequence Listing.

ANIMAL FEED COMPOSITIONS AND USES THEREOF

CROSS-REFERENCE TO RELATED APPLICATIONS

This application is a 35 U.S.C. 371 national application of PCT/EP2016/065682 filed Jul. 4, 2016, which claims priority or the benefit under 35 U.S.C. 119 of European application no. 15174931.4 filed Jul. 2, 2015. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to animal feed compositions comprising polypeptides having lysozyme activity and polypeptides having phytase activity and uses thereof.

Description of the Related Art

Lysozyme is an O-glycosyl hydrolase produced as a defensive mechanism against bacteria by many organisms. The enzyme causes the hydrolysis of bacterial cell walls by cleaving the glycosidic bonds of peptidoglycan; an important structural molecule in bacteria. After having their cell walls weakened by lysozyme action, bacterial cells lyse as a result of umbalanced osmotic pressure.

Lysozyme naturally occurs in many organisms such as viruses, plants, insects, birds, reptiles and mammals. In mammals, Lysozyme has been isolated from nasal secretions, saliva, tears, intestinal content, urine and milk. The enzyme cleaves the glycosidic bond between carbon number 1 of N-acetylmuramic acid and carbon number 4 of N-acetyl-D-glucosamine. In vivo, these two carbohydrates are polymerized to form the cell wall polysaccharide of many microorganisms.

Lysozyme has been classified into five different glycoside hydrolase (GH) families (CAZy, www.cazy.org): hen egg-white lysozyme (GH22), goose egg-white lysozyme (GH23), bacteriophage T4 lysozyme (GH24), *Sphingomonas* flagellar protein (GH73) and *Chalaropsis* lysozymes (GH25). Lysozymes from the families GH23 and GH24 are primarily known from bacteriophages and have only recently been identified in fungi. The lysozyme family GH25 has been found to be structurally unrelated to the other lysozyme families.

Lysozyme extracted from hen egg white is the primary product available on the commercial market, but does not cleave N,6-O-diacetylmuramic acid in e.g. *Staphylococcus aureus* cell walls and is thus unable to lyse this important human pathogen among others (Masschalck B, Deckers D, Michiels C W (2002), "Lytic and nonlytic mechanism of inactivation of gram-positive bacteria by lysozyme under atmospheric and high hydrostatic pressure", *J Food Prof* 65(12):1916-23).

Phosphorus is an essential element for the growth of living organisms. In animal feed, phosphorus can be found in e.g. cereals and pulses mainly in the form of phytate. However, monogastric animals such as pigs, poultry and fish are not capable of directly absorbing phytate or phytic acid. This results in the excretion of phytate resulting in phosphorus being dischared into waterways in regions with intensive livestock production. Furthermore, phytic acid binds to metals such as calcium, copper or zinc and has a negative effect on the metabolism of monogastric animals. In order to compensate for the phosphate deficit of these animals and to ensure sufficient growth and health, inorganic phosphate is added to the animal feed.

However, the addition of inorganic phosphate is costly and leads to further adverse effects on the environment. By using a phytase in animal feeds, the phytate is hydrolyzed to substrates which the animal can utilise. This can result in improved animal performance (e.g. improved FCR or BWG), a reduction of the phosphate burden on the environment and a reduced cost to the farmer. Thus phytases are typically added to the diet of animals, and especially monogastric animals such as poultry and swine, and it is well known in the art that this can result in improved animal performance, such as improved body weight gain and/or feed conversion ratio (Selle & Ravindran, 2007, "Microbial phytase in poultry nutrition", *Anim. Feed Sci. Tech.*, 135:1-41 and Selle and Ravindran, 2008, "Phytate degrading enzymes in pig nutrition", *Livestock Sci.*, 113:99-122). However, in an ever growing world there is always an interest in improving the growth performance of an animal.

SUMMARY OF THE INVENTION

The present invention relates to an animal feed or animal feed additive comprising one or more polypeptides having phytase activity and one or more polypeptides having lysozyme activity, wherein:
 (a) the polypeptide having lysozyme activity is from glycosyl hydrolyase family 25 and is obtained or obtainable from the kingdom Fungi; and
 (b) the polypeptide having phytase activity is classified as an EC 3.1.3.26 phytase (4-phytase).

The present invention further relates to a method of improving one or more performance parameters in an animal comprising administering to one or more animals an animal feed or animal feed additive comprising one or more polypeptides having phytase activity and one or more polypeptides having lysozyme activity, wherein:
 (a) the polypeptide having lysozyme activity is from glycosyl hydrolyase family 25 and is obtained or obtainable from the kingdom Fungi;
 (b) the polypeptide having phytase activity is classified as an EC 3.1.3.26 phytase (4-phytase); and
 (c) the one or more performance parameters is selected from the group consisting of the European Production Efficiency Factor (EPEF) and Feed Conversion Ratio (FCR).

The present invention further relates to methods of improving the European Production Efficiency Factor (EPEF) and/or Feed Conversion Ratio (FCR) of an animal comprising administering to the animal the animal feed or the animal feed additive of the invention; use of the animal feed or animal feed additive of the invention for improving the European Production Efficiency Factor (EPEF) and/or Feed Conversion Ration (FCR); an animal feed or animal feed additive of the invention for use in the treatment of a *Clostridium perfringens* infection; and a method of increasing the population of bacteria of the genus *Faecalibacterium* in the microbiota of the GI tract of an animal, comprising administering to the animal an animal feed or animal feed additive of the invention.

OVERVIEW OF SEQUENCE LISTING

SEQ ID NO: 1 is the mature amino acid sequence of the AppA phytase from *E. Coli*.

SEQ ID NO: 2 is the mature amino acid sequence of the AppA2 phytase from *E. Coli*.

SEQ ID NO: 3 is the mature amino acid sequence of a phytase derived from *E. Coli*.

SEQ ID NO: 4 is the mature amino acid sequence of a phytase derived from *E. Coli*.

SEQ ID NO: 5 is the mature amino acid sequence of a phytase derived from *E. Coli*.

SEQ ID NO: 6 is the mature amino acid sequence of a phytase disclosed as SEQ ID NO: 1 of WO2008/017066.

SEQ ID NO: 7 is the mature amino acid sequence of a phytase disclosed as SEQ ID NO: 3 of WO2014/164442.

SEQ ID NO: 8 is the mature amino acid sequence of a phytase disclosed as SEQ ID NO: 6 of WO2014/164442.

SEQ ID NO: 9 is the mature amino acid sequence of a phytase disclosed as SEQ ID NO: 8 of WO2014/164442.

SEQ ID NO: 10 is the mature amino acid sequence of a phytase from *Citrobacter braakii* ATCC 51113.

SEQ ID NO: 11 is the mature amino acid sequence of a phytase from *Citrobacter gillenii*.

SEQ ID NO: 12 is the mature amino acid sequence of a phytase from *Citrobacter amalonaticus*.

SEQ ID NO: 13 is the mature amino acid sequence of a phytase from *Citrobacter braakii* YH-15.

SEQ ID NO: 14 is the mature amino acid sequence of a phytase from *Citrobacter freundii* P3-42.

SEQ ID NO: 15 is the mature amino acid sequence of a phytase from *Buttiauxella* sp P1-29.

SEQ ID NO: 16 is the mature amino acid sequence of a phytase from *Buttiauxella* sp P1-29.

SEQ ID NO: 17 is the mature amino acid sequence of a phytase disclosed as SEQ ID NO: 1 of WO2008/097619.

SEQ ID NO: 18 is the mature amino acid sequence of a phytase from *Buttiauxella gaviniae* DSM18930.

SEQ ID NO: 19 is the mature amino acid sequence of a phytase from *Buttiauxella agrestis* DSM18931.

SEQ ID NO: 20 is the mature amino acid sequence of a phytase from *Buttiauxella agrestis* DSM18932.

SEQ ID NO: 21 is the mature amino acid sequence of a phytase from *Peniophora lycii* CBS No. 686.96.

SEQ ID NO: 22 is the mature amino acid sequence of a phytase variant of *Peniophora lycii* CBS No. 686.96.

SEQ ID NO: 23 is the mature amino acid sequence of a phytase from *Hafnia alvei*.

SEQ ID NO: 24 is the mature amino acid sequence of a phytase from *Hafnia* sp. LU11047.

SEQ ID NO: 25 is the mature amino acid sequence of a fusion phytase disclosed as SEQ ID NO: 18 of WO2011/048046.

SEQ ID NO: 26 is the mature amino acid sequence of a fusion phytase variant disclosed as SEQ ID NO: 24 of WO2012/143862.

SEQ ID NO: 27 is the mature amino acid sequence of a wild type GH25 lysozyme from *Acremonium alcalophilum* with N-terminal SPIRR as described in WO 2013/076253.

SEQ ID NO: 28 is the mature amino acid sequence of a wild type GH22 lysozyme from *Gallus gallus* (hen egg white lysozyme).

SEQ ID NO: 29 is the mature amino acid sequence of a wild type GH25 lysozyme from *Aspergillus fumigatus* as described in WO 2011/104339.

SEQ ID NO: 30 is the mature amino acid sequence of a wild type GH25 lysozyme from *Acremonium alcalophilum* as described in WO 2013/076253.

SEQ ID NO: 31 is the forward primer 341F.

SEQ ID NO: 32 is the reverse primer 805R.

SEQ ID NO: 33 is the sequence representing the V3-V4 region of the 16S rRNA gene in OTU_1 classified as the bacterial genus *Faecalibacterium* from in vivo trial 4 (Example 8).

SEQ ID NO: 34 is the sequence representing the V3-V4 region of the 16S rRNA gene in OTU_8 classified as the bacterial genus *Faecalibacterium* from in vivo trial 4 (Example 8).

SEQ ID NO: 35 is the sequence representing the V3-V4 region of the 16S rRNA gene in OTU_45 classified as the bacterial genus *Faecalibacterium* from in vivo trial 4 (Example 8).

SEQ ID NO: 36 is the sequence representing the V3-V4 region of the 16S rRNA gene in OTU_150 classified as the bacterial genus *Faecalibacterium* from in vivo trial 4 (Example 8).

SEQ ID NO: 37 is the sequence representing the V3-V4 region of the 16S rRNA gene in OTU_204 classified as the bacterial genus *Faecalibacterium* from in vivo trial 4 (Example 8).

SEQ ID NO: 38 is the sequence representing the V3-V4 region of the 16S rRNA gene in OTU_259 classified as the bacterial genus *Faecalibacterium* from in vivo trial 4 (Example 8).

SEQ ID NO: 39 is the sequence representing the V3-V4 region of the 16S rRNA gene in OTU_380 classified as the bacterial genus *Faecalibacterium* from in vivo trial 4 (Example 8).

SEQ ID NO: 40 is the sequence representing the V3-V4 region of the 16S rRNA gene in OTU_436 classified as the bacterial genus *Faecalibacterium* from in vivo trial 4 (Example 8).

SEQ ID NO: 41 is the sequence representing the V3-V4 region of the 16S rRNA gene in OTU_462 classified as the bacterial genus *Faecalibacterium* from in vivo trial 4 (Example 8).

SEQ ID NO: 42 is the sequence representing the V3-V4 region of the 16S rRNA gene in OTU_752 classified as the bacterial genus *Faecalibacterium* from in vivo trial 4 (Example 8).

SEQ ID NO: 43 is the sequence representing the V3-V4 region of the 16S rRNA gene in OTU_1 classified as the bacterial genus *Faecalibacterium* from in vivo trial 5 (Example 9).

SEQ ID NO: 44 is the sequence representing the V3-V4 region of the 16S rRNA gene in OTU_5 classified as the bacterial genus *Faecalibacterium* from in vivo trial 5 (Example 9).

SEQ ID NO: 45 is the sequence representing the V3-V4 region of the 16S rRNA gene in OTU_193 classified as the bacterial genus *Faecalibacterium* from in vivo trial 5 (Example 9).

SEQ ID NO: 46 is the sequence representing the V3-V4 region of the 16S rRNA gene in OTU_260 classified as the bacterial genus *Faecalibacterium* from in vivo trial 5 (Example 9).

SEQ ID NO: 47 is the sequence representing the V3-V4 region of the 16S rRNA gene in OTU_273 classified as the bacterial genus *Faecalibacterium* from in vivo trial 5 (Example 9).

SEQ ID NO: 48 is the sequence representing the V3-V4 region of the 16S rRNA gene in OTU_315 classified as the bacterial genus *Faecalibacterium* from in vivo trial 5 (Example 9).

SEQ ID NO: 49 is the sequence representing the V3-V4 region of the 16S rRNA gene in OTU_387 classified as the bacterial genus *Faecalibacterium* from in vivo trial 5 (Example 9).

SEQ ID NO: 50 is the sequence representing the V3-V4 region of the 16S rRNA gene in OTU_402 classified as the bacterial genus *Faecalibacterium* from in vivo trial 5 (Example 9).

SEQ ID NO: 51 is the sequence representing the V3-V4 region of the 16S rRNA gene in OTU_415 classified as the bacterial genus *Faecalibacterium* from in vivo trial 5 (Example 9).

SEQ ID NO: 52 is the sequence representing the V3-V4 region of the 16S rRNA gene in OTU_496 classified as the bacterial genus *Faecalibacterium* from in vivo trial 5 (Example 9).

SEQ ID NO: 53 is the sequence representing the V3-V4 region of the 16S rRNA gene in OTU_518 classified as the bacterial genus *Faecalibacterium* from in vivo trial 5 (Example 9).

SEQ ID NO: 54 is the sequence representing the V3-V4 region of the 16S rRNA gene in OTU_527 classified as the bacterial genus *Faecalibacterium* from in vivo trial 5 (Example 9).

DEFINITIONS

Animal: The term "animal" refers to any animal except humans. Examples of animals are non-ruminants and ruminants. Ruminant animals include, for example, animals such as sheep, goats, cattle, e.g. beef cattle, cows, and young calves, deer, yank, camel, llama and kangaroo. Non-ruminant animals include monogastric animals, including but not limited to pigs or swine (including, but not limited to, piglets, growing pigs, and sows); poultry such as turkeys, ducks, quail, guinea fowl, geese, pigeons (including squabs) and chicken (including but not limited to broiler chickens (referred to herein as broiles), chicks, layer hens (referred to herein as layers)); horses (including but not limited to hotbloods, coldbloods and warm bloods) crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish).

Animal feed: The term "animal feed" refers to any compound, preparation, or mixture suitable for, or intended for intake by an animal. Animal feed for a monogastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix). An animal feed additive is a formulated enzyme product which may further comprise e.g. vitamins, minerals, enzymes, amino acids, preservatives and/or antibiotics; i.e. a premix. The animal feed additive/premix is typically mixed in a feed mill with concentrates and/or forage such as vegetable protein, legumes or other plant material. The animal feed is typically fed as a pelleted feed to monogastric animals.

Antimicrobial activity: The term "antimicrobial activity" is defined herein as an activity that kills or inhibits the growth of microorganisms, such as, algae, archea, bacteria, fungi and/or protozoans. The antimicrobial activity can for example be bactericidal meaning the killing of bacteria or bacteriostatic meaning the prevention of bacterial growth. The antimicrobial activity can include catalyzing the hydrolysis of 1,4-beta-linkages between N-acetylmuramic acid and N-acetyl-D-glucosamine residues in a peptidoglycan and between N-acetyl-D-glucosamine residues in chitodextrins. Antimicrobial activity can also include the lysozyme binding to the surface of the microorganism and inhibiting its growth. The antimicrobial effect can also include the use of the lysozymes of the present invention for activation of bacterial autolysins, as an immunostimulator, by inhibiting or reducing bacterial toxins and by an opsonin effect.

For the purpose of the present invention, antimicrobial activity is determined according to the antimicrobial assay described in Example 4 ("Determination of antimicrobial activity"). Antimicrobial activity is determined if there is a clearing zone when using 50% Mueller-Hinton broth, pH 6. Preferably the diameter of the clearing zone is 4 mm or more.

Concentrates: The term "concentrates" means feed with high protein and energy concentrations, such as fish meal, molasses, oligosaccharides, sorghum, seeds and grains (either whole or prepared by crushing, milling, etc. from e.g. corn, oats, rye, barley, wheat), oilseed press cake (e.g. from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

European Production Efficiency Factor (EPEF): The European Production Efficiency Factor is a way of comparing the performance of animals. This single-figure facilitates comparison of performance within and among farms and can be used to assess environmental, climatic and animal management variables. The EPEF is calculated as [(livability (%)×Liveweight (kg))/(Age at depletion (days)×FCR)]× 100, wherein livability is the percentage of animals alive at slaughter, Liveweight is the average weight of the animals at slaughter, age of depletion is the age of the animals at slaughter and FCR is the feed conversion ratio at slaughter.

*Faecalibacterium*: It is known (Větrovský T, Baldrian P (2013) The Variability of the 16S rRNA Gene in Bacterial Genomes and Its Consequences for Bacterial Community Analyses. PLoS ONE 8(2): e57923. doi: 10.1371/journal.pone.0057923) that the 16S rRNA gene sequence identity varies within a genus. It has been shown that the mean identity is 95.56 with a standard deviation of 3.68. It was also found that 12.2% of genera contain species with mean pairwise 16S rRNA gene similarity below 90%.

SEQ ID NO: 33 to 42 inclusive contains 16S rRNA gene sequences classified as genus *Faecalibacterium* from in vivo trial 4 (Example 8) and SEQ ID NO: 43 to 54 inclusive contains 16S rRNA gene sequences classified as genus *Faecalibacterium* from in vivo trial 5 (Example 9) where the V3-4 region of the 16S rRNA gene was used for amplification. The classification was performed using the program "rdp classifier" v.2.2. OTU_1 (SEQ ID NO: 33) from in vivo trial 4 (Example 8) was the most abundant *Faecalibacterium* in this trial. OTU_1 (SEQ ID NO: 43) from in vivo trial 5 (Example 9) was the most abundant *Faecalibacterium* in this trial.

Thus strains are hereby defined as *Faecalibacterium* wherein the sequence identity of the V3-V4 region of the 16S rRNA gene of said strain has at least 90% e.g., at least 91%, at least 92%, at least 93%, at least 94%, at least 95%, at least 96%, at least 97%, at least 98%, at least 99%, or 100% sequence identity to one or more of SEQ ID NO: 33 to 54. Preferably the sequence identity of the V3-V4 region of the 16S rRNA gene of said strain has at least 90%, more preferably at least 93%, even more preferably at least 95%, even more preferably at least 96%, even more preferably at least 97%, even more preferably at least 98%, even more preferably at least 99%, or most preferably 100% sequence identity to SEQ ID NO: 33.

Feed Conversion Ratio (FCR): FCR is a measure of an animal's efficiency in converting feed mass into increases of the desired output. Animals raised for meat—such as swine, poultry and fish—the output is the mass gained by the animal. Specifically FCR is calculated as feed intake divided by weight gain, all over a specified period. Improvement in FCR means reduction of the FCR value. A FCR improvement of 2% means that the FCR was reduced by 2%.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, *brassica* (e.g. kale, rapeseed (canola), rutabaga (swede), turnip), clover (e.g. alsike clover, red clover, subterranean clover, white clover), grass (e.g. Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Fragment: The term "fragment" means a polypeptide or a catalytic domain having one or more (e.g., several) amino acids absent from the amino and/or carboxyl terminus of a mature polypeptide or domain; wherein the fragment has lysozyme or phytase activity. In one aspect, a fragment comprises at least 170 amino acids, such as at least 175 amino acids, at least 180 amino acids, at least 185 amino acids, at least 190 amino acids, at least 195 amino acids or at least 200 amino acids of SEQ ID NO: 27 and has lysozyme activity. In another aspect, a fragment comprises at least 180 amino acids, such as at least 185 amino acids, at least 190 amino acids, at least 195 amino acids, at least 200 amino acids, at least 205 amino acids or at least 210 amino acids of SEQ ID NO: 29 and has lysozyme activity.

In another aspect, a fragment comprises at least 360 amino acids, such as at least 370 amino acids, at least 380 amino acids, at least 385 amino acids, at least 390 amino acids, at least 395 amino acids, at least 400 amino acids or at least 405 amino acids of any of the phytase sequences disclosed herein (i.e. SEQ ID NO: 1 to 26 inclusive) and has phytase activity.

Increases the proportion of bacteria of x in the microbiota of the GI tract of an animal: The term "increases the proportion of bacteria of x in the microbiota of the GI tract of an animal" means that the quantity of bacteria of a specific taxonomic rank (e.g. order or genus) has increased compared to a control sample. Samples of animal microbiota can be taken from the gut (i.e. gastrointestinal tract) of an animal (e.g. from broiler ceca or from the colon or ileum of swine) and analysed by examining the sequences (reads) of the 16S rRNA genes in the sample. The reads of the 16S rRNA genes can be clustered together based on sequence identity and each cluster can be compared to a database of known sequences of the 16S rRNA gene to identify the type of bacteria in that cluster. The clusters can be merged at different taxonomic levels (phylum, class, order, family, genus or species) to give a quantative analysis of the amount of bacteria within each taxonomy level over the entire sample By comparing the clusters from a control animal to an animal administered with a lysozyme of the invention, differences in the microbiota can be determined. Thus in one example, the proportion of bacteria of genus *Faecalibacterium* in the microbiota taken from broilers administered with a lysozyme of the invention increased from 28.4% to 50.4% (see table 9.5) compared to control (i.e. broilers not administered with a lysozyme). Thus in this example the proportion of bacteria of genus *Faecalibacterium* increased by 22%, which corresponds to an increase by a factor of 1.77.

In another example, the proportion of bacteria of order Clostridiales in the microbiota taken from broilers administered with a lysozyme of the invention increased from 60.1% to 74.4% (see table 9.7) compared to control. Thus in this example the proportion of bacteria of order Clostridiales decreased by 14.4%, which corresponds to a increase by a factor of 1.24.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Lysozyme activity: The term "lysozyme activity" means the enzymatic hydrolysis of the 1,4-beta-linkages between N-acetylmuramic acid and N-acetyl-D-glucosamine residues in a peptidoglycan or between N-acetyl-D-glucosamine residues in chitodextrins, resulting in bacteriolysis due to osmotic pressure. Lysozyme belongs to the enzyme class EC 3.2.1.17. Lysozyme activity is typically measured by turbidimetric determination. The method is based on the changes in turbidity of a suspension of *Micrococcus luteus* ATCC 4698 induced by the lytic action of lysozyme. In appropriate experimental conditions these changes are proportional to the amount of lysozyme in the medium (c.f. INS 1105 of the Combined Compendium of Food Additive Specifications of the Food and Agriculture Organisation of the UN (www.fao.org)). For the purpose of the present invention, lysozyme activity is determined according to the turbidity assay described in example 3 ("Determination of Lysozyme Activity") and the polypeptide has lysozyme activity if it shows activity against one or more bacteria, such as *Micrococcus luteus* ATCC 4698 and/or *Exiguobacterium undea* (DSM14481). In one aspect, the polypeptides of the present invention have at least 20%, e.g., at least 40%, at least 50%, at least 60%, at least 70%, at least 80%, at least 90%, at least 95%, or at least 100% of the lysozyme activity of SEQ ID NO: 27. In one aspect, the polypeptides of the present invention have at least 20%, e.g., at least 40%, at least 50%, at least 60%, at least 70%, at least 80%, at least 90%, at least 95%, or at least 100% of the lysozyme activity of SEQ ID NO: 29.

Mature polypeptide: The term "mature polypeptide" means a polypeptide in its final form following translation and any post-translational modifications, such as N-terminal processing, C-terminal truncation, glycosylation, phosphorylation, etc.

Operational taxonomic unit (OTU): The term "Operational taxonomic unit" means a cluster of sequences with a certain degree of similarity. In this case, 97 percent is chosen as the threshold for assigning sequences of the 16S rRNA gene to different OTUs, meaning that all sequences within a single OTU have at least 97 percent sequence identity. At this identity level each OTU is often considered (or assumed) to represent a single bacterial species.

Obtained or obtainable from: The term "obtained or obtainable from" means that the polypeptide may be found in an organism from a specific taxonomic rank. In one embodiment, the polypeptide is obtained or obtainable from the kingdom Fungi, wherein the term kingdom is the taxonomic rank. In a preferred embodiment, the polypeptide is obtained or obtainable from the phylum Ascomycota, wherein the term phylum is the taxonomic rank. In another preferred embodiment, the polypeptide is obtained or obtainable from the subphylum Pezizomycotina, wherein the term subphylum is the taxonomic rank. In another preferred embodiment, the polypeptide is obtained or obtainable from the class Eurotiomycetes, wherein the term class is the taxonomic rank.

If the taxonomic rank of a polypeptide is not known, it can easily be determined by a person skilled in the art by performing a BLASTP search of the polypeptide (using e.g. the National Center for Biotechnology Information (NCIB) website www.ncbi.nlm.nih.gov) and comparing it to the closest homologues. An unknown polypeptide which is a fragment of a known polypeptide is considered to be of the same taxonomic species. An unknown natural polypeptide or artificial variant which comprises a substitution, deletion and/or insertion in up to 10 positions is considered to be from the same taxonomic species as the known polypeptide.

Phytase activity: The term "phytase activity" means the hydrolysis of phytate (myo-inositol hexakisphosphate) to (1) myo-inositol and/or (2) mono-, di-, tri-, tetra- and/or pentaphosphates thereof and (3) inorganic phosphate. According to the ENZYME site (www.expasy.ch/enzyme/), three different types of phytases are known: the 3-phytase (alternative name 1-phytase; a myo-inositol hexaphosphate 3-phosphohydrolase, EC 3.1.3.8), the 4-phytase (alternative name 6-phytase, name based on 1L-numbering system and not 1D-numbering, EC 3.1.3.26), and the 5-phytase (EC 3.1.3.72). For the purposes of the present invention, all three types are included in the definition of phytase.

For the purpose of the present invention, phytase activity is determined by the libertation of inorganic phosphate from Na-phytate solution, wherein one phytase activity unit is the amount of enzyme which liberates 1 μmol inorganic phosphate per min from a 0.0051 M Na-phytate solution in 0.25 M Na-acetate, pH 5.5 and at 37° C. (Engelen, A. J., et al., 1994, "Simple and rapid determination of phytase activity", *J. AOAC Int.* 77:760-764). Examples of activity unit names are: FYT, FTU and U. Phytase activity may be determined using the assay as described in Example 2 ("Determination of phytase activity"). In one aspect, the polypeptides of the present invention have at least 20%, e.g., at least 40%, at least 50%, at least 60%, at least 70%, at least 80%, at least 90%, at least 95%, or at least 100% of the phytase activity of SEQ ID NO: 10.

Roughage: The term "roughage" means dry plant material with high levels of fiber, such as fiber, bran, husks from seeds and grains and crop residues (such as stover, copra, straw, chaff, sugar beet waste).

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well known recombinant methods or by classical purification methods.

Variant: The term "variant" means a polypeptide having lysozyme or phytase activity comprising an alteration, i.e., a substitution, insertion, and/or deletion, of one or more (several) amino acid residues at one or more (e.g., several) positions. A substitution means replacement of the amino acid occupying a position with a different amino acid; a deletion means removal of the amino acid occupying a position; and an insertion means adding 1, 2, or 3 amino acids adjacent to and immediately following the amino acid occupying the position.

In one aspect, a phytase variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and have at least 20%, e.g., at least 40%, at least 50%, at least 60%, at least 70%, at least 80%, at least 90%, at least 95%, or at least 100% of the phytase activity of the parent phytase, such as SEQ ID NO: 10. In another aspect, a lysozyme variant according to the invention may comprise from 1 to 5; from 1 to 10; from 1 to 15; from 1 to 20; from 1 to 25; from 1 to 30; from 1 to 35; from 1 to 40; from 1 to 45; or from 1-50, i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 alterations and have at least 20%, e.g., at least 40%, at least 50%, at least 60%, at least 70%, at least 80%, at least 90%, at least 95%, or at least 100% of the lysozyme activity of the parent lysozyme, such as SEQ ID NO: 27.

DETAILED DESCRIPTION OF THE INVENTION

Animal Feed or Animal Feed Additives Comprising Polypeptides Having Lysozyme Activity and Polypeptides Having Phytase Activity It has been surprisingly found that supplementing an animal feed comprising a phytase with a lysozyme from glycosyl hydrolyase family 25 (GH25 lysozyme) gives an additional performance benefit in animals compared to an animal feed comprising a phytase alone. This is surprising since improved animal performance of any GH25 lysozyme has never previously been demonstrated and this benefit is in addition to the performance benefit obtained by adding a phytase to the diet. Such an effect is apparent using all of the tested commercially available phytases used in animal feed, such as EC 3.1.3.26 phytases from *Citrobacter, E. coli, Buttiauxella* and *Peniophora*.

It has furthermore been discovered that the microbiota of the GI tract of an animal, such as broilers, is significantly altered by administering a lysozyme of the invention. In two of the in vivo broiler trials, samples from the broiler ceca were taken for microbial community (microbiome) analysis and it was surprisingly discovered that:

(a) treatment with a GH25 lysozyme (SEQ ID NO: 30) leads to a higher proportion of a bacterial species of the genus *Faecalibacterium* in the chicken gut and this shift is associated with increased European Production Efficiency Factor (EPEF) in chickens and this bacterial species has 96% identity to the species *Faecalibacterium prausnitzii;*

(b) treatment with a GH25 lysozyme (SEQ ID NO: 30) leads to a higher proportion of bacteria of the genus *Faecalibacterium* in the chicken gut and this shift is associated with increased European Production Efficiency Factor (EPEF) in chickens;

(c) treatment with a GH25 lysozyme (SEQ ID NO: 30) leads to a higher proportion of bacteria of the order Clostridiales in the chicken gut and this shift is associated with increased European Production Efficiency Factor (EPEF) in chickens;

(d) treatment with a GH25 lysozyme (SEQ ID NO: 30) leads to a lower proportion of bacteria of the order Bacteroidales in the chicken gut and this shift is associated with increased European Production Efficiency Factor (EPEF) in chickens.

Treatment of chickens with a GH25 lysozyme (SEQ ID NO: 30) resulted in higher levels of bacteria within the genus *Faecalibacterium* in the chicken gut environment. The closest known species is *Faecalibacterium prausnitzii*, which is an obligate anaerobe rod-shaped butyrate producing microorganism belonging to the phylum Firmicutes (Duncan et al. 2002, Int J Syst Evol Microbiol 52(Pt 6):2141-2146). It is abundant in the feces of several animal species (Haenen D, et al. "A diet high in resistant starch modulates microbiota composition, SOFA concentrations, and gene expression in pig intestine", J Nutr. 2013; 143: 274-283.; Lund M, Bjerrum L, Pedersen K. "Quantification of *Faecalibacterium prausnitzii*- and Subdoligranulum variabile-like bacteria in the cecum of chickens by real-time PCR", Poult Sci. 2010; 89: 1217-1224). In humans, high levels of *F. prausnitzii* have been associated with obesity (Balamurugan R, et al "Quantitative differences in intestinal *Faecalibacterium prausnitzii* in obese Indian children", Br J Nutr. 2010; 103: 335-338), while a low abundance of *F. prausnitzii* has been linked to Inflammatory Bowel Disease (IBD, i.e. Crohn's disease (Sokol H, et al. "*Faecalibacterium prausnitzii* is an anti-inflammatory commensal bacterium identified by gut microbiota analysis of Crohn disease patients", Proc Natl Acad Sci USA. 2008; 105: 16731-16736) and ulcerative colitis (Machiels K, et al. "A decrease of the butyrate-producing species *Roseburia hominis* and *Faecalibacterium prausnitzii* defines dysbiosis in patients with ulcerative colitis", Gut. 2013. doi: 10.1136/gutjnl-2013-304833)).

Additionally, the butyrate produced by *F. prausnitzii* is both an energy source to enterocytes and act as an anti-inflammatory agent (Miguel S, et al. "Identification of metabolic signatures linked to anti-inflammatory effects of *Faecalibacterium prausnitzii*", MBio. 2015; 6: doi: 10.1128/mBio.00300-15bioinf). Thus without wishing to be bound by theory, it is believed that the GH25 lysozyme of the invention increase the proportion of butyrate producing bacteria (such as those from the order Clostridiales and specifically the genus *Faecalibacterium*).

It can further be concluded that even though the broilers from in vivo trial 4 (Experiment 8) underwent a 3-day treatment with the antibiotic Enro-Sleecol, the GH25 lysozyme (SEQ ID NO: 30) induced the same significant shift in the microbial composition in the chicken gut as when an antibiotic was not administered; i.e. a higher proportion of bacterial species within the genus *Faecalibacterium*, an overall increase in the proportion of bacteria of the order Clostridiales and a decrease in bacteria of the order Bacteroidales.

Thus in one aspect, the invention relates to an animal feed or animal feed additive comprising one or more polypeptides having phytase activity and one or more polypeptides having lysozyme activity, wherein:

(a) the polypeptide having lysozyme activity is from glycosyl hydrolyase family 25 and is obtained or obtainable from the kingdom Fungi; and (b) the polypeptide having phytase activity is classified as an EC 3.1.3.26 phytase (4-phytase).

In one embodiment, the EPEF is improved by at least 1%, such as by at least 1.5%, at least 2.0%, at least 2.5%, at least 3%, at least 3.5%, at least 4% or at least 5%. In another embodiment, the EPEF is improved by between 1% and 15%, such as between 1% and 12%, between 1% and 10%, 1.5% and 8%, 2.0% and 7%, or any combination of these intervals.

In one embodiment, the FCR is improved by at least 1%, such as by at least 1.25%, at least 1.5% or at least 1.75%. In another embodiment, the FCR is improved by between 1% and 5%, such as between 1% and 4%, between 1% and 3%, 1.25% and 2.5%, 1.5% and 2%, or any combination of these intervals.

In one embodiment, the polypeptide having phytase activity is dosed at a level of 50 to 10000 FYT per kg animal feed, such as 100 to 6000 FYT per kg, 200 to 4000 FYT per kg, 250 to 3000 FYT per kg, 300 to 2500 FYT per kg, 350 to 2000 FYT per kg or 400 to 2000 FYT per kg animal feed, or any combination of these intervals (1 FYT=1 FTU=1U).

In one embodiment, the polypeptide having lysozyme activity is dosed at a level of 0.1 to 150 ppm enzyme protein per kg animal feed, such as 0.5 to 100 ppm, 1 to 75 ppm, 2 to 50 ppm, 3 to 25 ppm, 2 to 80 ppm, 5 to 60 ppm, 8 to 40 ppm, 10 to 30 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the polypeptide having lysozyme activity has antimicrobial activity towards *Clostridium perfringens*. In an embodiment, the polypeptide having lysozyme activity has at least 60%, at least 70%, at least 80%, at least 85%, at least 90%, at least 95% or at least 100% of the antimicrobial activity of SEQ ID NO: 27 against *Clostridium perfringens* under the conditions 50% MHB, pH 6. In an embodiment, the polypeptide having lysozyme activity has at least 60%, at least 70%, at least 80%, at least 85%, at least 90%, at least 95% or at least 100% of the antimicrobial activity of SEQ ID NO: 29 against *Clostridium perfringens* under the conditions 50% MHB, pH 6. Antimicrobial activity towards *Clostridium perfringens* can be determined according to the antimicrobial assay described in Example 4.

In one embodiment, the animal is any animal except humans. Examples of animals are non-ruminants, and ruminants. Ruminant animals include, for example, animals such as sheep, goats, cattle, e.g. beef cattle, cows, and young calves, deer, yank, camel, llama and kangaroo. Non-ruminant animals are preferred and include monogastric animals, such as pigs or swine (including, but not limited to, piglets, growing pigs, and sows); poultry such as turkeys, ducks, quail, guinea fowl, geese, pigeons (including squabs) and chicken (including but not limited to broiler chicks, layers); horses (including but not limited to hotbloods, coldbloods and warm bloods); crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish). In a preferred embodiment, the animal is a monogastric animal. In a more preferred embodiment, the animal is selected from the group consisting of swine, poultry, crustaceans and fish. In an even more preferred embodiment, the animal is selected from the group consisting of swine, piglet, growing pig, sow, chicken, broiler, layer, pullet and chick.

In one embodiment, the animal feed or animal feed additive comprising one or more polypeptides having phytase activity and one or more polypeptides having lysozyme activity may for example be used to stabilize the healthy microflora of animals, in particular livestock such as, but not limited to, sheep, goats, cattle (including, but not limited to, beef cattle, cows, and young calves), deer, pigs or swine (including, but not limited to, piglets, growing pigs, and sows), poultry (including, but not limited to, geese, turkeys, ducks and chicken such as broilers, chicks and layers); horses, moose and rabbits but also in fish (including but not limited to salmon, trout, tilapia, catfish and carps; and crustaceans (including but not limited to shrimps and prawns)) by suppressing growth/intestinal colonization of viral (such as Coronaviridae, Porcine reproductive and respiratory syndrome virus (PRRSV), Persivirus coursing Bovin virus diarre and likewise), parasitic pathogens (coccidian protozoa, *Eimeria maxima, Eimeria mitis*) or bacterial pathogens such as *Clostridium perfringens, Escherichia coli, Campylobacter coli, C. hyointestinalis* and *C. jejuni, Yersinia* ssp., *Treponema suis, Brachyspira hyodysenteriae, Lawsonia intracellularis* and *Salmonella*, such as *Salmonella enterica, Salmonella Typhimurium* and *Salmonella Mbandaka*. In a preferred embodiment a lysozyme is applied to chicken and has anti-microbal activity against *Clostridium perfringens*. In a further embodiment a lysozyme of the present invention is used as a feed additive, where it may provide a positive effect on the microbial balance of the animal digestive tract and in this way improve animal performance.

In one embodiment, the animal feed or animal feed additive increases the proportion of bacteria of genus *Faecalibacterium* in the microbiota of the GI tract of an animal. In an embodiment, the proportion of bacteria of genus *Faecalibacterium* is increased by at least 1%, such as at least 2%, at least 5%, at least 10%, at least 15% or at least 20%. In an alternative embodiment, the proportion of bacteria of genus *Faecalibacterium* is increased by a factor of at least 1.25, such as at least 1.50, at least 1.75, at least 2.0, at least 2.5 or at least 3.0.

In one embodiment, the animal feed or animal feed additive improves the European Production Efficiency Factor (EPEF) of an animal by at least 1% and increases the proportion of bacteria of genus *Faecalibacterium* in the microbiota of the GI tract of an animal. In an embodiment, the proportion of bacteria of genus *Faecalibacterium* is increased by at least 1%, such as at least 2%, at least 5%, at least 10%, at least 15% or at least 20% and the EPEF is increased by at least 1.5%, preferably by at least 2.0%, at least 2.5%, at least 3%, at least 3.5%, at least 4% or most preferably by at least 5%.

In one embodiment, the animal feed or animal feed additive improves the European Production Efficiency Factor (EPEF) of an animal by at least 1% and increases the proportion of bacteria of genus *Faecalibacterium* in the microbiota of the GI tract of an animal. In an embodiment, the proportion of bacteria of genus *Faecalibacterium* is increased by factor of at least 1.25, such as at least 1.50, at least 1.75, at least 2.0, at least 2.5 or at least 3.0 and the EPEF is increased by at least 1.5%, preferably by at least 2.0%, at least 2.5%, at least 3%, at least 3.5%, at least 4% or most preferably by at least 5%.

In one embodiment, the animal feed or animal feed additive improves the Feed Conversion Ratio (FCR) of an animal by at least 1% and increases the proportion of bacteria of genus *Faecalibacterium* in the microbiota of the GI tract of an animal. In an embodiment, the proportion of bacteria of genus *Faecalibacterium* is increased by at least 1%, such as at least 2%, at least 5%, at least 10%, at least 15% or at least 20% and the FCR is increased by at least 1.5%, preferably by at least 1.25%, preferably by at least 1.5% or most preferably by at least 1.75%.

In one embodiment, the animal feed or animal feed additive improves the Feed Conversion Ratio (FCR) of an animal by at least 1% and increases the proportion of bacteria of genus *Faecalibacterium* in the microbiota of the GI tract of an animal. In an embodiment, the proportion of bacteria of genus *Faecalibacterium* is increased by factor of at least 1.25, such as at least 1.50, at least 1.75, at least 2.0, at least 2.5 or at least 3.0 and the FCR is increased by at least 1.25%, preferably by at least 1.5% or most preferably by at least 1.75%.

In one embodiment, the animal feed or animal feed additive increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 33. In an embodiment, the proportion of bacteria of genus *Faecalibacterium* is increased by at least 1%, such as at least 2%, at least 5%, at least 10%, at least 15% or at least 20%. In an alternative embodiment, the proportion of bacteria of genus *Faecalibacterium* is increased by a factor of at least 1.25, such as at least 1.50, at least 1.75, at least 2.0, at least 2.5 or at least 3.0.

In one embodiment, the animal feed or animal feed additive improves the European Production Efficiency Factor (EPEF) of an animal by at least 1% and increases the proportion of bacteria of genus *Faecalibacterium* in the microbiota of the GI tract of an animal wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 33. In an embodiment, the proportion of bacteria of genus *Faecalibacterium* is increased by at least 1%, such as at least 2%, at least 5%, at least 10%, at least 15% or at least 20% and the EPEF is increased by at least 1.5%, preferably by at least 2.0%, at least 2.5%, at least 3%, at least 3.5%, at least 4% or most preferably by at least 5%.

In one embodiment, the animal feed or animal feed additive improves the European Production Efficiency Factor (EPEF) of an animal by at least 1% and increases the proportion of bacteria of genus *Faecalibacterium* in the microbiota of the GI tract of an animal wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 33. In an embodiment, the proportion of bacteria of genus *Faecalibacterium* is increased by factor of at least 1.25, such as at least 1.50, at least 1.75, at least 2.0, at least 2.5 or at least 3.0 and the EPEF is increased by at least 1.5%, preferably by at least 2.0%, at least 2.5%, at least 3%, at least 3.5%, at least 4% or most preferably by at least 5%.

In one embodiment, the animal feed or animal feed additive improves the Feed Conversion Ratio (FCR) of an animal by at least 1% and increases the proportion of bacteria of genus *Faecalibacterium* in the microbiota of the GI tract of an animal wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 33. In an embodiment, the proportion of bacteria of genus *Faecalibacterium* is increased by at least 1%, such as at least 2%, at least 5%, at least 10%, at least 15% or at least 20% and the FCR is increased by at least 1.5%, preferably by at least 1.25%, preferably by at least 1.5% or most preferably by at least 1.75%.

In one embodiment, the animal feed or animal feed additive improves the Feed Conversion Ratio (FCR) of an animal by at least 1% and increases the proportion of bacteria of genus *Faecalibacterium* in the microbiota of the GI tract of an animal wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 33. In an embodiment, the proportion of bacteria of genus *Faecalibacterium* is increased by factor of at least 1.25, such as at least 1.50, at least 1.75, at least 2.0, at least 2.5 or at least 3.0 and the FCR is increased by at least 1.25%, preferably by at least 1.5% or most preferably by at least 1.75%.

In one embodiment, the animal feed or animal feed additive increases the proportion of bacteria of order Clostridiales in the microbiota of the GI tract of an animal. In an embodiment, the proportion of bacteria of order Clostridiales is increased by at least 1%, such as at least 1.5%, at least 2%, at least 2.5%, at least 5% or at least 7.5%. In an alternative embodiment, the proportion of bacteria of order Clostridiales is increased by a factor of at least 1.25, such as at least 1.50, at least 1.75, at least 2.0, at least 2.5 or at least 3.0.

In one embodiment, the animal feed or animal feed additive improves the European Production Efficiency Factor (EPEF) of an animal by at least 1% and increases the proportion of bacteria of order Clostridiales in the microbiota of the GI tract of an animal. In an embodiment, the proportion of bacteria of order Clostridiales is increased by at least 1%, such as at least 1.5%, at least 2%, at least 2.5%, at least 5% or at least 7.5% and the EPEF is increased by at least 1.5%, preferably by at least 2.0%, at least 2.5%, at least 3%, at least 3.5%, at least 4% or most preferably by at least 5%.

In one embodiment, the animal feed or animal feed additive improves the European Production Efficiency Factor (EPEF) of an animal by at least 1% and increases the proportion of bacteria of order Clostridiales in the microbiota of the GI tract of an animal. In an embodiment, the proportion of bacteria of order Clostridiales is increased by factor of at least 1.025, such as at least 1.05, at least 1.075, at least 1.1, at least 1.15 or at least 1.2 and the EPEF is increased by at least 1.5%, preferably by at least 2.0%, at least 2.5%, at least 3%, at least 3.5%, at least 4% or most preferably by at least 5%.

In one embodiment, the animal feed or animal feed additive improves the Feed Conversion Ratio (FCR) of an animal by at least 1% and increases the proportion of bacteria of order Clostridiales in the microbiota of the GI tract of an animal. In an embodiment, the proportion of bacteria of order Clostridiales is increased by at least 1%, such as at least 1.5%, at least 2%, at least 2.5%, at least 5% or at least 7.5% and the FCR is increased by at least 1.5%, preferably by at least 1.25%, preferably by at least 1.5% or most preferably by at least 1.75%.

In one embodiment, the animal feed or animal feed additive improves the Feed Conversion Ratio (FCR) of an animal by at least 1% and increases the proportion of bacteria of order Clostridiales in the microbiota of the GI tract of an animal. In an embodiment, the proportion of bacteria of order Clostridiales is increased by factor of at least 1.025, such as at least 1.05, at least 1.075, at least 1.1, at least 1.15 or at least 1.2 and the FCR is increased by at least 1.25%, preferably by at least 1.5% or most preferably by at least 1.75%.

In one embodiment, the polypeptide having lysozyme activity is obtained or obtainable from the kingdom Fungi. In a preferred embodiment, the polypeptide having lysozyme activity is obtained or obtainable from the phylum Ascomycota, such as the sub-phylum Pezizomycotina. In a more preferred embodiment, the polypeptide having lysozyme activity is obtained or obtainable from the class Eurotiomycetes. In a more preferred embodiment, the polypeptide having lysozyme activity is obtained or obtainable from the order Eurotiales. In a more preferred embodiment, the polypeptide having lysozyme activity is obtained or obtainable from the family Aspergillaceae. In a more preferred embodiment, the polypeptide having lysozyme activity is obtained or obtainable from the genus *Aspergillus*.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27 and has at least 60% of the antimicrobial activity of SEQ ID NO: 27 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27 and has at least 70% of the antimicrobial activity of SEQ ID NO: 27 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27 and has at least 80% of the antimicrobial activity of SEQ ID NO: 27 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27 and has at least 90% of the antimicrobial activity of SEQ ID NO: 27 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27 and has at least 100% of the antimicrobial activity of SEQ ID NO: 27 against *Clostridium perfringens* under the conditions 50% MHB, pH 6.

In a preferred embodiment, the polypeptide having lysozyme activity comprises or consists of the amino acid sequence of SEQ ID NO: 27 or an allelic variant thereof; or is a fragment thereof having lysozyme activity, wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids. In an embodiment, the fragment has at least 60%, at least 70%, at least 80%, at least 85%, at least 90%, at least 95% or at least 100% of the antimicrobial activity of SEQ ID NO: 27 against *Clostridium perfringens* under the conditions 50% MHB, pH 6. In another aspect, the polypeptide comprises or consists of amino acids 1 to 213 of SEQ ID NO: 27.

In another embodiment, the polypeptide having lysozyme activity is a variant of SEQ ID NO: 27 wherein the variant has lysozyme activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 27 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 27 is not more than 10, e.g., 1, 2, 3, 4, 5, 6, 7, 8, 9 or 10. In another embodiment, the number of substitutions, deletions, and/or insertions in SEQ ID NO: 27 is not more than 10, e.g., 1, 2, 3, 4, 5, 6, 7, 8, 9 or 10. In a further embodiment, the number of substitutions, preferably conservative substitutions, in SEQ ID NO: 27 is not more than 10, e.g., 1, 2, 3, 4, 5, 6, 7, 8, 9 or 10. In a further embodiment, the number of conservative substitutions in SEQ ID NO: 27 is not more than 10, e.g., 1, 2, 3, 4, 5, 6, 7, 8, 9 or 10. In an embodiment, the variant has at least 60%, at least 70%, at least 80%, at least 85%, at least 90%, at least 95% or at least 100% of the antimicrobial activity of SEQ ID NO: 27 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29 and has at least 60% of the antimicrobial activity of SEQ ID NO: 29 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29 and has at least 70% of the antimicrobial activity of SEQ ID NO: 29 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29 and has at least 80% of the antimicrobial activity of SEQ ID NO: 29 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29 and has at least 90% of the antimicrobial activity of SEQ ID NO: 29 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29 and has at least 100% of the antimicrobial activity of SEQ ID NO: 29 against *Clostridium perfringens* under the conditions 50% MHB, pH 6.

In a preferred embodiment, the polypeptide having lysozyme activity comprises or consists of the amino acid sequence of SEQ ID NO: 29 or an allelic variant thereof; or is a fragment thereof having lysozyme activity, wherein the fragment comprises at least 180 amino acids, such as at least 185 amino acids, at least 190 amino acids, at least 195 amino acids, at least 200 amino acids, at least 205 amino acids or at least 210 amino acids. In an embodiment, the fragment has at least 60%, at least 70%, at least 80%, at least 85%, at least 90%, at least 95% or at least 100% of the antimicrobial activity of SEQ ID NO: 29 against *Clostridium perfringens* under the conditions 50% MHB, pH 6. In another aspect, the polypeptide comprises or consists of amino acids 1 to 218 of SEQ ID NO: 29.

In another embodiment, the polypeptide having lysozyme activity is a variant of SEQ ID NO: 29 wherein the variant has lysozyme activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 29 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 29 is not more than 10, e.g., 1, 2, 3, 4, 5, 6, 7, 8, 9 or 10. In another embodiment, the number of substitutions, deletions, and/or insertions in SEQ ID NO: 29 is not more than 10, e.g., 1, 2, 3, 4, 5, 6, 7, 8, 9 or 10. In a further embodiment, the number of substitutions, preferably conservative substitutions, in SEQ ID NO: 29 is not more than 10, e.g., 1, 2, 3, 4, 5, 6, 7, 8, 9 or 10. In a further embodiment, the number of conservative substitutions in SEQ ID NO: 29 is not more than 10, e.g., 1, 2, 3, 4, 5, 6, 7, 8, 9 or 10. In an embodiment, the variant has at least 60%, at least 70%, at least 80%, at least 85%, at least 90%, at least 95% or at least 100% of the antimicrobial activity of SEQ ID NO: 29 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 30.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 30 and has at least 60% of the antimicrobial activity of SEQ ID NO: 30 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 30 and has at least 70% of the antimicrobial activity of SEQ ID NO: 30 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 30 and has at least 80% of the antimicrobial activity of SEQ ID NO: 30 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 30 and has at least 90% of the antimicrobial activity of SEQ ID NO: 30 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 30 and has at least 100% of the antimicrobial activity of SEQ ID NO: 30 against *Clostridium perfringens* under the conditions 50% MHB, pH 6.

In a preferred embodiment, the polypeptide having lysozyme activity comprises or consists of the amino acid sequence of SEQ ID NO: 30 or an allelic variant thereof; or is a fragment thereof having lysozyme activity, wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids. In an embodiment, the fragment has at least 60%, at least 70%, at least 80%, at least 85%, at least 90%, at least 95% or at least 100% of the antimicrobial activity of SEQ ID NO: 30 against *Clostridium perfringens* under the conditions 50% MHB, pH 6. In another aspect, the polypeptide comprises or consists of amino acids 1 to 208 of SEQ ID NO: 30.

In another embodiment, the polypeptide having lysozyme activity is a variant of SEQ ID NO: 30 wherein the variant has lysozyme activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 30 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 30 is not more than 10, e.g., 1, 2, 3, 4, 5, 6, 7, 8, 9 or 10. In another embodiment, the number of substitutions, deletions, and/or insertions in SEQ ID NO: 30 is not more than 10, e.g., 1, 2, 3, 4, 5, 6, 7, 8, 9 or 10. In a further embodiment, the number of substitutions, preferably conservative substitutions, in SEQ ID NO: 30 is not more than 10, e.g., 1, 2, 3, 4, 5, 6, 7, 8, 9 or 10. In a further embodiment, the number of conservative substitutions in SEQ ID NO: 30 is not more than 10, e.g., 1, 2, 3, 4, 5, 6, 7, 8, 9 or 10. In an embodiment, the variant has at least 60%, at least 70%, at least 80%, at least 85%, at least 90%, at least 95% or at least 100% of the antimicrobial activity of SEQ ID NO: 30 against *Clostridium perfringens* under the conditions 50% MHB, pH 6.

The amino acid changes in SEQ ID NO: 27, SEQ ID NO: 29 or SEQ ID NO: 30 may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for lysozyme activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

The crystal structure of the *Acremonium alkalophilum* CBS114.92 lysozyme was solved at a resolution of 1.3 Å as disclosed in WO 2013/076253. These atomic coordinates can be used to generate a three dimensional model depicting the structure of the *Acremonium alkalophilum* CBS114.92 lysozyme or homologous structures (such as the variants of the present invention). Using the x/ray structure, amino acid residues D95 and E97 (using SEQ ID NO: 27 for numbering) were identified as catalytic residues.

In one embodiment, the polypeptide having phytase activity is a 4-phytase (EC 3.1.3.26). In another embodiment, the phytase is obtained or obtainable from the kingdom Fungi. In a preferred embodiment, the polypeptide having phytase activity is obtained or obtainable from the phylum Basidiomycota. In a more preferred embodiment, the polypeptide having phytase activity is obtained or obtainable from the class Agaricomycetes. In a more preferred embodiment, the polypeptide having phytase activity is obtained or obtainable from the order Russulales. In a more preferred embodiment, the polypeptide having phytase activity is obtained or obtainable from the family Peniophoraceae. In a more preferred embodiment, the polypeptide having phytase activity is obtained or obtainable from the genus *Peniophora*

In a further embodiment, the phytase is of bacterial origin. In a preferred embodiment, the polypeptide having phytase activity is obtained or obtainable from the phylum Proteobacteria. In a more preferred embodiment, the polypeptide having phytase activity is obtained or obtainable from the class Gammaproteobacteria. In a more preferred embodiment, the polypeptide having phytase activity is obtained or obtainable from the order Enterobacteriales. In a more preferred embodiment, the polypeptide having phytase activity is obtained or obtainable from the family Enterobacteriaceae. In a more preferred embodiment, the polypeptide having phytase activity is obtained or obtainable from the genus *Citrobacter, Buttiauxella, Hafnia, Yersinia* and/or *Escherichia.*

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1. In an embodiment, the polypeptide is derived or derivable from *Escherichia.*

In a preferred embodiment, the polypeptide having phytase activity comprises or consists of the amino acid sequence of SEQ ID NO: 1 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 410 of SEQ ID NO: 1.

In another embodiment, the polypeptide having phytase activity is a variant of SEQ ID NO: 1 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 1 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 1 is not more than 10, e.g., 1, 2, 3, 4, 5, 6, 7, 8, 9 or 10. In another embodiment, the number of substitutions, deletions, and/or insertions in SEQ ID NO: 1 is not more than 10, e.g., 1, 2, 3, 4, 5, 6, 7, 8, 9 or 10. In a further embodiment, the number of substitutions, preferably conservative substitutions, in SEQ ID NO: 1 is not more than 10, e.g., 1, 2, 3, 4, 5, 6, 7, 8, 9 or 10. The amino acid changes may be those as previously described herein.

In particular embodiments, the polypeptide having phytase activity that is a variant of SEQ ID NO: 1 is selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4. In an embodiment, the polypeptide is derived or derivable from *Escherichia*.

In a preferred embodiment, the polypeptide having phytase activity comprises or consists of the amino acid sequence of SEQ ID NO: 4 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 410 of SEQ ID NO: 4.

In another embodiment, the polypeptide having phytase activity is a variant of SEQ ID NO: 4 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 4 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 4 is not more than 10, e.g., 1, 2, 3, 4, 5, 6, 7, 8, 9 or 10. In another embodiment, the number of substitutions, deletions, and/or insertions in SEQ ID NO: 4 is not more than 10, e.g., 1, 2, 3, 4, 5, 6, 7, 8, 9 or 10. In a further embodiment, the number of substitutions, preferably conservative substitutions, in SEQ ID NO: 4 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9. In an embodiment, the polypeptide is derived or derivable from *Escherichia*.

In a preferred embodiment, the polypeptide having phytase activity comprises or consists of the amino acid sequence of SEQ ID NO: 9 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 411 of SEQ ID NO: 9.

In another embodiment, the polypeptide having phytase activity is a variant of SEQ ID NO: 9 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 9 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 9 is not more than 10, e.g., 1, 2, 3, 4, 5, 6, 7, 8, 9 or 10. In another embodiment, the number of substitutions, deletions, and/or insertions in SEQ ID NO: 9 is not more than 10, e.g., 1, 2, 3, 4, 5, 6, 7, 8, 9 or 10. In a further embodiment, the number of substitutions, preferably conservative substitutions, in SEQ ID NO: 9 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10. In an embodiment, the polypeptide is derived or derivable from *Citrobacter*.

In a preferred embodiment, the polypeptide having phytase activity comprises or consists of the amino acid sequence of SEQ ID NO: 10 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 411 of SEQ ID NO: 10.

In another embodiment, the polypeptide having phytase activity is a variant of SEQ ID NO: 10 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 10 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 10 is not more than 10, e.g., 1, 2, 3, 4, 5, 6, 7, 8, 9 or 10. In another embodiment, the number of substitutions, deletions, and/or insertions in SEQ ID NO: 10 is not more than 10, e.g., 1, 2, 3, 4, 5, 6, 7, 8, 9 or 10. In a further embodiment, the number of substitutions, preferably conservative substitutions, in SEQ ID NO: 10 is not more than 10, e.g., 1, 2, 3, 4, 5, 6, 7, 8, 9 or 10. The amino acid changes may be those as previously described herein.

In particular embodiments, the polypeptide having phytase activity that is a variant of SEQ ID NO: 10 is selected from the group consisting of SEQ ID NO: 13 and SEQ ID NO: 14.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 11. In an embodiment, the polypeptide is derived or derivable from *Citrobacter*.

In a preferred embodiment, the polypeptide having phytase activity comprises or consists of the amino acid sequence of SEQ ID NO: 11 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 410 of SEQ ID NO: 11.

In another embodiment, the polypeptide having phytase activity is a variant of SEQ ID NO: 11 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 11 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 11 is not more than 10, e.g., 1, 2, 3, 4, 5, 6, 7, 8, 9 or 10. In another embodiment, the number of substitutions, deletions, and/or insertions in SEQ ID NO: 11 is not more than 10, e.g., 1, 2, 3, 4, 5, 6, 7, 8, 9 or 10. In a further embodiment, the number of substitutions, preferably conservative substitutions, in SEQ ID NO: 11 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12. In an embodiment, the polypeptide is derived or derivable from *Citrobacter*.

In a preferred embodiment, the polypeptide having phytase activity comprises or consists of the amino acid sequence of SEQ ID NO: 12 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 414 of SEQ ID NO: 12.

In another embodiment, the polypeptide having phytase activity is a variant of SEQ ID NO: 12 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 12 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 12 is not more than 10, e.g., 1, 2, 3, 4, 5, 6, 7, 8, 9 or 10. In another embodiment, the number of substitutions, deletions, and/or insertions in SEQ ID NO: 12 is not more than 10, e.g., 1, 2, 3, 4, 5, 6, 7, 8, 9 or 10. In a further embodiment, the number of substitutions, preferably conservative substitutions, in SEQ ID NO: 12 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15. In an embodiment, the polypeptide is derived or derivable from *Buttiauxella*.

In a preferred embodiment, the polypeptide having phytase activity comprises or consists of the amino acid sequence of SEQ ID NO: 15 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 413 of SEQ ID NO: 15.

In another embodiment, the polypeptide having phytase activity is a variant of SEQ ID NO: 15 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 15 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 15 is not more than 10, e.g., 1, 2, 3, 4, 5, 6, 7, 8, 9 or 10. In another embodiment, the number of substitutions, deletions, and/or insertions in SEQ ID NO: 15 is not more than 10, e.g., 1, 2, 3, 4, 5, 6, 7, 8, 9 or 10. In a further embodiment, the number of substitutions, preferably conservative substitutions, in SEQ ID NO: 15 is not more than 10, e.g., 1, 2, 3, 4, 5, 6, 7, 8, 9 or 10. The amino acid changes may be those as previously described herein.

In particular embodiments, the polypeptide having phytase activity that is a variant of SEQ ID NO: 15 is selected from the group consisting of SEQ ID NO: 16, SEQ ID NO: 17, SEQ ID NO: 18, SEQ ID NO: 19 and SEQ ID NO: 20.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 17. In an embodiment, the polypeptide is derived or derivable from *Buttiauxella*.

In a preferred embodiment, the polypeptide having phytase activity comprises or consists of the amino acid sequence of SEQ ID NO: 17 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 413 of SEQ ID NO: 17.

In another embodiment, the polypeptide having phytase activity is a variant of SEQ ID NO: 17 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 17 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 17 is not more than 10, e.g., 1, 2, 3, 4, 5, 6, 7, 8, 9 or 10. In another embodiment, the number of substitutions, deletions, and/or insertions in SEQ ID NO: 17 is not more than 10, e.g., 1, 2, 3, 4, 5, 6, 7, 8, 9 or 10. In a further embodiment, the number of substitutions, preferably conservative substitutions, in SEQ ID NO: 17 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18. In an embodiment, the polypeptide is derived or derivable from *Buttiauxella*.

In a preferred embodiment, the polypeptide having phytase activity comprises or consists of the amino acid sequence of SEQ ID NO: 18 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 413 of SEQ ID NO: 18.

In another embodiment, the polypeptide having phytase activity is a variant of SEQ ID NO: 18 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 18 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 18 is not more than 10, e.g., 1, 2, 3, 4, 5, 6, 7, 8, 9 or 10. In another embodiment, the number of substitutions, deletions, and/or insertions in SEQ ID NO: 18 is not more than 10, e.g., 1, 2, 3, 4, 5, 6, 7, 8, 9 or 10. In a further embodiment, the number of substitutions, preferably conservative substitutions, in SEQ ID NO: 18 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21. In an embodiment, the polypeptide is derived or derivable from *Peniophora*.

In a preferred embodiment, the polypeptide having phytase activity comprises or consists of the amino acid sequence of SEQ ID NO: 21 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 410 of SEQ ID NO: 21.

In another embodiment, the polypeptide having phytase activity is a variant of SEQ ID NO: 21 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 21 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 21 is not more than 10, e.g., 1, 2, 3, 4, 5, 6, 7, 8, 9 or 10. In another embodiment, the number of substitutions, deletions, and/or insertions in SEQ ID NO: 21 is not more than 10, e.g., 1, 2, 3, 4, 5, 6, 7, 8, 9 or 10. In a further embodiment, the number of substitutions, preferably conservative substitutions, in SEQ ID NO: 21 is not more than 10, e.g., 1, 2, 3, 4, 5, 6, 7, 8, 9 or 10. The amino acid changes may be those as previously described herein.

In particular embodiments, the polypeptide having phytase activity that is a variant of SEQ ID NO: 15 is SEQ ID NO: 22.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 22. In an embodiment, the polypeptide is derived or derivable from *Peniophora*.

In a preferred embodiment, the polypeptide having phytase activity comprises or consists of the amino acid sequence of SEQ ID NO: 22 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 410 of SEQ ID NO: 22.

In another embodiment, the polypeptide having phytase activity is a variant of SEQ ID NO: 22 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 22 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 22 is not more than 10, e.g., 1, 2, 3, 4, 5, 6, 7, 8, 9 or 10. In another embodiment, the number of substitutions, deletions, and/or insertions in SEQ ID NO: 22 is not more than 10, e.g., 1, 2, 3, 4, 5, 6, 7, 8, 9 or 10. In a further embodiment, the number of substitutions, preferably conservative substitutions, in SEQ ID NO: 22 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 23. In an embodiment, the polypeptide is derived or derivable from *Hafnia*.

In a preferred embodiment, the polypeptide having phytase activity comprises or consists of the amino acid sequence of SEQ ID NO: 23 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 413 of SEQ ID NO: 23.

In another embodiment, the polypeptide having phytase activity is a variant of SEQ ID NO: 23 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 23 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 23 is not more than 10, e.g., 1, 2, 3, 4, 5, 6, 7, 8, 9 or 10. In another embodiment, the number of substitutions, deletions, and/or insertions in SEQ ID NO: 23 is not more than 10, e.g., 1, 2, 3, 4, 5, 6, 7, 8, 9 or 10. In a further embodiment, the number of substitutions, preferably conservative substitutions, in SEQ ID NO: 23 is not more than 10, e.g., 1, 2, 3, 4, 5, 6, 7, 8, 9 or 10. The amino acid changes may be those as previously described herein.

In particular embodiments, the polypeptide having phytase activity that is a variant of SEQ ID NO: 15 is selected from the group consisting of SEQ ID NO: 24, SEQ ID NO: 25 and SEQ ID NO: 26.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 25. In an embodiment, the polypeptide is derived or derivable from *Hafnia*.

In a preferred embodiment, the polypeptide having phytase activity comprises or consists of the amino acid sequence of SEQ ID NO: 25 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 414 of SEQ ID NO: 25.

In another embodiment, the polypeptide having phytase activity is a variant of SEQ ID NO: 25 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 25 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 25 is not more than 10, e.g., 1, 2, 3, 4, 5, 6, 7, 8, 9 or 10. In another embodiment, the number of substitutions, deletions, and/or insertions in SEQ ID NO: 25 is not more than 10, e.g., 1, 2, 3, 4, 5, 6, 7, 8, 9 or 10. In a further embodiment, the number of substitutions, preferably conservative substitutions, in SEQ ID NO: 25 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 26. In an embodiment, the polypeptide is derived or derivable from *Hafnia*.

In a preferred embodiment, the polypeptide having phytase activity comprises or consists of the amino acid sequence of SEQ ID NO: 26 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 414 of SEQ ID NO: 26.

In another embodiment, the polypeptide having phytase activity is a variant of SEQ ID NO: 26 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 26 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 26 is not more than 10, e.g., 1, 2, 3, 4, 5, 6, 7, 8, 9 or 10. In another embodiment, the number of substitutions, deletions, and/or insertions in SEQ ID NO: 26 is not more than 10, e.g., 1, 2, 3, 4, 5, 6, 7, 8, 9 or 10. In a further embodiment, the number of substitutions, preferably conservative substitutions, in SEQ ID NO: 26 is not more than 10, e.g., 1, 2, 3, 4, 5, 6, 7, 8, 9 or 10. The amino acid changes may be those as previously described herein. In a particular embodiment, the polypeptide having phytase activity is a variant of SEQ ID NO: 26 comprising or consisting of the substitutions D2E, A4E, A6S, F8Y, K76N, N78T, V123A, E144A and G217S.

In a preferred embodiment, the animal feed or animal feed additive comprises one or more polypeptides having phytase activity, one or more polypeptides having lysozyme activity and one or more further components wherein:

(a) the polypeptide having lysozyme activity is selected from the group consisting of:
  (i) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27;
  (ii) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29;
  (iii) a variant of SEQ ID NO: 27 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
  (iv) a variant of SEQ ID NO: 29 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (v) a fragment of the polypeptide of (i) or (iii) that has lysozyme activity wherein the fragment comprises at least 170 amino acids, such as at least 175 amino acids, at least 180 amino acids, at least 185 amino acids, at least 190 amino acids, at least 195 amino acids or at least 200 amino acids; and
  (vi) a fragment of the polypeptide of (ii) or (iv) that has lysozyme activity wherein the fragment comprises at least 180 amino acids, such as at least 185 amino acids, at least 190 amino acids, at least 195 amino acids, at least 200 amino acids, at least 205 amino acids or at least 210 amino acids; and (b) the polypeptide having phytase activity is selected from the group consisting of:
- (i) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
- (ii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;
- (iii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9;
- (iv) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10;
- (v) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 11;
- (vi) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12;
- (vii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;
- (viii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 17;
- (ix) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18;
- (x) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21;
- (xi) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 22;
- (xii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 23;
- (xiii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 25;
- (xiv) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 26;
- (xv) a variant of SEQ ID NO: 1, SEQ ID NO: 4, SEQ ID NO: 9, SEQ ID NO: 10, SEQ ID NO: 11, SEQ ID NO: 12, SEQ ID NO: 15, SEQ ID NO: 17, SEQ ID NO: 18, SEQ ID NO: 21, SEQ ID NO: 22, SEQ ID NO: 23, SEQ ID NO: 25 or SEQ ID NO: 26 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
- (xvi) a fragment of the polypeptide of (i), (ii), (iii), (iv), (v), (vi), (vii), (viii), (ix), (x), (xi), (xii), (xiii), (xiv) or (xv) that has phytase activity wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids;

(c) the one or more further components is selected from the list consisting of one or more carriers, one or more additional enzymes, one or more microbes, one or more vitamins, one or more minerals, one or more amino acids; and one or more other feed ingredients; and (d) the animal feed or animal feed additive improves the European Production Efficiency Factor (EPEF) and/or Feed Conversion Ratio (FCR) of an animal by at least 1%, compared to an animal feed the same feed but excluding the lysozyme.

Non limiting examples of carriers, additional enzymes, microbes, vitamins, minerals, amino acids and other feed ingredients are as defined herein below.

In a further preferred embodiment, the EPEF is improved by at least 1.25%, such as by at least 1.5%, at least 2.0%, at least 2.5%, at least 3%, at least 3.5%, at least 4% or at least 5%. In another embodiment, the EPEF is improved by between 1% and 15%, such as between 1% and 12%, between 1% and 10%, 1.5% and 8%, 2.0% and 7%, or any combination of these intervals.

In a further preferred embodiment, the FCR is improved by at least 1.25%, such as by at least 1.25%, at least 1.5% or at least 1.75%. In another embodiment, the FCR is improved by between 1% and 5%, such as between 1% and 4%, between 1% and 3%, 1.25% and 2.5%, 1.5% and 2%, or any combination of these intervals.

In one embodiment, the polypeptide having phytase activity is dosed at a level of 10 to 20000 FYT per kg animal feed, such as 25 to 15000 FYT per kg, 50 to 10000 FYT per kg, 100 to 6000 FYT per kg, 200 to 4000 FYT per kg, 250 to 3000 FYT per kg, 300 to 2500 FYT per kg, 350 to 2000 FYT per kg or 400 to 2000 FYT per kg animal feed, or any combination of these intervals (1 FYT=1 FTU=1U).

In a further preferred embodiment, the polypeptide having lysozyme activity is dosed at a level of 0.01-200 ppm enzyme protein per kg animal feed, such as 0.1 to 150 ppm, 0.5 to 100 ppm, 1 to 75 ppm, 2 to 50 ppm, 3 to 25 ppm, 2 to 80 ppm, 5 to 60 ppm, 8 to 40 ppm or 10 to 30 ppm enzyme protein per kg animal feed, or any combination of these intervals.

In one embodiment, the polypeptide having lysozyme activity has antimicrobial activity towards *Clostridium perfringens*. In an embodiment, the polypeptide having lysozyme activity has at least 60%, at least 70%, at least 80%, at least 85%, at least 90%, at least 95% or at least 100% of the antimicrobial activity of SEQ ID NO: 27 against *Clostridium perfringens* under the conditions 50% MHB, pH 6. In an embodiment, the polypeptide having lysozyme activity has at least 60%, at least 70%, at least 80%, at least 85%, at least 90%, at least 95% or at least 100% of the antimicrobial activity of SEQ ID NO: 29 against *Clostridium perfringens* under the conditions 50% MHB, pH 6. Antimicrobial activity towards *Clostridium perfringens* can be determined according to the antimicrobial assay described in Example 4.

In a further preferred embodiment, the animal is a monogastric animal selected from the group consisting of swine (including, but not limited to, pigs, piglets, growing pigs, and sows) and poultry (including, but not limited to turkeys, ducks, chicken, broilers, chicks and layers).

Formulating Agent

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate. The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In an embodiment, the solid composition is in granulated form. The granule may have a matrix structure where the components are mixed homogeneously. However, the granule typically comprises a core particle and one or more coatings, which typically are salt and/or wax coatings. Examples of waxes are polyethylene glycols; polypropylenes; Carnauba wax; Candelilla wax; bees wax; hydrogenated plant oil or animal tallow such as hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; micro-crystalline wax; paraffin's; and fatty acids, such as hydrogenated linear long chained fatty acids and derivatives thereof. A preferred wax is palm oil or hydrogenated palm oil. The core particle can either be a homogeneous blend of lysozyme of the invention optionally combined with one or more additional enzymes and optionally together with one or more salts or an inert particle with the lysozyme of the invention optionally combined with one or more additional enzymes applied onto it.

In an embodiment, the material of the core particles are selected from the group consisting of inorganic salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals and clay minerals (also known as hydrous aluminium phyllosilicates). In a preferred embodiment, the core comprises a clay mineral such as kaolinite or kaolin.

The salt coating is typically at least 1 μm thick and can either be one particular salt or a mixture of salts, such as $Na_2SO_4$, $K_2SO_4$, $MgSO_4$ and/or sodium citrate. Other examples are those described in e.g. WO 2008/017659, WO 2006/034710, WO 1997/05245, WO 1998/54980, WO 1998/55599, WO 2000/70034 or polymer coating such as described in WO 2001/00042.

In another embodiment, the composition is a solid composition comprising the lysozyme of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate and calcium carbonate. In a preferred embodiment, the solid composition is in granulated form. In an embodiment, the solid composition is in granulated form and comprises a core particle, an enzyme layer comprising the lysozyme of the invention and a salt coating.

In a further embodiment, the formulating agent is selected from one or more of the following compounds: glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose. In a preferred embodiment, the formulating agent is selected from one or more of the following compounds:

1,2-propylene glycol, 1,3-propylene glycol, sodium sulfate, dextrin, cellulose, sodium thiosulfate, kaolin and calcium carbonate.

Animal Feed and Animal Feed Additives

Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises one or more polypeptides having phytase activity and one or more polypeptides having lysozyme activity as described herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen bv, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g. beet, sugar beet, spinach or *quinoa*. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) phytase/lysozyme/enzyme preparation may also be added before or during the feed ingredient step. Typically a liquid enzyme preparation comprises the phytase, the lysozyme or both the phytase and lysozyme of the invention optionally with a polyol, such as glycerol, ethylene glycol or propylene glycol, and is added after the pelleting step, such as by spraying the liquid formulation onto the pellets. The phytase and/or lysozyme may also be incorporated in a feed additive or premix.

Alternatively, the phytase/lysozyme can be prepared by freezing a mixture of liquid enzyme solution with a bulking agent such as ground soybean meal, and then lyophilizing the mixture.

In an embodiment, the composition comprises one or more additional enzymes. In an embodiment, the composition comprises one or more microbes. In an embodiment, the composition comprises one or more vitamins. In an embodiment, the composition comprises one or more minerals. In an embodiment, the composition comprises one or more amino acids. In an embodiment, the composition comprises one or more other feed ingredients.

In another embodiment, the composition comprises one or more of the polypeptides of the invention, one or more formulating agents and one or more additional enzymes. In an embodiment, the composition comprises one or more of the polypeptides of the invention, one or more formulating agents and one or more microbes. In an embodiment, the composition comprises one or more of the polypeptides of the invention, one or more formulating agents and one or more vitamins. In an embodiment, the composition comprises one or more of the polypeptides of the invention and one or more minerals. In an embodiment, the composition comprises the polypeptide of the invention, one or more formulating agents and one or more amino acids. In an embodiment, the composition comprises one or more of the polypeptides of the invention, one or more formulating agents and one or more other feed ingredients.

In a further embodiment, the composition comprises one or more of the polypeptides of the invention, one or more formulating agents and one or more components selected from the list consisting of: one or more additional enzymes;

one or more microbes; one or more vitamins; one or more minerals; one or more amino acids; and one or more other feed ingredients.

The final lysozyme concentration in the diet is within the range of 0.01-200 ppm enzyme protein per kg animal feed, such as 0.1 to 150 ppm, 0.5 to 100 ppm, 1 to 75 ppm, 2 to 50 ppm, 3 to 25 ppm, 2 to 80 ppm, 5 to 60 ppm, 8 to 40 ppm or 10 to 30 ppm enzyme protein per kg animal feed, or any combination of these intervals.

It is at present contemplated that the lysozyme is administered in one or more of the following amounts (dosage ranges): 0.01-200; 0.01-100; 0.5-100; 1-50; 5-100; 5-50; 10-100; 0.05-50; 5-25; or 0.10-10 all these ranges being in mg lysozyme per kg feed (ppm).

In one embodiment, the polypeptide having phytase activity is dosed at a level of 10 to 20000 FYT per kg animal feed, such as 25 to 15000 FYT per kg, 50 to 10000 FYT per kg, 100 to 6000 FYT per kg, 200 to 4000 FYT per kg, 250 to 3000 FYT per kg, 300 to 2500 FYT per kg, 350 to 2000 FYT per kg or 400 to 2000 FYT per kg animal feed, or any combination of these intervals (1 FYT=1 FTU=1U).

For determining mg lysozyme or phytase protein per kg feed, the lysozyme or phytase is purified from the feed composition, and the specific activity of the purified lysozyme or phytase is determined using a relevant assay (see under lysozyme or phytase activity). The lysozyme or phytase activity of the feed composition as such is also determined using the same assay, and on the basis of these two determinations, the dosage in mg lysozyme or phytase protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (')/0 meaning g additive per 100 g feed). This is so in particular for premixes.

The same principles apply for determining mg lysozyme/ phytase protein in feed additives. Of course, if a sample is available of the lysozyme/phytase used for preparing the feed additive or the feed, the specific activity is determined from this sample (no need to purify the lysozyme/phytase from the feed composition or the additive).

Additional Enzymes

In another embodiment, the compositions described herein optionally include one or more enzymes. Enzymes can be classified on the basis of the handbook Enzyme Nomenclature from NC-IUBMB, 1992), see also the ENZYME site at the internet: www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase, lysozyme and galactosidase is described in Henrissat et al, "The carbohydrate-active enzymes database (CAZy) in 2013", Nucl. Acids Res. (1 Jan. 2014) 42 (D1): D490-D495; see also www.cazy.org.

Thus the composition of the invention may also comprise at least one other enzyme selected from the group comprising of xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); arabinofuranosidase (EC 3.2.1.55); beta-xylosidase (EC 3.2.1.37); acetyl xylan esterase (EC 3.1.1.72); feruloyl esterase (EC 3.1.1.73); cellulase (EC 3.2.1.4); cellobiohydrolases (EC 3.2.1.91); beta-glucosidase (EC 3.2.1.21); pullulanase (EC 3.2.1.41), alpha-mannosidase (EC 3.2.1.24), mannanase (EC 3.2.1.25) and beta-glucanase (EC 3.2.1.4 or EC 3.2.1.6), or any combination thereof.

In a particular embodiment, the composition of the invention comprises a phytase (EC 3.1.3.8 or 3.1.3.26). Examples of commercially available phytases include Bio-Feed™ Phytase (Novozymes), RONOZYME® P, RONOZYME® NP and RONOZYME® HiPhos (DSM Nutritional Products), Natuphos™ (BASF), Finase® and Quantum® Blue (AB Enzymes), OptiPhos® (Huvepharma) Phyzyme® XP (Verenium/DuPont) and Axtra® PHY (DuPont). Other preferred phytases include those described in e.g. WO 98/28408, WO 00/43503, and WO 03/066847.

In a particular embodiment, the composition of the invention comprises a xylanase (EC 3.2.1.8). Examples of commercially available xylanases include RONOZYME® WX and RONOZYME® G2 (DSM Nutritional Products), Econase® XT and Barley (AB Vista), Xylathin® (Verenium), Hostazym® X (Huvepharma) and Axtra® XB (Xylanase/ beta-glucanase, DuPont).

In a particular embodiment, the composition of the invention comprises a protease (EC 3.4). Examples of commercially available proteases include RONOZYME® ProAct (DSM Nutritional Products).

Microbes

In an embodiment, the animal feed composition further comprises one or more additional microbes. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediocosus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, composition, animal feed additive or animal feed further comprises a bacterium from one or more of the following strains of *Bacillus subtilis:* 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, NRRL B-50136, NRRL B-50605, NRRL B-50606, NRRL B-50622 and PTA-7547.

In a more preferred embodiment, composition, animal feed additive or animal feed further comprises a bacterium from one or more of the following strains of *Bacillus pumilus*: NRRL B-50016, ATCC 700385, NRRL B-50885 or NRRL B-50886.

In a more preferred embodiment, composition, animal feed additive or animal feed further comprises a bacterium from one or more of the following strains of *Bacillus lichenformis*: NRRL B 50015, NRRL B-50621 or NRRL B-50623.

In a more preferred embodiment, composition, animal feed additive or animal feed further comprises a bacterium from one or more of the following strains of *Bacillus amyloliquefaciens*: DSM 29869, DSM 29872, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1\times10^4$ and $1\times10^{14}$ CFU/kg of dry matter, preferably between $1\times10^6$ and $1\times10^{12}$ CFU/kg of dry matter, and more preferably between $1\times10^7$ and $1\times10^{11}$ CFU/kg of dry matter. In a more preferred embodiment the bacterial count of each of the bacterial strains in the animal feed composition is between $1\times10^8$ and $1\times10^{10}$ CFU/kg of dry matter.

The bacterial count of each of the bacterial strains in the animal feed composition is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day. In a more preferred embodiment the bacterial count of each of the bacterial strains in the animal feed composition is between $1\times10^9$ and $1\times10^{11}$ CFU/animal/day.

In another embodiment, the one or more bacterial strains are present in the form of a stable spore.

Premix

In an embodiment, the animal feed may include a premix, comprising e.g. vitamins, minerals, enzymes, amino acids, preservatives, antibiotics, other feed ingredients or any combination thereof which are mixed into the animal feed.

Amino Acids

The composition of the invention may further comprise one or more amino acids. Examples of amino acids which are used in animal feed are lysine, alanine, beta-alanine, threonine, methionine and tryptophan.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium and zinc.

Non-limiting examples of macro minerals include calcium, magnesium, potassium and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
|---|---|---|
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise colouring agents, stabilisers, growth improving additives and aroma compounds/flavourings, polyunsaturated fatty acids (PUFAs); reactive oxygen generating species, antimicrobial peptides and anti-fungal polypeptides.

Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of stabilizing agents (e.g. acidifiers) are organic acids. Examples of these are benzoic acid (VevoVitall®, DSM Nutritional Products), formic acid, butyric acid, fumaric acid and propionic acid.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

The composition of the invention may further comprise at least one amino acid. Examples of amino acids which are used in animal feed are lysine, alanine, beta-alanine, threonine, methionine and tryptophan.

Methods of Improving Animal Performance

In a second aspect, the invention relates to a method of improving one or more performance parameters in an animal comprising administering to one or more animals an animal feed or animal feed additive comprising one or more polypeptides having phytase activity and one or more polypeptides having lysozyme activity, wherein:

(a) the polypeptide having lysozyme activity is from glycosyl hydrolyase family 25; and (b) the one or more performance parameters is selected from the group consisting of the European Production Efficiency Factor (EPEF) and Feed Conversion Ratio (FCR).

In a further aspect, the invention relates to a method of improving one or more performance parameters in an animal comprising administering to one or more animals an animal feed or animal feed additive comprising one or more polypeptides having phytase activity and one or more polypeptides having lysozyme activity, wherein:

(a) the polypeptide having lysozyme activity is from glycosyl hydrolyase family 25 and is obtained or obtainable from the kingdom Fungi;

(b) the polypeptide having phytase activity is classified as an EC 3.1.3.26 phytase (4-phytase); and (c) the one or more performance parameters is selected from the group consisting of the European Production Efficiency Factor (EPEF) and Feed Conversion Ratio (FCR).

In a preferred embodiment, the improvement is compared to the same feed but excluding the lysozyme.

In one embodiment, the EPEF is improved by at least 1%, such as by at least 1.5%, at least 2.0%, at least 2.5%, at least 3%, at least 3.5%, at least 4% or at least 5%. In another embodiment, the EPEF is improved by between 1% and 15%, such as between 1% and 12%, between 1% and 10%, 1.5% and 8%, 2.0% and 7%, or any combination of these intervals.

In one embodiment, the FCR is improved by at least 1%, such as by at least 1.25%, at least 1.5% or at least 1.75%. In another embodiment, the FCR is improved by between 1% and 5%, such as between 1% and 4%, between 1% and 3%, 1.25% and 2.5%, 1.5% and 2%, or any combination of these intervals.

In one embodiment, the polypeptide having phytase activity is dosed at a level of 50 to 10000 FYT per kg animal feed, such as 100 to 6000 FYT per kg, 200 to 4000 FYT per kg, 250 to 3000 FYT per kg, 300 to 2500 FYT per kg, 350 to 2000 FYT per kg or 400 to 2000 FYT per kg animal feed, or any combination of these intervals (1 FYT=1 FTU=1U).

In one embodiment, the polypeptide having lysozyme activity is dosed at a level of 0.1 to 150 ppm enzyme protein per kg animal feed, such as 0.1 to 150 ppm, 0.5 to 100 ppm, 1 to 75 ppm, 2 to 50 ppm, 3 to 25 ppm, 2 to 80 ppm, 5 to 60 ppm, 8 to 40 ppm, 10 to 30 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the animal is any animal except humans. Examples of animals are non-ruminants, and ruminants. Ruminant animals include, for example, animals such as sheep, goats, cattle, e.g. beef cattle, cows, and young calves, deer, yank, camel, llama and kangaroo. Non-ruminant animals are preferred and include monogastric animals, such as pigs or swine (including, but not limited to, piglets, growing pigs, and sows); poultry such as turkeys, ducks, quail, guinea fowl, geese, pigeons (including squabs) and chicken (including but not limited to broiler chicks, layers); horses (including but not limited to hotbloods, coldbloods and warm bloods); crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish). In a preferred embodiment, the animal is a monogastric animal. In a more preferred embodiment, the animal is selected from the group consisting of swine, poultry, crustaceans and fish. In an even more preferred embodiment, the animal is selected from the group consisting of swine, piglet, growing pig, sow, chicken, broiler, layer, pullet and chick.

In one embodiment, the polypeptide having lysozyme activity has antimicrobial activity towards *Clostridium perfringens*. In an embodiment, the polypeptide having lysozyme activity has at least 60%, at least 70%, at least 80%, at least 85%, at least 90%, at least 95% or at least 100% of the antimicrobial activity of SEQ ID NO: 27 against *Clostridium perfringens* under the conditions 50% MHB, pH 6. In an embodiment, the polypeptide having lysozyme activity has at least 60%, at least 70%, at least 80%, at least 85%, at least 90%, at least 95% or at least 100% of the antimicrobial activity of SEQ ID NO: 29 against *Clostridium perfringens* under the conditions 50% MHB, pH 6. Antimicrobial activity towards *Clostridium perfringens* can be determined according to the antimicrobial assay described in Example 4.

In one embodiment, the method increases the proportion of bacteria of genus *Faecalibacterium* in the microbiota of the GI tract of an animal. In an embodiment, the proportion of bacteria of genus *Faecalibacterium* is increased by at least 1%, such as at least 2%, at least 5%, at least 10%, at least 15% or at least 20%. In an alternative embodiment, the proportion of bacteria of genus *Faecalibacterium* is increased by a factor of at least 1.25, such as at least 1.50, at least 1.75, at least 2.0, at least 2.5 or at least 3.0.

In one embodiment, the method improves the European Production Efficiency Factor (EPEF) of an animal by at least 1% and increases the proportion of bacteria of genus *Faecalibacterium* in the microbiota of the GI tract of an animal. In an embodiment, the proportion of bacteria of genus *Faecalibacterium* is increased by at least 1%, such as at least 2%, at least 5%, at least 10%, at least 15% or at least 20% and the EPEF is increased by at least 1.5%, preferably by at least 2.0%, at least 2.5%, at least 3%, at least 3.5%, at least 4% or most preferably by at least 5%.

In one embodiment, the method improves the European Production Efficiency Factor (EPEF) of an animal by at least 1% and increases the proportion of bacteria of genus *Faecalibacterium* in the microbiota of the GI tract of an animal. In an embodiment, the proportion of bacteria of genus *Faecalibacterium* is increased by factor of at least 1.25, such as at least 1.50, at least 1.75, at least 2.0, at least 2.5 or at least 3.0 and the EPEF is increased by at least 1.5%, preferably by at least 2.0%, at least 2.5%, at least 3%, at least 3.5%, at least 4% or most preferably by at least 5%.

In one embodiment, the method improves the Feed Conversion Ratio (FCR) of an animal by at least 1% and increases the proportion of bacteria of genus *Faecalibacterium* in the microbiota of the GI tract of an animal. In an embodiment, the proportion of bacteria of genus *Faecalibacterium* is increased by at least 1%, such as at least 2%, at least 5%, at least 10%, at least 15% or at least 20% and the FCR is increased by at least 1.5%, preferably by at least 1.25%, preferably by at least 1.5% or most preferably by at least 1.75%.

In one embodiment, the method improves the Feed Conversion Ratio (FCR) of an animal by at least 1% and increases the proportion of bacteria of genus *Faecalibacterium* in the microbiota of the GI tract of an animal. In an embodiment, the proportion of bacteria of genus *Faecalibacterium* is increased by factor of at least 1.25, such as at least 1.50, at least 1.75, at least 2.0, at least 2.5 or at least 3.0 and the FCR is increased by at least 1.25%, preferably by at least 1.5% or most preferably by at least 1.75%.

In one embodiment, the method increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 33. In an embodiment, the proportion of bacteria of genus *Faecalibacterium* is increased by at least 1%, such as at least 2%, at least 5%, at least 10%, at least 15% or at least 20%. In an alternative embodiment, the proportion of bacteria of genus *Faecalibacterium* is increased by a factor of at least 1.25, such as at least 1.50, at least 1.75, at least 2.0, at least 2.5 or at least 3.0.

In one embodiment, the method improves the European Production Efficiency Factor (EPEF) of an animal by at least 1% and increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 33. In an embodiment, the proportion of bacteria of genus *Faecalibacterium* is increased by at least 1%, such as at least 2%, at least 5%, at least 10%, at least 15% or at least 20% and the EPEF is increased by at least 1.5%, preferably by at least 2.0%, at least 2.5%, at least 3%, at least 3.5%, at least 4% or most preferably by at least 5%.

In one embodiment, the method improves the European Production Efficiency Factor (EPEF) of an animal by at least 1% and increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 33. In an embodiment, the proportion of bacteria of genus *Faecalibacterium* is increased by factor of at least 1.25, such as at least 1.50, at least 1.75, at least 2.0, at least 2.5 or at least 3.0 and the EPEF is increased by at least 1.5%, preferably by at least 2.0%, at least 2.5%, at least 3%, at least 3.5%, at least 4% or most preferably by at least 5%.

In one embodiment, the method improves the Feed Conversion Ratio (FCR) of an animal by at least 1% and increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 33. In an embodiment, the proportion of bacteria of genus *Faecalibacterium* is increased by at least 1%, such as at least 2%, at least 5%, at least 10%, at least 15% or at least 20% and the FCR is increased by at least 1.5%, preferably by at least 1.25%, preferably by at least 1.5% or most preferably by at least 1.75%.

In one embodiment, the method improves the Feed Conversion Ratio (FCR) of an animal by at least 1% and increases the proportion of bacteria of genus *Faecalibacterium* in the microbiota of the GI tract of an animal, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 33. In an embodiment, the proportion of bacteria of genus *Faecalibacterium* is increased by factor of at least 1.25, such as at least 1.50, at least 1.75, at least 2.0, at least 2.5 or at least 3.0 and the FCR is increased by at least 1.25%, preferably by at least 1.5% or most preferably by at least 1.75%.

In one embodiment, the method increases the proportion of bacteria of order Clostridiales in the microbiota of the GI tract of an animal. In an embodiment, the proportion of bacteria of order Clostridiales is increased by at least 1%, such as at least 1.5%, at least 2%, at least 2.5%, at least 5% or at least 7.5%. In an alternative embodiment, the proportion of bacteria of order Clostridiales is increased by a factor of at least 1.25, such as at least 1.50, at least 1.75, at least 2.0, at least 2.5 or at least 3.0.

In one embodiment, the method improves the European Production Efficiency Factor (EPEF) of an animal by at least 1% and increases the proportion of bacteria of order Clostridiales in the microbiota of the GI tract of an animal. In an embodiment, the proportion of bacteria of order Clostridiales is increased by at least 1%, such as at least 1.5%, at least 2%, at least 2.5%, at least 5% or at least 7.5% and the EPEF is increased by at least 1.5%, preferably by at least 2.0%, at least 2.5%, at least 3%, at least 3.5%, at least 4% or most preferably by at least 5%.

In one embodiment, the method improves the European Production Efficiency Factor (EPEF) of an animal by at least 1% and increases the proportion of bacteria of order Clostridiales in the microbiota of the GI tract of an animal. In an embodiment, the proportion of bacteria of order Clostridiales is increased by factor of at least 1.025, such as at least 1.05, at least 1.075, at least 1.1, at least 1.15 or at least 1.2 and the EPEF is increased by at least 1.5%, preferably by at least 2.0%, at least 2.5%, at least 3%, at least 3.5%, at least 4% or most preferably by at least 5%.

In one embodiment, the method improves the Feed Conversion Ratio (FCR) of an animal by at least 1% and increases the proportion of bacteria of order Clostridiales in the microbiota of the GI tract of an animal. In an embodiment, the proportion of bacteria of order Clostridiales is increased by at least 1%, such as at least 1.5%, at least 2%, at least 2.5%, at least 5% or at least 7.5% and the FCR is increased by at least 1.5%, preferably by at least 1.25%, preferably by at least 1.5% or most preferably by at least 1.75%.

In one embodiment, the method improves the Feed Conversion Ratio (FCR) of an animal by at least 1% and increases the proportion of bacteria of order Clostridiales in the microbiota of the GI tract of an animal. In an embodiment, the proportion of bacteria of order Clostridiales is increased by factor of at least 1.025, such as at least 1.05, at least 1.075, at least 1.1, at least 1.15 or at least 1.2 and the FCR is increased by at least 1.25%, preferably by at least 1.5% or most preferably by at least 1.75%.

In one embodiment, the polypeptide having lysozyme activity is obtained or obtainable from the kingdom Fungi. In a preferred embodiment, the polypeptide having lysozyme activity is obtained or obtainable from the phylum Ascomycota, such as the sub-phylum Pezizomycotina. In a more preferred embodiment, the polypeptide having lysozyme activity is obtained or obtainable from the class Eurotiomycetes. In a more preferred embodiment, the polypeptide having lysozyme activity is obtained or obtainable from the order Eurotiales. In a more preferred embodiment, the polypeptide having lysozyme activity is obtained or obtainable from the family Aspergillaceae. In a more preferred embodiment, the polypeptide having lysozyme activity is obtained or obtainable from the genus *Aspergillus*.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27 and has at least 60% of the antimicrobial activity of SEQ ID NO: 27 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27 and has at least 70% of the antimicrobial activity of SEQ ID NO: 27 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27 and has at least 80% of the antimicrobial activity of SEQ ID NO: 27 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27 and has at least 90% of the antimicrobial activity of SEQ ID NO: 27 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27 and has at least 100% of the antimicrobial activity of SEQ ID NO: 27 against *Clostridium perfringens* under the conditions 50% MHB, pH 6.

In a preferred embodiment, the polypeptide having lysozyme activity comprises or consists of the amino acid sequence of SEQ ID NO: 27 or an allelic variant thereof; or is a fragment thereof having lysozyme activity, wherein the fragment comprises at least 170 amino acids, such as at least 175 amino acids, at least 177 amino acids, at least 180 amino acids, at least 185 amino acids, at least 190 amino acids, at least 195 amino acids or at least 200 amino acids. In an embodiment, the fragment has at least 60%, at least 70%, at least 80%, at least 85%, at least 90%, at least 95% or at least 100% of the antimicrobial activity of SEQ ID NO: 27 against *Clostridium perfringens* under the conditions 50% MHB, pH 6. In another aspect, the polypeptide comprises or consists of amino acids 1 to 213 of SEQ ID NO: 27. In another aspect, the polypeptide comprises or consists of amino acids 1 to 208 of SEQ ID NO: 30.

In another embodiment, the polypeptide having lysozyme activity is a variant of SEQ ID NO: 27 wherein the variant has lysozyme activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 27 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 27 is not more than 10, e.g., 1, 2, 3, 4, 5, 6, 7, 8, 9 or 10. In another embodiment, the number of substitutions, deletions, and/or insertions in SEQ ID NO: 27 is not more than 10, e.g., 1, 2, 3, 4, 5, 6, 7, 8, 9 or 10. In a further embodiment, the number of substitutions, preferably conservative substitutions, in SEQ ID NO: 27 is not more than 10, e.g., 1, 2, 3, 4, 5, 6, 7, 8, 9 or 10. In a further embodiment, the number of conservative substitutions in SEQ ID NO: 27 is not more than 10, e.g., 1, 2, 3, 4, 5, 6, 7, 8, 9 or 10. In an embodiment, the variant has at least 60%, at least 70%, at least 80%, at least 85%, at least 90%, at least 95% or at least 100% of the antimicrobial activity of SEQ ID NO: 27 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29 and has at least 60% of the antimicrobial activity of SEQ ID NO: 29 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29 and has at least 70% of the antimicrobial activity of SEQ ID NO: 29 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29 and has at least 80% of the antimicrobial activity of SEQ ID NO: 29 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29 and has at least 90% of the antimicrobial activity of SEQ ID NO: 29 against *Clostridium perfringens* under the conditions 50% MHB, pH 6.

In one embodiment, the polypeptide having lysozyme activity has at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29 and has at least 100% of the antimicrobial activity of SEQ ID NO: 29 against *Clostridium perfringens* under the conditions 50% MHB, pH 6.

In a preferred embodiment, the polypeptide having lysozyme activity comprises or consists of the amino acid sequence of SEQ ID NO: 29 or an allelic variant thereof; or is a fragment thereof having lysozyme activity, wherein the fragment comprises at least 180 amino acids, such as at least 185 amino acids, at least 190 amino acids, at least 195 amino acids, at least 200 amino acids, at least 205 amino acids or at least 210 amino acids. In an embodiment, the fragment has at least 60%, at least 70%, at least 80%, at least 85%, at least 90%, at least 95% or at least 100% of the antimicrobial activity of SEQ ID NO: 29 against *Clostridium perfringens* under the conditions 50% MHB, pH 6. In another aspect, the polypeptide comprises or consists of amino acids 1 to 218 of SEQ ID NO: 29.

In another embodiment, the polypeptide having lysozyme activity is a variant of SEQ ID NO: 29 wherein the variant has lysozyme activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 29 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 29 is not more than 10, e.g., 1, 2, 3, 4, 5, 6, 7, 8, 9 or 10. In another embodiment, the number of substitutions, deletions, and/or insertions in SEQ ID NO: 29 is not more than 10, e.g., 1, 2, 3, 4, 5, 6, 7, 8, 9 or 10. In a further embodiment, the number of substitutions, preferably conservative substitutions, in SEQ ID NO: 29 is not more than 10, e.g., 1, 2, 3, 4, 5, 6, 7, 8, 9 or 10. In a further embodiment, the number of conservative substitutions in SEQ ID NO: 29 is not more than 10, e.g., 1, 2, 3, 4, 5, 6, 7, 8, 9 or 10. In an embodiment, the variant has at least 60%, at least 70%, at least 80%, at least 85%, at least 90%, at least 95% or at least 100% of the antimicrobial activity of SEQ ID NO: 29 against *Clostridium perfringens* under the conditions 50% MHB, pH 6.

In one embodiment, the polypeptide having phytase activity is a 4-phytase (EC 3.1.3.26). In another embodiment, the phytase is obtained or obtainable from the kingdom Fungi. In a preferred embodiment, the polypeptide having phytase activity is obtained or obtainable from the phylum Basidiomycota. In a more preferred embodiment, the polypeptide having phytase activity is obtained or obtainable from the class Agaricomycetes. In a more preferred embodiment, the polypeptide having phytase activity is obtained or obtainable from the order Russulales. In a more preferred embodiment, the polypeptide having phytase activity is obtained or obtainable from the family Peniophoraceae. In a more preferred embodiment, the polypeptide having phytase activity is obtained or obtainable from the genus *Peniophora*

In a further embodiment, the phytase is of bacterial origin. In a preferred embodiment, the polypeptide having phytase activity is obtained or obtainable from the phylum Proteobacteria. In a more preferred embodiment, the polypeptide having phytase activity is obtained or obtainable from the class Gammaproteobacteria. In a more preferred embodiment, the polypeptide having phytase activity is obtained or obtainable from the order Enterobacteriales. In a more preferred embodiment, the polypeptide having phytase activity is obtained or obtainable from the family Enterobacteriaceae. In a more preferred embodiment, the polypeptide having phytase activity is obtained or obtainable from the genus *Citrobacter, Buttiauxella, Hafnia, Yersinia* and/or *Escherichia*.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1. In an embodiment, the polypeptide is derived or derivable from *Escherichia*.

In a preferred embodiment, the polypeptide having phytase activity comprises or consists of the amino acid sequence of SEQ ID NO: 1 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 410 of SEQ ID NO: 1.

In another embodiment, the polypeptide having phytase activity is a variant of SEQ ID NO: 1 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 1 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 1 is not more than 10, e.g., 1, 2, 3, 4, 5, 6, 7, 8, 9 or 10. In another embodiment, the number of substitutions, deletions, and/or insertions in SEQ ID NO: 1 is not more than 10, e.g., 1, 2, 3, 4, 5, 6, 7, 8, 9 or 10. In a further embodiment, the number of substitutions, preferably conservative substitutions, in SEQ ID NO: 1 is not more than 10, e.g., 1, 2, 3, 4, 5, 6, 7, 8, 9 or 10. The amino acid changes may be those as previously described herein.

In particular embodiments, the polypeptide having phytase activity that is a variant of SEQ ID NO: 1 is selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8 and SEQ ID NO: 9.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4. In an embodiment, the polypeptide is derived or derivable from *Escherichia*.

In a preferred embodiment, the polypeptide having phytase activity comprises or consists of the amino acid sequence of SEQ ID NO: 4 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 410 of SEQ ID NO: 4.

In another embodiment, the polypeptide having phytase activity is a variant of SEQ ID NO: 4 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 4 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 4 is not more than 10, e.g., 1, 2, 3, 4, 5, 6, 7, 8, 9 or 10. In another embodiment, the number of substitutions, deletions, and/or insertions in SEQ ID NO: 4 is not more than 10, e.g., 1, 2, 3, 4, 5, 6, 7, 8, 9 or 10. In a further embodiment, the number of substitutions, preferably conservative substitutions, in SEQ ID NO: 4 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9. In an embodiment, the polypeptide is derived or derivable from *Escherichia*.

In a preferred embodiment, the polypeptide having phytase activity comprises or consists of the amino acid sequence of SEQ ID NO: 9 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 411 of SEQ ID NO: 9.

In another embodiment, the polypeptide having phytase activity is a variant of SEQ ID NO: 9 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 9 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 9 is not more than 10, e.g., 1, 2, 3, 4, 5, 6, 7, 8, 9 or 10. In another embodiment, the number of substitutions, deletions, and/or insertions in SEQ ID NO: 9 is not more than 10, e.g., 1, 2, 3, 4, 5, 6, 7, 8, 9 or 10. In a further embodiment, the number of substitutions, preferably conservative substitutions, in SEQ ID NO: 9 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10. In an embodiment, the polypeptide is derived or derivable from *Citrobacter*.

In a preferred embodiment, the polypeptide having phytase activity comprises or consists of the amino acid sequence of SEQ ID NO: 10 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 411 of SEQ ID NO: 10.

In another embodiment, the polypeptide having phytase activity is a variant of SEQ ID NO: 10 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 10 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 10 is not more than 10, e.g., 1, 2, 3, 4, 5, 6, 7, 8, 9 or 10. In another embodiment, the number of substitutions, deletions, and/or insertions in SEQ ID NO: 10 is not more than 10, e.g., 1, 2, 3, 4, 5, 6, 7, 8, 9 or 10. In a further embodiment, the number of substitutions, preferably conservative substitutions, in SEQ ID NO: 10 is not more than 10, e.g., 1, 2, 3, 4, 5, 6, 7, 8, 9 or 10. The amino acid changes may be those as previously described herein.

In particular embodiments, the polypeptide having phytase activity that is a variant of SEQ ID NO: 10 is selected from the group consisting of SEQ ID NO: 13 and SEQ ID NO: 14.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 11. In an embodiment, the polypeptide is derived or derivable from *Citrobacter*.

In a preferred embodiment, the polypeptide having phytase activity comprises or consists of the amino acid sequence of SEQ ID NO: 11 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 411 of SEQ ID NO: 11.

In another embodiment, the polypeptide having phytase activity is a variant of SEQ ID NO: 11 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 11 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 11 is not more than 10, e.g., 1, 2, 3, 4, 5, 6, 7, 8, 9 or 10. In another embodiment, the number of substitutions, deletions, and/or insertions in SEQ ID NO: 11 is not more than 10, e.g., 1, 2, 3, 4, 5, 6, 7, 8, 9 or 10. In a further embodiment, the number of substitutions, preferably conservative substitutions, in SEQ ID NO: 11 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12. In an embodiment, the polypeptide is derived or derivable from *Citrobacter*.

In a preferred embodiment, the polypeptide having phytase activity comprises or consists of the amino acid sequence of SEQ ID NO: 12 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 414 of SEQ ID NO: 12.

In another embodiment, the polypeptide having phytase activity is a variant of SEQ ID NO: 12 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 12 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 12 is not more than 10, e.g., 1, 2, 3, 4, 5, 6, 7, 8, 9 or 10. In another embodiment, the number of substitutions, deletions, and/or insertions in SEQ ID NO: 12 is not more than 10, e.g., 1, 2, 3, 4, 5, 6, 7, 8, 9 or 10. In a further embodiment, the number of substitutions, preferably conservative substitutions, in SEQ ID NO: 12 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15. In an embodiment, the polypeptide is derived or derivable from *Buttiauxella*.

In a preferred embodiment, the polypeptide having phytase activity comprises or consists of the amino acid sequence of SEQ ID NO: 15 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 413 of SEQ ID NO: 15.

In another embodiment, the polypeptide having phytase activity is a variant of SEQ ID NO: 15 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 15 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 15 is not more than 10, e.g., 1, 2, 3, 4, 5, 6, 7, 8, 9 or 10. In another embodiment, the number of substitutions, deletions, and/or insertions in SEQ ID NO: 15 is not more than 10, e.g., 1, 2, 3, 4, 5, 6, 7, 8, 9 or 10. In a further embodiment, the number of substitutions, preferably conservative substitutions, in SEQ ID NO: 15 is not more than 10, e.g., 1, 2, 3, 4, 5, 6, 7, 8, 9 or 10. The amino acid changes may be those as previously described herein.

In particular embodiments, the polypeptide having phytase activity that is a variant of SEQ ID NO: 15 is selected from the group consisting of SEQ ID NO: 16, SEQ ID NO: 17, SEQ ID NO: 18, SEQ ID NO: 19 and SEQ ID NO: 20.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 17. In an embodiment, the polypeptide is derived or derivable from *Buttiauxella*.

In a preferred embodiment, the polypeptide having phytase activity comprises or consists of the amino acid sequence of SEQ ID NO: 17 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 413 of SEQ ID NO: 17.

In another embodiment, the polypeptide having phytase activity is a variant of SEQ ID NO: 17 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 17 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 17 is not more than 10, e.g., 1, 2, 3, 4, 5, 6, 7, 8, 9 or 10. In another embodiment, the number of substitutions, deletions, and/or insertions in SEQ ID NO: 17 is not more than 10, e.g., 1, 2, 3, 4, 5, 6, 7, 8, 9 or 10. In a further embodiment, the number of substitutions, preferably conservative substitutions, in SEQ ID NO: 17 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18. In an embodiment, the polypeptide is derived or derivable from *Buttiauxella*.

In a preferred embodiment, the polypeptide having phytase activity comprises or consists of the amino acid sequence of SEQ ID NO: 18 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 413 of SEQ ID NO: 18.

In another embodiment, the polypeptide having phytase activity is a variant of SEQ ID NO: 18 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 18 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 18 is not more than 10, e.g., 1, 2, 3, 4, 5, 6, 7, 8, 9 or 10. In another embodiment, the number of substitutions, deletions, and/or insertions in SEQ ID NO: 18 is not more than 10, e.g., 1, 2, 3, 4, 5, 6, 7, 8, 9 or 10. In a further embodiment, the number of substitutions, preferably conservative substitutions, in SEQ ID NO: 18 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21. In an embodiment, the polypeptide is derived or derivable from *Peniophora*.

In a preferred embodiment, the polypeptide having phytase activity comprises or consists of the amino acid sequence of SEQ ID NO: 21 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 410 of SEQ ID NO: 21.

In another embodiment, the polypeptide having phytase activity is a variant of SEQ ID NO: 21 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 21 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 21 is not more than 10, e.g., 1, 2, 3, 4, 5, 6, 7, 8, 9 or 10. In another embodiment, the number of substitutions, deletions, and/or insertions in SEQ ID NO: 21 is not more than 10, e.g., 1, 2, 3, 4, 5, 6, 7, 8, 9 or 10. In a further embodiment, the number of substitutions, preferably conservative substitutions, in SEQ ID NO: 21 is not more than 10, e.g., 1, 2, 3, 4, 5, 6, 7, 8, 9 or 10. The amino acid changes may be those as previously described herein.

In particular embodiments, the polypeptide having phytase activity that is a variant of SEQ ID NO: 15 is SEQ ID NO: 22.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 22. In an embodiment, the polypeptide is derived or derivable from *Peniophora*.

In a preferred embodiment, the polypeptide having phytase activity comprises or consists of the amino acid sequence of SEQ ID NO: 22 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 410 of SEQ ID NO: 22.

In another embodiment, the polypeptide having phytase activity is a variant of SEQ ID NO: 22 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 22 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 22 is not more than 10, e.g., 1, 2, 3, 4, 5, 6, 7, 8, 9 or 10. In another embodiment, the number of substitutions, deletions, and/or insertions in SEQ ID NO: 22 is not more than 10, e.g., 1, 2, 3, 4, 5, 6, 7, 8, 9 or 10. In a further embodiment, the number of substitutions, preferably conservative substitutions, in SEQ ID NO: 22 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 23. In an embodiment, the polypeptide is derived or derivable from *Hafnia*.

In a preferred embodiment, the polypeptide having phytase activity comprises or consists of the amino acid sequence of SEQ ID NO: 23 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 413 of SEQ ID NO: 23.

In another embodiment, the polypeptide having phytase activity is a variant of SEQ ID NO: 23 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 23 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 23 is not more than 10, e.g., 1, 2, 3, 4, 5, 6, 7, 8, 9 or 10. In another embodiment, the number of substitutions, deletions, and/or insertions in SEQ ID NO: 23 is not more than 10, e.g., 1, 2, 3, 4, 5, 6, 7, 8, 9 or 10. In a further embodiment, the number of substitutions, preferably conservative substitutions, in SEQ ID NO: 23 is not more than 10, e.g., 1, 2, 3, 4, 5, 6, 7, 8, 9 or 10. The amino acid changes may be those as previously described herein.

In particular embodiments, the polypeptide having phytase activity that is a variant of SEQ ID NO: 15 is selected from the group consisting of SEQ ID NO: 24, SEQ ID NO: 25 and SEQ ID NO: 26.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 25. In an embodiment, the polypeptide is derived or derivable from *Hafnia*.

In a preferred embodiment, the polypeptide having phytase activity comprises or consists of the amino acid sequence of SEQ ID NO: 25 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 414 of SEQ ID NO: 25.

In another embodiment, the polypeptide having phytase activity is a variant of SEQ ID NO: 25 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 25 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 25 is not more than 10, e.g., 1, 2, 3, 4, 5, 6, 7, 8, 9 or 10. In another embodiment, the number of substitutions, deletions, and/or insertions in SEQ ID NO: 25 is not more than 10, e.g., 1, 2, 3, 4, 5, 6, 7, 8, 9 or 10. In a further embodiment, the number of substitutions, preferably conservative substitutions, in SEQ ID NO: 25 is not more than 10, e.g., 1, 2, 3, 4, 5, 6, 7, 8, 9 or 10. The amino acid changes may be those as previously described herein.

In another embodiment, the polypeptide having phytase activity has at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 26. In an embodiment, the polypeptide is derived or derivable from *Hafnia*.

In a preferred embodiment, the polypeptide having phytase activity comprises or consists of the amino acid sequence of SEQ ID NO: 26 or an allelic variant thereof; or is a fragment thereof having phytase activity, wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids. In another aspect, the polypeptide comprises or consists of amino acids 1 to 414 of SEQ ID NO: 26.

In another embodiment, the polypeptide having phytase activity is a variant of SEQ ID NO: 26 wherein the variant has phytase activity and comprises one or more substitutions, and/or one or more deletions, and/or one or more insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions. In another embodiment, the number of positions comprising one or more amino acid substitutions, and/or one or more amino acid deletions, and/or one or more amino acid insertions or any combination thereof in SEQ ID NO: 26 is between 1 and 45, such as 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 26 is not more than 10, e.g., 1, 2, 3, 4, 5, 6, 7, 8, 9 or 10. In another embodiment, the number of substitutions, deletions, and/or insertions in SEQ ID NO: 26 is not more than 10, e.g., 1, 2, 3, 4, 5, 6, 7, 8, 9 or 10. In a further embodiment, the number of substitutions, preferably conservative substitutions, in SEQ ID NO: 26 is not more than 10, e.g., 1, 2, 3, 4, 5, 6, 7, 8, 9 or 10. The amino acid changes may be those as previously described herein.

In a preferred embodiment, the invention relates to a method of improving the European Production Efficiency Factor (EPEF) and Feed Conversion Ratio (FCR) of an animal comprising administering to the animal an animal feed or animal feed additive comprising one or more polypeptides having phytase activity and one or more polypeptides having lysozyme activity, wherein:

(a) the polypeptide having lysozyme activity is selected from the group consisting of:
  (i) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27;
  (ii) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29;
  (iii) a variant of SEQ ID NO: 27 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
  (iv) a variant of SEQ ID NO: 29 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(v) a fragment of the polypeptide of (i) or (iii) that has lysozyme activity wherein the fragment comprises at least 170 amino acids, such as at least 175 amino acids, at least 180 amino acids, at least 185 amino acids, at least 190 amino acids, at least 195 amino acids or at least 200 amino acids; and (vi) a fragment of the polypeptide of (ii) or (iv) that has lysozyme activity wherein the fragment comprises at least 180 amino acids, such as at least 185 amino acids, at least 190 amino acids, at least 195 amino acids, at least 200 amino acids, at least 205 amino acids or at least 210 amino acids; and (b) the polypeptide having phytase activity is selected from the group consisting of:

(i) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;

(ii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;

(iii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9;

(iv) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10;

(v) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 11;

(vi) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12;

(vii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;

(viii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 17;

(ix) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18;

(x) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21;

(xi) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 22;

(xii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 23;

(xiii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 25;

(xiv) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 26;

(xv) a variant of SEQ ID NO: 1, SEQ ID NO: 4, SEQ ID NO: 9, SEQ ID NO: 10, SEQ ID NO: 11, SEQ ID NO: 12, SEQ ID NO: 15, SEQ ID NO: 17, SEQ ID NO: 18, SEQ ID NO: 21, SEQ ID NO: 22, SEQ ID NO: 23, SEQ ID NO: 25 or SEQ ID NO: 26 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and (xvi) a fragment of the polypeptide of (i), (ii), (iii), (iv), (v), (vi), (vii), (viii), (ix), (x), (xi), (xii), (xiii), (xiv) or (xv) that has phytase activity wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids; and (c) the European Production Efficiency Factor (EPEF) is improved by at least 1% and the Feed Conversion Ratio (FCR) is improved by at least 1% compared to the same feed but excluding the lysozyme.

In a further preferred embodiment, the EPEF is improved by at least 1.25%, such as by at least 1.5%, at least 2.0%, at least 2.5%, at least 3%, at least 3.5%, at least 4% or at least 5%. In another embodiment, the EPEF is improved by between 1% and 15%, such as between 1% and 12%, between 1% and 10%, 1.5% and 8%, 2.0% and 7%, or any combination of these intervals.

In a further preferred embodiment, the FCR is improved by at least 1.25%, such as by at least 1.25%, at least 1.5% or at least 1.75%. In another embodiment, the FCR is improved by between 1% and 5%, such as between 1% and 4%, between 1% and 3%, 1.25% and 2.5%, 1.5% and 2%, or any combination of these intervals.

In one embodiment, the polypeptide having phytase activity is dosed at a level of 10 to 20000 FYT per kg animal feed, such as 25 to 15000 FYT per kg, 50 to 10000 FYT per kg, 100 to 6000 FYT per kg, 200 to 4000 FYT per kg, 250 to 3000 FYT per kg, 300 to 2500 FYT per kg, 350 to 2000 FYT per kg or 400 to 2000 FYT per kg animal feed, or any combination of these intervals (1 FYT=1 FTU=1U).

In one embodiment, the polypeptide having lysozyme activity is dosed at a level of 0.01-200 ppm enzyme protein per kg animal feed, such as 0.1 to 150 ppm, 0.5 to 100 ppm, 1 to 75 ppm, 2 to 50 ppm, 3 to 25 ppm, 2 to 80 ppm, 5 to 60 ppm, 8 to 40 ppm, 10 to 30 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the polypeptide having lysozyme activity has antimicrobial activity towards *Clostridium perfringens*. In an embodiment, the polypeptide having lysozyme activity has at least 60%, at least 70%, at least 80%, at least 85%, at least 90%, at least 95% or at least 100% of the antimicrobial activity of SEQ ID NO: 27 against *Clostridium perfringens* under the conditions 50% MHB, pH 6. In an embodiment, the polypeptide having lysozyme activity has at least 60%, at least 70%, at least 80%, at least 85%, at least 90%, at least 95% or at least 100% of the antimicrobial activity of SEQ ID NO: 29 against *Clostridium perfringens* under the conditions 50% MHB, pH 6. Antimicrobial activity towards *Clostridium perfringens* can be determined according to the antimicrobial assay described in Example 4.

In a further preferred embodiment, the animal is a monogastric animal selected from the group consisting of swine (including, but not limited to, pigs, piglets, growing pigs, and sows) and poultry (including, but not limited to turkeys, ducks, chicken, broilers, chicks and layers).

Treatment of *Clostridium perfringens* Infections

In a third aspect, the invention relates to the animal feed additive or animal feed of the first aspect of the invention for use in the treatment of a *Clostridium perfringens* infection.

Thus the invention in particular relates to an animal feed or animal feed additive comprising one or more polypeptides having phytase activity and one or more polypeptides having lysozyme activity, wherein:
  (a) the polypeptide having lysozyme activity is from glycosyl hydrolyase family 25 and is obtained or obtainable from the kingdom Fungi; and
  (b) the polypeptide having phytase activity is classified as an EC 3.1.3.26 phytase (4-phytase)
for use in the treatment of a *Clostridium perfringens* infection.

Uses of Improving Animal Performance

In a forth aspect, the invention relates to the use of the animal feed additive or the animal feed of the first aspect of the invention for improving the European Production Efficiency Factor (EPEF) and/or Feed Conversion Ratio (FCR) in one or more animals.

Thus the invention in particular relates to the use of an animal feed additive or animal feed comprising one or more polypeptides having phytase activity and one or more polypeptides having lysozyme activity for improving the European Production Efficiency Factor (EPEF) and/or the Feed Conversion Ratio (FCR) in an animal, wherein
  (a) the polypeptide having lysozyme activity is from glycosyl hydrolyase family 25 and is obtained or obtainable from the kingdom Fungi; and
  (b) the polypeptide having phytase activity is classified as an EC 3.1.3.26 phytase (4-phytase).

In a preferred embodiment, the improvement is compared to the same feed but excluding the lysozyme.

In a preferred embodiment, the invention relates to the use of an animal feed additive or animal feed comprising one or more polypeptides having phytase activity and one or more polypeptides having lysozyme activity for improving the European Production Efficiency Factor (EPEF) and Feed Conversion Ratio (FCR) in an animal, wherein:
  (a) the polypeptide having lysozyme activity is selected from the group consisting of:
    (i) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27;
    (ii) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29;
    (iii) a variant of SEQ ID NO: 27 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
    (iv) a variant of SEQ ID NO: 29 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
    (v) a fragment of the polypeptide of (i) or (iii) that has lysozyme activity wherein the fragment comprises at least 170 amino acids, such as at least 175 amino acids, at least 180 amino acids, at least 185 amino acids, at least 190 amino acids, at least 195 amino acids or at least 200 amino acids; and
    (vi) a fragment of the polypeptide of (ii) or (iv) that has lysozyme activity wherein the fragment comprises at least 180 amino acids, such as at least 185 amino acids, at least 190 amino acids, at least 195 amino acids, at least 200 amino acids, at least 205 amino acids or at least 210 amino acids; and
  (b) the polypeptide having phytase activity is selected from the group consisting of:
    (i) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
    (ii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;

(iii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9;

(iv) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10;

(v) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 11;

(vi) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12;

(vii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;

(viii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 17;

(ix) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18;

(x) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21;

(xi) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 22;

(xii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 23;

(xiii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 25;

(xiv) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 26;

(xv) a variant of SEQ ID NO: 1, SEQ ID NO: 4, SEQ ID NO: 9, SEQ ID NO: 10, SEQ ID NO: 11, SEQ ID NO: 12, SEQ ID NO: 15, SEQ ID NO: 17, SEQ ID NO: 18, SEQ ID NO: 21, SEQ ID NO: 22, SEQ ID NO: 23, SEQ ID NO: 25 or SEQ ID NO: 26 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and (xvi) a fragment of the polypeptide of (i), (ii), (iii), (iv), (v), (vi), (vii), (viii), (ix), (x), (xi), (xii), (xiii), (xiv) or (xv) that has phytase activity wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids; and (c) the European Production Efficiency Factor (EPEF) is improved by at least 1% and the Feed Conversion Ratio (FCR) is improved by at least 1% compared to the same feed but excluding the lysozyme.

In one embodiment, the EPEF is improved by at least 1%, such as by at least 1.5%, at least 2.0%, at least 2.5%, at least 3%, at least 3.5%, at least 4% or at least 5%. In another embodiment, the EPEF is improved by between 1% and 15%, such as between 1% and 12%, between 1% and 10%, 1.5% and 8%, 2.0% and 7%, or any combination of these intervals.

In one embodiment, the FCR is improved by at least 1%, such as by at least 1.25%, at least 1.5% or at least 1.75%. In another embodiment, the FCR is improved by between 1% and 5%, such as between 1% and 4%, between 1% and 3%, 1.25% and 2.5%, 1.5% and 2%, or any combination of these intervals.

In one embodiment, the polypeptide having phytase activity is dosed at a level of 50 to 10000 FYT per kg animal feed, such as 100 to 6000 FYT per kg, 200 to 4000 FYT per kg, 250 to 3000 FYT per kg, 300 to 2500 FYT per kg, 350 to 2000 FYT per kg or 400 to 2000 FYT per kg animal feed, or any combination of these intervals (1 FYT=1 FTU=1U).

In one embodiment, the polypeptide having lysozyme activity is dosed at a level of 0.1 to 150 ppm enzyme protein per kg animal feed, such as 0.1 to 150 ppm, 0.5 to 100 ppm, 1 to 75 ppm, 2 to 50 ppm, 3 to 25 ppm, 2 to 80 ppm, 5 to 60 ppm, 8 to 40 ppm, 10 to 30 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the animal is any animal except humans. Examples of animals are non-ruminants, and ruminants. Ruminant animals include, for example, animals such as sheep, goats, cattle, e.g. beef cattle, cows, and young calves, deer, yank, camel, llama and kangaroo. Non-ruminant animals are preferred and include monogastric animals, such as pigs or swine (including, but not limited to, piglets, growing pigs, and sows); poultry such as turkeys, ducks, quail, guinea fowl, geese, pigeons (including squabs) and chicken (including but not limited to broiler chicks, layers); horses (including but not limited to hotbloods, coldbloods and warm bloods); crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish). In a preferred embodiment, the animal is a monogastric animal. In a more preferred embodiment, the animal is selected from the group consisting of swine, poultry, crustaceans and fish. In an even more preferred embodiment, the animal is selected from the group consisting of swine, piglet, growing pig, sow, chicken, broiler, layer, pullet and chick.

In one embodiment, the polypeptide having lysozyme activity has antimicrobial activity towards *Clostridium perfringens*. In an embodiment, the polypeptide having lysozyme activity has at least 60%, at least 70%, at least 80%, at least 85%, at least 90%, at least 95% or at least 100% of the antimicrobial activity of SEQ ID NO: 27 against *Clostridium perfringens* under the conditions 50% MHB, pH 6. In an embodiment, the polypeptide having lysozyme activity has at least 60%, at least 70%, at least 80%, at least 85%, at least 90%, at least 95% or at least 100% of the antimicrobial activity of SEQ ID NO: 29 against *Clostridium perfringens* under the conditions 50% MHB, pH 6. Antimicrobial activity towards *Clostridium perfringens* can be determined according to the antimicrobial assay described in Example 4.

Methods of Altering the Population of Bacteria in the GI Tract of an Animal

In a fifth aspect, the invention relates to a method of increasing the population of bacteria of the genus *Faecalibacterium* in the microbiota of the GI tract of an animal.

Thus the invention in particular relates to a method of increasing the population of bacteria of the genus *Faecalibacterium* in the microbiota of the GI tract of an animal, comprising administering to the animal an animal feed or animal feed additive comprising one or more polypeptides having phytase activity and one or more polypeptides having lysozyme activity, wherein:
 (a) the polypeptide having lysozyme activity is from glycosyl hydrolyase family 25; and
 (b) the animal feed or animal feed additive improves the European Production Efficiency Factor (EPEF) and/or Feed Conversion Ratio (FCR) of an animal, compared to an animal feed the same feed but excluding the lysozyme.

The invention further relates to a method of increasing the population of bacteria of the genus *Faecalibacterium* in the microbiota of the GI tract of an animal, comprising administering to the animal the animal feed or animal feed additive comprising one or more polypeptides having phytase activity and one or more polypeptides having lysozyme activity, wherein:
 (a) the polypeptide having lysozyme activity is from glycosyl hydrolyase family 25 and is obtained or obtainable from the kingdom Fungi; and
 (b) the polypeptide having phytase activity is classified as an EC 3.1.3.26 phytase (4-phytase).

The invention further relates to a method of increasing the population of bacteria of the genus *Faecalibacterium* in the microbiota of the GI tract of an animal, comprising administering to the animal the animal feed or animal feed additive comprising one or more polypeptides having phytase activity and one or more polypeptides having lysozyme activity, wherein:
 (a) the polypeptide having lysozyme activity is from glycosyl hydrolyase family 25 and is obtained or obtainable from the kingdom Fungi;
 (b) the polypeptide having phytase activity is classified as an EC 3.1.3.26 phytase (4-phytase); and
 (c) the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 33

In a preferred embodiment, the increased in the population of bacteria of the genus *Faecalibacterium* in the microbiota of the GI tract of an animal is compared to an animal administered the same feed but excluding the lysozyme.

In one embodiment, the proportion of bacteria of genus *Faecalibacterium* is increased by at least 1%, such as at least 2%, at least 5%, at least 10%, at least 15% or at least 20%.

In one embodiment, the proportion of bacteria of genus *Faecalibacterium* is increased by a factor of at least 1.25, such as at least 1.50, at least 1.75, at least 2.0, at least 2.5 or at least 3.0.

In one embodiment, the EPEF is improved by at least 1%, such as by at least 1.5%, at least 2.0%, at least 2.5%, at least 3%, at least 3.5%, at least 4% or at least 5%. In another embodiment, the EPEF is improved by between 1% and 15%, such as between 1% and 12%, between 1% and 10%, 1.5% and 8%, 2.0% and 7%, or any combination of these intervals.

In one embodiment, the FCR is improved by at least 1%, such as by at least 1.25%, at least 1.5% or at least 1.75%. In another embodiment, the FCR is improved by between 1% and 5%, such as between 1% and 4%, between 1% and 3%, 1.25% and 2.5%, 1.5% and 2%, or any combination of these intervals.

In one embodiment, the method improves the European Production Efficiency Factor (EPEF) of an animal by at least 1% and increases the proportion of bacteria of genus *Faecalibacterium* in the microbiota of the GI tract of an animal. In an embodiment, the proportion of bacteria of genus *Faecalibacterium* is increased by at least 1%, such as at least 2%, at least 5%, at least 10%, at least 15% or at least 20% and the EPEF is increased by at least 1.5%, preferably by at least 2.0%, at least 2.5%, at least 3%, at least 3.5%, at least 4% or most preferably by at least 5%.

In one embodiment, the method improves the European Production Efficiency Factor (EPEF) of an animal by at least 1% and increases the proportion of bacteria of genus *Faecalibacterium* in the microbiota of the GI tract of an animal. In an embodiment, the proportion of bacteria of genus *Faecalibacterium* is increased by factor of at least 1.25, such as at least 1.50, at least 1.75, at least 2.0, at least 2.5 or at least 3.0 and the EPEF is increased by at least 1.5%, preferably by at least 2.0%, at least 2.5%, at least 3%, at least 3.5%, at least 4% or most preferably by at least 5%.

In one embodiment, the method improves the Feed Conversion Ratio (FCR) of an animal by at least 1% and increases the proportion of bacteria of genus *Faecalibacterium* in the microbiota of the GI tract of an animal. In an embodiment, the proportion of bacteria of genus *Faecalibacterium* is increased by at least 1%, such as at least 2%, at least 5%, at least 10%, at least 15% or at least 20% and the FCR is increased by at least 1.5%, preferably by at least 1.25%, preferably by at least 1.5% or most preferably by at least 1.75%.

In one embodiment, the method improves the Feed Conversion Ratio (FCR) of an animal by at least 1% and increases the proportion of bacteria of genus *Faecalibacterium* in the microbiota of the GI tract of an animal. In an embodiment, the proportion of bacteria of genus *Faecalibacterium* is increased by factor of at least 1.25, such as at least 1.50, at least 1.75, at least 2.0, at least 2.5 or at least 3.0 and the FCR is increased by at least 1.25%, preferably by at least 1.5% or most preferably by at least 1.75%.

The invention further relates to a method of increasing the population of bacteria of the order Clostridiales in the microbiota of the GI tract of an animal, comprising administering to the animal an animal feed or animal feed additive comprising one or more polypeptides having phytase activity and one or more polypeptides having lysozyme activity, wherein:
  (a) the polypeptide having lysozyme activity is from glycosyl hydrolyase family 25; and
  (b) the animal feed or animal feed additive improves the European Production Efficiency Factor (EPEF) and/or Feed Conversion Ratio (FCR) of an animal, compared to an animal feed the same feed but excluding the lysozyme.

The invention further relates to a method of increasing the population of bacteria of the order Clostridiales in the microbiota of the GI tract of an animal, comprising administering to the animal the animal feed or animal feed additive comprising one or more polypeptides having phytase activity and one or more polypeptides having lysozyme activity, wherein:
  (a) the polypeptide having lysozyme activity is from glycosyl hydrolyase family 25 and is obtained or obtainable from the kingdom Fungi; and
  (b) the polypeptide having phytase activity is classified as an EC 3.1.3.26 phytase (4-phytase).

In a preferred embodiment, the increased in the population of bacteria of the order Clostridiales in the microbiota of the GI tract of an animal is compared to an animal administered the same feed but excluding the lysozyme.

In one embodiment, the proportion of bacteria of order Clostridiales is increased by at least 1%, such as at least 1.5%, at least 2%, at least 2.5%, at least 5% or at least 7.5%.

In one embodiment, the proportion of bacteria of order Clostridiales is increased by a factor of at least 1.025, such as at least 1.05, at least 1.075, at least 1.1, at least 1.15 or at least 1.2.

In one embodiment, the EPEF is improved by at least 1%, such as by at least 1.5%, at least 2.0%, at least 2.5%, at least 3%, at least 3.5%, at least 4% or at least 5%. In another embodiment, the EPEF is improved by between 1% and 15%, such as between 1% and 12%, between 1% and 10%, 1.5% and 8%, 2.0% and 7%, or any combination of these intervals.

In one embodiment, the FCR is improved by at least 1%, such as by at least 1.25%, at least 1.5% or at least 1.75%. In another embodiment, the FCR is improved by between 1% and 5%, such as between 1% and 4%, between 1% and 3%, 1.25% and 2.5%, 1.5% and 2%, or any combination of these intervals.

In one embodiment, the method improves the European Production Efficiency Factor (EPEF) of an animal by at least 1% and increases the proportion of bacteria of order Clostridiales in the microbiota of the GI tract of an animal. In an embodiment, the proportion of bacteria of order Clostridiales is increased by at least 1%, such as at least 1.5%, at least 2%, at least 2.5%, at least 5% or at least 7.5% and the EPEF is increased by at least 1.5%, preferably by at least 2.0%, at least 2.5%, at least 3%, at least 3.5%, at least 4% or most preferably by at least 5%.

In one embodiment, the method improves the European Production Efficiency Factor (EPEF) of an animal by at least 1% and increases the proportion of bacteria of order Clostridiales in the microbiota of the GI tract of an animal. In an embodiment, the proportion of bacteria of order Clostridiales is increased by factor of at least 1.025, such as at least 1.05, at least 1.075, at least 1.1, at least 1.15 or at least 1.2 and the EPEF is increased by at least 1.5%, preferably by at least 2.0%, at least 2.5%, at least 3%, at least 3.5%, at least 4% or most preferably by at least 5%.

In one embodiment, the method improves the Feed Conversion Ratio (FCR) of an animal by at least 1% and increases the proportion of bacteria of order Clostridiales in the microbiota of the GI tract of an animal. In an embodiment, the proportion of bacteria of order Clostridiales is increased by at least 1%, such as at least 1.5%, at least 2%, at least 2.5%, at least 5% or at least 7.5% and the FCR is increased by at least 1.5%, preferably by at least 1.25%, preferably by at least 1.5% or most preferably by at least 1.75%.

In one embodiment, the method improves the Feed Conversion Ratio (FCR) of an animal by at least 1% and increases the proportion of bacteria of order Clostridiales in the microbiota of the GI tract of an animal. In an embodiment, the proportion of bacteria of order Clostridiales is increased by factor of at least 1.025, such as at least 1.05, at least 1.075, at least 1.1, at least 1.15 or at least 1.2 and the FCR is increased by at least 1.25%, preferably by at least 1.5% or most preferably by at least 1.75%.

In an embodiment, the polypeptide having lysozyme activity is selected from the group consisting of:
  (i) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27;
  (ii) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29;
  (iii) a variant of SEQ ID NO: 27 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
  (iv) a variant of SEQ ID NO: 29 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(v) a fragment of the polypeptide of (i) or (iii) that has lysozyme activity wherein the fragment comprises at least 170 amino acids, such as at least 175 amino acids, at least 180 amino acids, at least 185 amino acids, at least 190 amino acids, at least 195 amino acids or at least 200 amino acids; and (vi) a fragment of the polypeptide of (ii) or (iv) that has lysozyme activity wherein the fragment comprises at least 180 amino acids, such as at least 185 amino acids, at least 190 amino acids, at least 195 amino acids, at least 200 amino acids, at least 205 amino acids or at least 210 amino acids;

and the polypeptide having phytase activity is selected from the group consisting of:

(i) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;

(ii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;

(iii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9;

(iv) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10;

(v) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 11;

(vi) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12;

(vii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;

(viii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 17;

(ix) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18;

(x) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21;

(xi) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 22;

(xii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 23;

(xiii) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 25;

(xiv) a polypeptide having at least 70%, e.g., at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 26;

(xv) a variant of SEQ ID NO: 1, SEQ ID NO: 4, SEQ ID NO: 9, SEQ ID NO: 10, SEQ ID NO: 11, SEQ ID NO: 12, SEQ ID NO: 15, SEQ ID NO: 17, SEQ ID NO: 18, SEQ ID NO: 21, SEQ ID NO: 22, SEQ ID NO: 23, SEQ ID NO: 25 or SEQ ID NO: 26 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and (xvi) a fragment of the polypeptide of (i), (ii), (iii), (iv), (v), (vi), (vii), (viii), (ix), (x), (xi), (xii), (xiii), (xiv) or (xv) that has phytase activity wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids; and (c) the European Production Efficiency Factor (EPEF) is improved by at least 1% and the Feed Conversion Ratio (FCR) is improved by at least 1% compared to the same feed but excluding the lysozyme.

In one embodiment, the polypeptide having phytase activity is dosed at a level of 50 to 10000 FYT per kg animal feed, such as 100 to 6000 FYT per kg, 200 to 4000 FYT per kg, 250 to 3000 FYT per kg, 300 to 2500 FYT per kg, 350 to 2000 FYT per kg or 400 to 2000 FYT per kg animal feed, or any combination of these intervals (1 FYT=1 FTU=1U).

In one embodiment, the polypeptide having lysozyme activity is dosed at a level of 0.1 to 150 ppm enzyme protein per kg animal feed, such as 0.1 to 150 ppm, 0.5 to 100 ppm, 1 to 75 ppm, 2 to 50 ppm, 3 to 25 ppm, 2 to 80 ppm, 5 to 60 ppm, 8 to 40 ppm, 10 to 30 ppm, 13 to 75 ppm, 15 to 50 ppm, 17.5 to 40 ppm, 25 to 75 ppm or 30 to 60 ppm enzyme protein per kg animal feed, or any combination of these intervals.

In one embodiment, the animal is any animal except humans. Examples of animals are non-ruminants, and ruminants. Ruminant animals include, for example, animals such as sheep, goats, cattle, e.g. beef cattle, cows, and young calves, deer, yank, camel, llama and kangaroo. Non-ruminant animals are preferred and include monogastric animals, such as pigs or swine (including, but not limited to, piglets, growing pigs, and sows); poultry such as turkeys, ducks, quail, guinea fowl, geese, pigeons (including squabs) and chicken (including but not limited to broiler chicks, layers); horses (including but not limited to hotbloods, coldbloods and warm bloods); crustaceans (including but not limited to shrimps and prawns) and fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish). In a preferred embodiment, the animal is a monogastric animal. In a more preferred embodiment, the animal is selected from the group consisting of swine, poultry, crustaceans and fish. In an even more preferred embodiment, the animal is selected from the group consisting of swine, piglet, growing pig, sow, chicken, broiler, layer, pullet and chick.

In one embodiment, the polypeptide having lysozyme activity has antimicrobial activity towards *Clostridium perfringens*. In an embodiment, the polypeptide having lysozyme activity has at least 60%, at least 70%, at least 80%, at least 85%, at least 90%, at least 95% or at least 100% of the antimicrobial activity of SEQ ID NO: 27 against *Clostridium perfringens* under the conditions 50% MHB, pH 6. In an embodiment, the polypeptide having lysozyme activity has at least 60%, at least 70%, at least 80%, at least 85%, at least 90%, at least 95% or at least 100% of the antimicrobial activity of SEQ ID NO: 29 against *Clostridium perfringens* under the conditions 50% MHB, pH 6. Antimicrobial activity towards *Clostridium perfringens* can be determined according to the antimicrobial assay described in Example 4.

Preferred Embodiments

1. An animal feed or animal feed additive comprising one or more polypeptides having phytase activity and one or more polypeptides having lysozyme activity, wherein:
   (a) the polypeptide having lysozyme activity is from glycosyl hydrolase family 25 and is obtained or obtainable from the kingdom Fungi; and
   (b) the polypeptide having phytase activity is classified as an EC 3.1.3.26 phytase (4-phytase).
2. The animal feed or animal feed additive of item 1, wherein the animal feed or animal feed additive improves the European Production Efficiency Factor (EPEF) of an animal by at least 1%, preferably by at least 1.5%, at least 2.0%, at least 2.5%, at least 3%, at least 3.5%, at least 4% or most preferably by at least 5%.
3. The animal feed or animal feed additive of any of items 1 to 2, wherein the animal feed or animal feed additive improves the Feed Conversion Ratio (FCR) of an animal by at least 1%, preferably by at least 1.25%, at least 1.5% or most preferably by at least 1.75%.
4. The animal feed or animal feed additive of any of items 2 to 3 wherein the European Production Efficiency Factor (EPEF) and/or Feed Conversion Ratio (FCR) of an animal is improved compared to an animal feed the same feed but excluding the lysozyme.
5. The animal feed or animal feed additive of any of items 1 to 4, wherein the animal feed or animal feed additive increases the proportion of bacteria of genus *Faecalibacterium* in the microbiota of the GI tract of an animal.
6. The animal feed or animal feed additive of item 5, wherein the proportion of bacteria of genus *Faecalibacterium* is increased by at least 1%, such as at least 2%, at least 5%, at least 10%, at least 15% or at least 20%.
7. The animal feed or animal feed additive of item 5, wherein the proportion of bacteria of genus *Faecalibacterium* is increased by a factor of at least 1.25, such as at least 1.50, at least 1.75, at least 2.0, at least 2.5 or at least 3.0.
8. The animal feed or animal feed additive of item 1, wherein the animal feed or animal feed additive improves the European Production Efficiency Factor (EPEF) and/or Feed Conversion Ratio (FCR) of an animal by at least 1% and increases the proportion of bacteria of genus *Faecalibacterium* in the microbiota of the GI tract of an animal.
9. The animal feed or animal feed additive of item 8, wherein the proportion of bacteria of genus *Faecalibacterium* is increased by at least 1%, such as at least 2%, at least 5%, at least 10%, at least 15% or at least 20%.
10. The animal feed or animal feed additive of item 8, wherein the proportion of bacteria of genus *Faecalibacterium* is increased by a factor of at least 1.25, such as at least 1.50, at least 1.75, at least 2.0, at least 2.5 or at least 3.0.
11. The animal feed or animal feed additive of any of items 1 to 4, wherein the animal feed or animal feed additive increases the proportion of bacteria of order Clostridiales in the microbiota of the GI tract of an animal.
12. The animal feed or animal feed additive of item 11, wherein the proportion of bacteria of order Clostridiales is increased by at least 1%, such as at least 1.5%, at least 2%, at least 2.5%, at least 5% or at least 7.5%.
13. The animal feed or animal feed additive of item 11, wherein the proportion of bacteria of order Clostridiales is increased by a factor of at least 1.025, such as at least 1.05, at least 1.075, at least 1.1, at least 1.15 or at least 1.2.
14. The animal feed or animal feed additive of item 1, wherein the animal feed or animal feed additive improves the European Production Efficiency Factor (EPEF) and/or Feed Conversion Ratio (FCR) of an animal by at least 1% and increases the proportion of bacteria of order Clostridiales in the microbiota of the GI tract of an animal.
15. The animal feed or animal feed additive of item 14, wherein the proportion of bacteria of order Clostridiales is increased by at least 1%, such as at least 1.5%, at least 2%, at least 2.5%, at least 5% or at least 7.5%.
16. The animal feed or animal feed additive of item 14, wherein the proportion of bacteria of order Clostridiales is increased by a factor of at least 1.025, such as at least 1.05, at least 1.075, at least 1.1, at least 1.15 or at least 1.2.
17. The animal feed or animal feed additive of any of items 5 to 16, wherein the animal feed or animal feed additive improves the European Production Efficiency Factor (EPEF) of an animal by at least 1.5%, preferably by at least 2.0%, at least 2.5%, at least 3%, at least 3.5%, at least 4% or most preferably by at least 5%.

18. The animal feed or animal feed additive of any of items 5 to 16, wherein the animal feed or animal feed additive improves the Feed Conversion Ratio (FCR) of an animal by at least 1.25%, preferably by at least 1.5% or most preferably by at least 1.75%.

19. The animal feed or animal feed additive of any of items 17 to 18 wherein the European Production Efficiency Factor (EPEF) and/or Feed Conversion Ratio (FCR) of an animal is improved compared to an animal feed the same feed but excluding the lysozyme.

20. The animal feed or animal feed additive of any of items 1 to 19, wherein the polypeptide having phytase activity is dosed at a level of 50 to 10000 FYT per kg animal feed.

21. The animal feed or animal feed additive of any of items 1 to 20, wherein the polypeptide having lysozyme activity is dosed at a level of 0.1-150 ppm enzyme protein per kg animal feed.

22. The animal feed or animal feed additive of any of items 1 to 21, wherein the polypeptide having lysozyme activity has antimicrobial activity toward *Clostridium perfringens*.

23. The animal feed or animal feed additive of any of items 1 to 22, wherein the polypeptide having lysozyme activity is obtained or obtainable from the phylum Ascomycota.

24. The animal feed or animal feed additive of any of items 1 to 23, wherein the polypeptide having lysozyme activity is obtained or obtainable from the class Eurotiomycetes.

25. The animal feed or animal feed additive of any of items 1 to 24, wherein the polypeptide having lysozyme activity is selected from the group consisting of:
   (a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27;
   (b) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29;
   (c) a variant of SEQ ID NO: 27 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
   (d) a variant of SEQ ID NO: 29 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (e) a fragment of the polypeptide of (a) or (c) that has lysozyme activity wherein the fragment comprises at least 170 amino acids, such as at least 175 amino acids, at least 180 amino acids, at least 185 amino acids, at least 190 amino acids, at least 195 amino acids or at least 200 amino acids; and
   (f) a fragment of the polypeptide of (b) or (d) that has lysozyme activity wherein the fragment comprises at least 180 amino acids, such as at least 185 amino acids, at least 190 amino acids, at least 195 amino acids, at least 200 amino acids, at least 205 amino acids or at least 210 amino acids.

26. The animal feed or animal feed additive of item 25, wherein the polypeptide having lysozyme activity comprises or consists of amino acids 1 to 213 of SEQ ID NO: 27, amino acids 1 to 218 of SEQ ID NO: 29 or amino acids 1 to 208 of SEQ ID NO: 30.

27. The animal feed or animal feed additive of any of items 1 to 26, wherein the polypeptide having phytase activity is of bacterial origin.

28. The animal feed or animal feed additive of any of items 1 to 27, wherein the polypeptide having phytase activity is obtained or obtainable from the family Enterobacteriaceae.

29. The animal feed or animal feed additive of any of items 1 to 28, wherein the polypeptide having phytase activity is obtained or obtainable from *Citrobacter* sp., *Buttiauxella* sp., *Hafnia* sp or *Escherichia* sp.

30. The animal feed or animal feed additive of any of items 1 to 29, wherein the polypeptide having phytase activity is selected from the group consisting of:
   (a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
   (b) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;
   (c) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9;
   (d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10;
   (e) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 11;
   (f) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12;

(g) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;

(h) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 17;

(i) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18;

(j) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21;

(k) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 22;

(l) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 23;

(m) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 25;

(n) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 26;

(o) a variant of SEQ ID NO: 1, SEQ ID NO: 4, SEQ ID NO: 9, SEQ ID NO: 10, SEQ ID NO: 11, SEQ ID NO: 12, SEQ ID NO: 15, SEQ ID NO: 17, SEQ ID NO: 18, SEQ ID NO: 21, SEQ ID NO: 22, SEQ ID NO: 23, SEQ ID NO: 25 or SEQ ID NO: 26 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and (p) a fragment of the polypeptide of (a), (b), (c), (d), (e), (f), (g), (h), (i), (j), (k), (l), (m), (n) or (o) that has phytase activity wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids.

31. The animal feed or animal feed additive of any of items 1 to 30 which further comprises one or more components selected from the list consisting of:
one or more carriers;
one or more additional enzymes;
one or more microbes;
one or more vitamins;
one or more minerals;
one or more amino acids; and
one or more other feed ingredients.

32. The animal feed or animal feed additive of item 31, wherein the one or more carriers is selected from the group consisting of water, glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, kaolin and cellulose or any combination thereof.

33. The animal feed or animal feed additive of item 31, wherein the one or more additional enzymes is selected from the group consisting of xylanase, galactanase, alpha-galactosidase, beta-galactosidase, protease, phospholipase A1, phospholipase A2, lysophospholipase, phospholipase C, phospholipase D, amylase, arabinofuranosidase, beta-xylosidase, acetyl xylan esterase, feruloyl esterase, cellulase, cellobiohydrolases, beta-glucosidase, pullulanase, mannosidase, mannanase and beta-glucanase or any combination thereof.

34. The animal feed or animal feed additive of item 31, wherein the one or more microbes is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

35. The animal feed or animal feed additive of any of items 1 to 34, wherein the polypeptide having phytase activity is in granulate form, the polypeptide having lysozyme activity is in granulate form or both the polypeptide having phytase activity and the polypeptide having lysozyme activity are in granulate form.

36. The animal feed or animal feed additive of item 35, wherein the granulate is coated.

37. The animal feed or animal feed additive of item 36 wherein the coating comprises a salt and/or wax and/or a flour.

38. The animal feed of any of items 1 to 37, wherein the polypeptide having phytase activity is in a liquid formulation and/or the polypeptide having lysozyme activity is in a liquid formulation.
39. The animal feed of item 38, wherein the liquid formulation is sprayed onto the feed after it has been pelleted.
40. The animal feed or animal feed additive of any of items 1 to 39, wherein the animal feed or animal feed additive is administered to a non-ruminant animal, preferably a monogastric animal, more preferably selected from the group consisting of swine, piglet, growing pig, sow, poultry, turkey, duck, quail, guinea fowl, goose, pigeon, squab, chicken, broiler, layer, pullet and chick, horse, crustaceans, shrimps, prawns, fish, amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish or even more preferably selected from the group consisting of swine, piglet, growing pig, sow, chicken, broiler, layer, pullet and chick.
41. The animal feed or animal feed additive of any of items 1 to 40, wherein the animal feed or animal feed additive comprises at least one protein or protein source.
42. The animal feed or animal feed additive of item 41, wherein the protein or protein source is vegetable protein, such as soybean, lupine, pea, bean, beet, sugar beet, spinach, *quinoa*, rapeseed, cabbage or any combination thereof.
43. A pelleted animal feed comprising plant based material and the animal feed or animal feed additive of any of items 1 to 42.
44. The pelleted animal feed of item 43, wherein the plant based material comprises oats, rye, barley, wheat, maize, corn, sorghum, switchgrass, millet, pearl millet, foxtail millet, soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea, in a processed form thereof or any combination thereof.
45. A method of improving one or more performance parameters in an animal comprising administering to one or more animals an animal feed or animal feed additive comprising one or more polypeptides having phytase activity and one or more polypeptides having lysozyme activity, wherein:
 (a) the polypeptide having lysozyme activity is from glycosyl hydrolyase family 25; and
 (b) the one or more performance parameters is selected from the group consisting of the European Production Efficiency Factor (EPEF) and Feed Conversion Ratio (FCR).
46. A method of improving one or more performance parameters in an animal comprising administering to one or more animals an animal feed or animal feed additive comprising one or more polypeptides having phytase activity and one or more polypeptides having lysozyme activity, wherein:
 (a) the polypeptide having lysozyme activity is from glycosyl hydrolyase family 25 and is obtained or obtainable from the kingdom Fungi;
 (b) the polypeptide having phytase activity is classified as an EC 3.1.3.26 phytase (4-phytase); and
 (c) the one or more performance parameters is selected from the group consisting of the European Production Efficiency Factor (EPEF) and Feed Conversion Ratio (FCR).
47. The method of any of items 45 to 46, wherein the EPEF is improved by at least 1%, preferably by at least 1.5%, at least 2.0%, at least 2.5%, at least 3%, at least 3.5%, at least 4% or most preferably by at least 5%.
48. The method of any of items 45 to 47, wherein the FCR is improved by at least 1%, preferably by at least 1.25%, at least 1.5% or most preferably by at least 1.75%.
49. The method of any of items 45 to 48, wherein the European Production Efficiency Factor (EPEF) and/or Feed Conversion Ratio (FCR) of an animal is improved compared to an animal feed the same feed but excluding the lysozyme.
50. The method of any of items 45 to 49, wherein the animal feed or animal feed additive increases the proportion of bacteria of genus *Faecalibacterium* in the microbiota of the GI tract of an animal.
51. The method of item 50, wherein the proportion of bacteria of genus *Faecalibacterium* is increased by at least 1%, such as at least 2%, at least 5%, at least 10%, at least 15% or at least 20%.
52. The method of item 50, wherein the proportion of bacteria of genus *Faecalibacterium* is increased by a factor of at least 1.25, such as at least 1.50, at least 1.75, at least 2.0, at least 2.5 or at least 3.0.
53. The method of any of items 45 to 49, wherein the animal feed or animal feed additive improves the European Production Efficiency Factor (EPEF) and/or Feed Conversion Ratio (FCR) of an animal by at least 1% and increases the proportion of bacteria of genus *Faecalibacterium* in the microbiota of the GI tract of an animal.
54. The method of item 53, wherein the proportion of bacteria of genus *Faecalibacterium* is increased by at least 1%, such as at least 2%, at least 5%, at least 10%, at least 15% or at least 20%.
55. The method of item 53, wherein the proportion of bacteria of genus *Faecalibacterium* is increased by a factor of at least 1.25, such as at least 1.50, at least 1.75, at least 2.0, at least 2.5 or at least 3.0.
56. The method of any of items 45 to 49, wherein the animal feed or animal feed additive increases the proportion of bacteria of order Clostridiales in the microbiota of the GI tract of an animal.
57. The method of item 56, wherein the proportion of bacteria of order Clostridiales is increased by at least 1%, such as at least 1.5%, at least 2%, at least 2.5%, at least 5% or at least 7.5%.
58. The method of item 56, wherein the proportion of bacteria of order Clostridiales is increased by a factor of at least 1.025, such as at least 1.05, at least 1.075, at least 1.1, at least 1.15 or at least 1.2.
59. The method of any of items 45 to 49, wherein the animal feed or animal feed additive improves the European Production Efficiency Factor (EPEF) and/or Feed Conversion Ratio (FCR) of an animal by at least 1% and increases the proportion of bacteria of order Clostridiales in the microbiota of the GI tract of an animal.
60. The method of item 59, wherein the proportion of bacteria of order Clostridiales is increased by at least 1%, such as at least 1.5%, at least 2%, at least 2.5%, at least 5% or at least 7.5%.

61. The method of item 59, wherein the proportion of bacteria of order Clostridiales is increased by a factor of at least 1.025, such as at least 1.05, at least 1.075, at least 1.1, at least 1.15 or at least 1.2.

62. The method of any of items 45 to 49, wherein the animal feed or animal feed additive improves the European Production Efficiency Factor (EPEF) of an animal by at least 1.5%, preferably by at least 2.0%, at least 2.5%, at least 3%, at least 3.5%, at least 4% or most preferably by at least 5%.

63. The method of item 62, wherein the animal feed or animal feed additive improves the Feed Conversion Ratio (FCR) of an animal by at least 1.25%, preferably by at least 1.5% or most preferably by at least 1.75%.

64. The method of item 62, wherein the European Production Efficiency Factor (EPEF) and/or Feed Conversion Ratio (FCR) of an animal is improved compared to an animal feed the same feed but excluding the lysozyme.

65. The method of any of items 45 to 64, wherein the polypeptide having phytase activity is dosed at a level of 50 to 10000 FYT per kg animal feed.

66. The method of any of items 45 to 65, wherein the polypeptide having lysozyme activity is dosed at a level of 0.1-150 ppm enzyme protein per kg animal feed.

67. The method of any of items 45 to 66, wherein the polypeptide having lysozyme activity has antimicrobial activity toward *Clostridium perfringens*.

68. The method of any of items 45 to 67, wherein the polypeptide having lysozyme activity is obtained or obtainable from the kingdom Fungi.

69. The method of any of items 45 to 68, wherein the polypeptide having lysozyme activity is obtained or obtainable from the phylum Ascomycota.

70. The method of any of items 45 to 69, wherein the polypeptide having lysozyme activity is obtained or obtainable from the class Eurotiomycetes.

71. The method of any of items 45 to 70, wherein the polypeptide having lysozyme activity is selected from the group consisting of:
   (a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 27;
   (b) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 29;
   (c) a variant of SEQ ID NO: 27 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and
   (d) a variant of SEQ ID NO: 29 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (e) a fragment of the polypeptide of (a) or (c) that has lysozyme activity wherein the fragment comprises at least 170 amino acids, such as at least 175 amino acids, at least 180 amino acids, at least 185 amino acids, at least 190 amino acids, at least 195 amino acids or at least 200 amino acids; and
   (f) a fragment of the polypeptide of (b) or (d) that has lysozyme activity wherein the fragment comprises at least 180 amino acids, such as at least 185 amino acids, at least 190 amino acids, at least 195 amino acids, at least 200 amino acids, at least 205 amino acids or at least 210 amino acids.

72. The method of any of items 45 to 71, wherein the polypeptide having phytase activity is a 4-phytase (EC 3.1.3.26).

73. The method of any of items 45 to 72, wherein the polypeptide having phytase activity is of bacterial origin.

74. The method of any of items 45 to 73, wherein the polypeptide having phytase activity is obtained or obtainable from the family Enterobacteriaceae.

75. The method of any of items 45 to 74, wherein the polypeptide having phytase activity is obtained or obtainable from *Citrobacter* sp., *Buttiauxella* sp., *Hafnia* sp or *Escherichia* sp.

76. The method of any of items 45 to 75, wherein the polypeptide having phytase activity is selected from the group consisting of:
   (a) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 1;
   (b) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 4;
   (c) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 9;
   (d) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 10;
   (e) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 11;
   (f) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 12;

(g) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 15;

(h) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 17;

(i) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 18;

(j) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 21;

(k) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 22;

(l) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 23;

(m) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 25;

(n) a polypeptide having at least 50%, e.g., at least 60%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to SEQ ID NO: 26;

(o) a variant of SEQ ID NO: 1, SEQ ID NO: 4, SEQ ID NO: 9, SEQ ID NO: 10, SEQ ID NO: 11, SEQ ID NO: 12, SEQ ID NO: 15, SEQ ID NO: 17, SEQ ID NO: 18, SEQ ID NO: 21, SEQ ID NO: 22, SEQ ID NO: 23, SEQ ID NO: 25 or SEQ ID NO: 26 comprising one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions; and (p) a fragment of the polypeptide of (a), (b), (c), (d), (e), (f), (g), (h), (i), (j), (k), (l), (m), (n) or (o) that has phytase activity wherein the fragment comprises at least 360 amino acids, such as at least 370 amino acids, at least 380 amino acids, at least 385 amino acids, at least 390 amino acids, at least 395 amino acids, at least 400 amino acids or at least 405 amino acids.

77. The method of any of items 45 to 76, wherein the animal feed or animal feed additive further comprises one or more components selected from the list consisting of:
one or more carriers;
one or more additional enzymes;
one or more microbes;
one or more vitamins;
one or more minerals;
one or more amino acids; and
one or more other feed ingredients.

78. The method of item 77, wherein the one or more carriers is selected from the group consisting of water, glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, kaolin and cellulose or any combination thereof.

79. The method of item 77, wherein the one or more additional enzymes is selected from the group consisting of xylanase, galactanase, alpha-galactosidase, beta-galactosidase, protease, phospholipase A1, phospholipase A2, lysophospholipase, phospholipase C, phospholipase D, amylase, arabinofuranosidase, beta-xylosidase, acetyl xylan esterase, feruloyl esterase, cellulase, cellobiohydrolases, beta-glucosidase, pullulanase, mannosidase, mannanase and beta-glucanase or any combination thereof.

80. The method of item 77, wherein the one or more microbes is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

81. The method of any of items 45 to 80, wherein the polypeptide having phytase activity is in granulate form, the polypeptide having lysozyme activity is in granulate form or both the polypeptide having phytase activity and the polypeptide having lysozyme activity are in granulate form.

82. The method of item 81, wherein the granulate is coated.

83. The method of item 82, wherein the coating comprises a salt and/or wax and/or a flour.

84. The method of any of items 45 to 83, wherein the polypeptide having phytase activity is in a liquid formulation and/or the polypeptide having lysozyme activity is in a liquid formulation.
85. The method of item 84, wherein the liquid formulation is sprayed onto the feed after it has been pelleted.
86. The method of any of items 45 to 85, wherein the animal is a non-ruminant animal, preferably a monogastric animal, more preferably selected from the group consisting of swine, piglet, growing pig, sow, poultry, turkey, duck, quail, guinea fowl, goose, pigeon, squab, chicken, broiler, layer, pullet and chick, horse, crustaceans, shrimps, prawns, fish, amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish or even more preferably selected from the group consisting of swine, piglet, growing pig, sow, chicken, broiler, layer, pullet and chick.
87. The method of any of items 45 to 86, wherein the animal feed or animal feed additive comprises at least one protein or protein source.
88. The method of item 87, wherein the protein or protein source is vegetable protein, such as soybean, lupine, pea, bean, beet, sugar beet, spinach, *quinoa*, rapeseed, cabbage or any combination thereof.
89. Use of the animal feed or animal feed additive of any of items 1 to 42 or the pelleted animal feed of any of items 43 to 44 for improving the European Production Efficiency Factor (EPEF) and/or Feed Conversion Ratio (FCR) in an animal.
90. A method of improving the European Production Efficiency Factor (EPEF) and/or Feed Conversion Ratio (FCR) of an animal comprising administering to the animal the animal feed or animal feed additive of any of items 1 to 42 or the pelleted animal feed of any of items 43 to 44.
91. The animal feed or animal feed additive of any of items 1 to 42 or the pelleted animal feed of any of items 43 to 44 for use in the treatment of a *Clostridium perfringens* infection.
92. A method of increasing the population of bacteria of the genus *Faecalibacterium* in the microbiota of the GI tract of an animal, comprising administering to the animal an animal feed or animal feed additive comprising one or more polypeptides having phytase activity and one or more polypeptides having lysozyme activity, wherein:
    (a) the polypeptide having lysozyme activity is from glycosyl hydrolyase family 25; and
    (b) the animal feed or animal feed additive improves the European Production Efficiency Factor (EPEF) and/or Feed Conversion Ratio (FCR) of an animal, compared to an animal feed the same feed but excluding the lysozyme.
93. A method of increasing the population of bacteria of the genus *Faecalibacterium* in the microbiota of the GI tract of an animal, comprising administering to the animal the animal feed or animal feed additive of any of items 1 to 42 or a pelleted animal feed thereof.
94. The method of any of items 92 to 93, wherein the proportion of bacteria of genus *Faecalibacterium* is increased by at least 1%, such as at least 2%, at least 5%, at least 10%, at least 15% or at least 20%.
95. The method of any of items 92 to 93, wherein the proportion of bacteria of genus *Faecalibacterium* is increased by a factor of at least 1.25, such as at least 1.50, at least 1.75, at least 2.0, at least 2.5 or at least 3.0.
96. A method of increasing the population of bacteria of the order Clostridiales in the microbiota of the GI tract of an animal, comprising administering to the animal an animal feed or animal feed additive comprising one or more polypeptides having phytase activity and one or more polypeptides having lysozyme activity, wherein:
    (a) the polypeptide having lysozyme activity is from glycosyl hydrolyase family 25; and
    (b) the animal feed or animal feed additive improves the European Production Efficiency Factor (EPEF) and/or Feed Conversion Ratio (FCR) of an animal, compared to an animal feed the same feed but excluding the lysozyme.
97. A method of increasing the population of bacteria of the order Clostridiales in the microbiota of the GI tract of an animal, comprising administering to the animal the animal feed or animal feed additive of any of items 1 to 42 or a pelleted animal feed thereof.
98. The method of any of items 96 to 97, wherein the proportion of bacteria of order Clostridiales is increased by at least 1%, such as at least 1.5%, at least 2%, at least 2.5%, at least 5% or at least 7.5%.
99. The method of any of items 96 to 97, wherein the proportion of bacteria of order Clostridiales is increased by a factor of at least 1.025, such as at least 1.05, at least 1.075, at least 1.1, at least 1.15 or at least 1.2.
100. The method of any of items 92 to 99, wherein the animal feed or animal feed additive improves the European Production Efficiency Factor (EPEF) of an animal by at least 1.5%, preferably by at least 2.0%, at least 2.5%, at least 3%, at least 3.5%, at least 4% or most preferably by at least 5%.
101. The method of any of items 92 to 100, wherein the animal feed or animal feed additive improves the Feed Conversion Ratio (FCR) of an animal by at least 1.25%, preferably by at least 1.5% or most preferably by at least 1.75%.
102. The animal feed or animal feed additive of any of items 4 to 10 or the method of any of items 50 to 55 or 92 to 95 wherein the proportion of bacteria of genus *Faecalibacterium* increases after treatment with an antibiotic.
103. The animal feed or animal feed additive of any of items 4 to 10 or the method of any of items 50 to 55 or 92 to 95, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to any of SEQ ID NO: 33 to 54.
104. The animal feed or animal feed additive of any of items 4 to 10 or the method of any of items 50 to 55 or 92 to 95, wherein the bacteria of genus *Faecalibacterium* comprise 16S rRNA that has at least 90% e.g., at least 91%, at least 92%, at least 93%, at least 94%, at least 95%, at least 96%, at least 97%, at least 98%, at least 99%, or 100% sequence identity to SEQ ID NO: 33.

EXAMPLES

Strains

According to Central Bureau vor Schnimmelkulture, *Acremonium alcalophilum* CBS 114.92 was isolated by A. Yoneda in 1984 from the sludge of pig faeces compost near Tsukui Lake, Japan.

According to Central Bureau vor Schnimmelkulture, *Aspergillus fumigatus* CBS 113.26 was isolated by C. Thom on or before 1926 from a soil sample from Germany.

Example 1: Cloning, Expression and Purification of the GH25 Lysozymes

The GH25 lysozyme from *Acremonium alcalophilum* CBS 114.92 (SEQ ID NO: 27) was cloned and expressed as described in example 8 and purified as described in example 5 of WO 2013/076253. Alternatively, SEQ ID NO: 27 can be cloned and expressed as described in example 2 of WO 2013/076253.

The GH25 lysozyme from *Aspergillus fumigatus* (SEQ ID NO: 29) may be cloned using basic molecular techniques (Ausubel et al., 2003, Curr. Prot. Mol. Biol., John Wiley & Sons, Cambridge, USA; Christgau et al. 1995, Curr. Genet. 27, 135-141).

Example 2: Determination of Phytase Activity 75 microliter phytase-containing enzyme solution, appropriately diluted in 0.25M sodium acetate, 0.005% (w/v) Tween-20, pH5.5, is dispensed in a microtiter plate well, e.g. NUNC 269620, and 75 microliter substrate is added (prepared by dissolving 100 mg sodium phytate from rice (Aldrich Cat. No. 274321) in 10 ml 0.25M sodium acetate buffer, pH5.5). The plate is sealed and incubated 15 min. shaken with 750 rpm at 37° C. After incubation, 75 microliter stop reagent is added (the stop reagent being prepared by mixing 10 ml molybdate solution (10% (w/v) ammonium hepta-molybdate in 0.25% (w/v) ammonia solution), 10 ml ammonium vanadate (0.24% commercial product from Bie&Berntsen, Cat. No. LAB17650), and 20 ml 21.7% (w/v) nitric acid), and the absorbance at 405 nm is measured in a microtiter plate spectrophotometer. The phytase activity is expressed in the unit of FYT, one FYT being the amount of enzyme that liberates 1 micromole inorganic orthophosphate per minute under the conditions above. An absolute value for the measured phytase activity may be obtained by reference to a standard curve prepared from appropriate dilutions of inorganic phosphate, or by reference to a standard curve made from dilutions of a phytase enzyme preparation with known activity (such standard enzyme preparation with a known activity is available on request from Novozymes A/S, Krogshoejvej 36, DK-2880 Bagsvaerd).

Example 3: Determination of Lysozyme Activity

Lysozyme activity was determined by measuring the decrease (drop) in absorbance/optical density of a solution of resuspended *Micrococcus lysodeikticus* ATTC No. 4698 (Sigma-Aldrich M3770) or *Exiguobacterium undea* (DSM14481) measured in a spectrophotometer at 540 nm.

Preparation of *Micrococcus* Lysodeikticus Substrate

Before use the cells were resuspended in citric acid-phosphate buffer pH 6.5 to a concentration of 0.5 mg cells/mL and the optical density (OD) at 540 nm was measured. The cell suspension was then adjusted so that the cell concentration equalled an OD540=1.0. The adjusted cell suspension was then stored cold before use. Resuspended cells were used within 4 hours.

Preparation of Dried Cells of *Exiguobacterium undae* Substrate

A culture of *E. undae* (DSM14481) was grown in 100 mL LB medium (Fluka 51208, 25 g/L) in a 500 mL shake-flask at 30° C., 250 rpm overnight. The overnight c ulture was then centrifuged at 20° C. and 5000 g for 10 minutes, and the pellet was then washed twice with sterile milliQ water, and resuspended in Milli-Q water. The washed cells were centrifuged for 1 minute at 13000 rpm and as much as possible of the supernatant was decanted. The washed cells were dried in a vacuum centrifuge for 1 hour. The cell pellet was resuspended in citric acid-phosphate buffer pH 4, 5 or 6 so that the optical density (OD) at 540 nm=1.

Measurement of Lysozyme Antimicrobial Activity in the Turbidity Assay

The lysozyme sample to be measured was diluted to a concentration of 100-200 mg enzyme protein/L in citric acid-phosphate buffer pH 4, 5 or 6, and kept on ice until use. In a 96 well microtiter plate (Nunc) 200 µL of the substrate was added to each well, and the plate was incubated at 37° C. for 5 minutes in a VERSAmax microplate reader (Molecular Devices). Following incubation, the absorbance of each well was measured at 540 nm (start value). To start the activity measurement, 20 µL of the diluted lysozyme sample was added to each substrate (200 µL) and kinetic measurement of absorbance at 540 nm was initiated for minimum 30 minutes up to 24 hours at 37° C. The measured absorbance at 540 nm was monitored for each well and over time a drop in absorbance is seen if the lysozyme has lysozyme activity. The results are presented in table 2 below.

TABLE 2

Lysozyme Activity against *Micrococcus lysodeikticus* and *Exiguobacterium undea* as measured by Optical Density Drop

| Lysozyme | *Micrococcus lysodeikticus*[1] | *Exiguobacterium undae*[1] |
|---|---|---|
| GH22 lysozyme from *Gallus gallus* (SEQ ID NO: 28) | +++ (pH 6) | + (pH 6) |
| GH25 lysozyme from *A. alcalophilum* (SEQ ID NO: 27) | + (pH 4) | + (pH 5) |
| GH25 lysozyme from *A. fumigatus* (SEQ ID NO: 29) | − (pH 4, 5 or 6) | +++ (pH 5) |

[1]− Means no significant effect; + means small effect; ++ means medium effect; +++ means large effect. The pH value in the brackets lists the assay pH based on lysozyme-substrate combination.

The data confirms that the GH22 lysozyme from *Gallus gallus*, the GH25 lysozyme from *A. alcalophilum* and the GH25 lysozyme from *A. fumigatus* all have lysozyme activity.

Example 4: Determination of Antimicrobial Activity

The antimicrobial activity of the GH25 lysozyme from *Aspergillus fumigatus* (SEQ ID NO: 29), the GH25 lysozyme from *Acremonium alcalophilum* (SEQ ID NO: 27) and the GH22 lysozyme from *Gallus gallus* (Hen Egg White lysozyme (HEWL), Sigma, 62971, SEQ ID NO: 28) against *Clostridium perfringens* DSM756 was tested using an RDA as described previously by Lehrer et al. (Lehrer R I, Rosenman M, Harwig S S et al. (1991), "Ultrasensitive assays for endogenous antimicrobial polypeptides", *J Immunol Methods*, 137:167-73), but with several modifications.

Briefly, RDA bacteria were prepared by streaking *C. perfringens* DSM756 from freeze stocks on Luria-Bertani agar plates (Sigma L3027) and the plates were incubated overnight at 37° C. under anaerobic conditions (Anaerogen, Oxoid) in a jar. The following day colonies were suspended in 0.9% NaCl and the suspensions were adjusted to McFarland std. 1.87% sterile glycerol was added to give a final glycerol concentration of 20% and the cells were frozen at −80° C. until use. For estimation of colony forming units (CFU) per milliliter of the RDA bacteria 10-fold dilution series were prepared of the freeze stock in 0.9% NaCl and 100 µl of the dilutions were plated on Luria-Bertani agar plates (Sigma L3027) and incubated overnight at 37° C. under anaerobic conditions (Anaerogen, Oxoid) in a jar.

When preparing the RDA plates broth media with agar was melted and cooled to 42° C. Two media's were tested in the experiment:

a) ½ Mueller-Hinton broth (MHB) (Sigma/Fluka, 90922) (i.e. adjusted to pH6 with 4M HCl and diluted 1:1 with water) with 1.5% agarose, and b) 1/10 Mueller-Hinton broth (MHB) (Sigma/Fluka, 90922) (i.e. diluted 1:9 with water) with 1% agarose.

For each assay plate 30 ml of melted media was added to achieve around $5.0\times10^5$ cfu/mL *C. perfringens* DSM756 and this was poured into a single-well omnitray (Nunc) plate. The omnitray plate was overlaid with a TSP plate (Nunc) and left to solidify (at room temperature or below). Afterwards, the TSP plate was removed; leaving 96 wells, in which 10 µL of the compound of interest could be tested.

10 µl of the test solutions were spotted pr. well and the plates were incubated over night at 37° C. in a jar under anaerobic condition (Anaerogen, Oxoid). The following day a clearing zone indicated inhibition of growth of test bacteria and thereby antimicrobial activity. For the RDA plates with ½ MHB, the clearing zones were visualized by coloring with MTT (3-(4,5-dimethylthiazol-2-yl)-2,5-diphenyltetrazolium bromide, a yellow tetrazole), that is reduced to purple formazan in living cells (Mosmann, Tim (1983), "Rapid colorimetric assay for cellular growth and survival: application to proliferation and cytotoxicity assays", *Journal of Immunological Methods* 65 (1-2): 55-63). This coloring provides for a dark coloring of living cells and no coloring of the clearing zones without living cells.

Bacitracin zinc salt (Sigma B-8800) (50 µg/ml) was included as a positive control and lysozymes were tested using a solution of 100 µg/ml. The results are presented in table 3 below.

TABLE 3

Antimicrobial Activity against *Clostridium perfringens* as measured by RDA

| Lysozyme | Diameter of clearing zone (mm) Experiment 1 1/10 MHB pH 7 | 2 1/10 MHB pH 7 | 1 ½ MHB pH 6 | 2 ½ MHB pH 6 |
|---|---|---|---|---|
| GH25 lysozyme from *A. alcalophilum* (SEQ ID NO: 27) | 11 | 11 | 6(20*) | 4(20*) |
| GH22 lysozyme from *Gallus gallus* (SEQ ID NO: 28) | 9 | 10 | 0 | 0 |

TABLE 3-continued

Antimicrobial Activity against *Clostridium perfringens* as measured by RDA

| Lysozyme | Diameter of clearing zone (mm) Experiment 1 1/10 MHB pH 7 | 2 1/10 MHB pH 7 | 1 ½ MHB pH 6 | 2 ½ MHB pH 6 |
|---|---|---|---|---|
| GH25 lysozyme from *Aspergillus fumigatus* (SEQ ID NO: 29) | 9 | 9 | 7 | 7 |
| Bacitracin zinc salt | 20 | 20 | 14 | 14 |

*Incomplete inhibition of growth visible after MTT coloring

Both the GH25 lysozyme from *Aspergillus fumigatus* and from *Acremonium alcalophilum* showed antimicrobial activity against viable cells of *C. perfringens* DSM756 under both conditions tested. For the GH25 lysozyme from *Aspergillus fumigatus* zones of around 7-9 mm were present around the wells inoculated with the enzyme. For the GH25 lysozyme from *Acremonium alcalophilum* a zone of 11 mm was present in 1/10 MBH, pH7, while in ½ MHB, pH 6 both a smaller clearing zone with a diameter of 4-6 mm and a larger incomplete clearing zone of 20 mm was present around the wells inoculated with the enzyme. The larger incomplete clearing zone became present after coloring with MTT. For HEWL no zone of inhibition was observed in ½ MHB, pH 6, while in 1/10 MHB, pH7 growth inhibition was present and resulted in inhibition zones of 9-10 mm.

In conclusion, whilst HEWL only inhibited growth in 1/10 MHB pH7, the two GH25 lysozymes surprisingly inhibited growth of *C. perfringens* DSM756 under both sets of conditions.

Example 5: In Vivo Broiler Trial 1

Treatments and Diet Composition

The basal diet was based upon wheat, rye, soybean meal, fish meal and sunflower meal, and was formulated and adjusted in two phases (Starter and Grower periods of 7 and 17 days, respectively) according to the growing animals changing requirements. Diet composition was designed to meet or exceed the requirements except for metabolisable energy, phosphorus and calcium (Tables 5.2, 5.3 and 5.4).

Starter feed did not contain lysozyme or phytase but served for a similar rearing period of 7 days and introduction of the birds to the main diet components in the Grower feeds. During the Grower period, the lysozyme (SEQ ID NO: 27) was applied at 50 g/t as a liquid formulation and the phytases (Quantum® Blue, AB Enzymes or RONOZYME® HiPhos, DSM Nutritional Products) were supplemented at recommended dosages (Table 5.1). Quantum® Blue is a commercially available animal feed *E. Coli* variant phytase whilst RONOZYME® HiPhos is a commercially available animal feed *Citrobacter* phytase.

There were no other enzymes or any coccidiostats supplemented in the diets.

The diets were prepared at a feedmill specialised in experimental diets and the mash feed was offered ad libitum to the birds.

TABLE 5.1

Study design

| Treatment | Lysozyme (g/t) (SEQ ID NO: 27) | Phytase | Phytase | Pens | Birds per pen |
|---|---|---|---|---|---|
| 1 | — | RONOZYME ® HiPhos | 1000 FYT/kg | 16 | 40 |
| 2 | — | Quantum ® Blue | 500 FTU/kg | 16 | 40 |
| 3 | 50 | RONOZYME ® HiPhos | 1000 FYT/kg | 16 | 40 |
| 4 | 50 | Quantum ® Blue | 500 FTU/kg | 16 | 40 |

TABLE 5.2

Diet composition (g/kg)

| Phase | Starter (Days 1-7) | Grower (Days 8-24) |
|---|---|---|
| Wheat | 511.25 | 473.90 |
| Rye | 50.00 | 100.00 |
| Soybean Meal (48% XP) | 261.00 | 207.00 |
| Soybean Hulls[1] | 29.00 | 23.00 |
| Fishmeal 70% XP | 50.00 | 20.00 |
| Sunflower Meal (low XP) | | 70.00 |
| Animal Fat (Lard) | | 30.00 |
| Soybean Oil | 62.50 | 42.00 |
| Premix | 5.00 | 5.00 |
| Lime fine | 13.50 | 13.50 |
| Monocalciumphosphate | 9.50 | 4.80 |
| Salt | 1.20 | 1.30 |
| NaHCO3 | 2.10 | 2.60 |
| L-Lysine HCl | 1.35 | 2.70 |
| DL-Methionine | 2.60 | 2.60 |
| L-Threonine | 0.95 | 1.15 |
| L-Valine | 0.05 | 0.45 |

[1]Soybean hulls were introduced to the diet in order to simulate low protein SBM, which was not available as a single ingredient

TABLE 5.3

Intended and analysed concentrations of nutrients (g/kg) and metabolisable energy ($AME_N$, MJ/kg)

| | Starter (Days 1-7) | | Grower (Days 8-24) | |
|---|---|---|---|---|
| Phase | Intended | Analysed | Intended | Analysed |
| AMEn, MJ/kg | 12.7 | 12.7 | 12.6 | 12.5 |
| Dry Matter | 881.2 | 884 | 880.7 | 887 |
| Crude Ash | 60.5 | 58 | 52.8 | 52 |
| Crude Protein | 228.7 | 224 | 202.3 | 199 |
| Crude Lipids | 81.5 | 86 | 88.2 | 90 |
| Crude Fibre | 31.5 | 37 | 46.6 | 54 |
| P | 6.7 | 5.4 | | |
| Ca | 9.1 | 7.5 | | |
| Lysine | 13.54 | 12.04 | | |
| Methionine | 6.33 | 5.80 | | |
| Methionine + Cystine | 9.93 | 9.15 | | |

TABLE 5.4

Premix composition

| Nutrient premix | Supplied per kg feed | Provided as |
|---|---|---|
| Vitamin A (retinyl acetate) | 12,000 IE | |
| Vitamin D$_3$ (cholecalciferol) | 2,400 IE | |
| Vitamin E (dl-a-tocopherol) | 50 mg | |
| Vitamin K$_3$ (menadione) | 1.5 mg | |
| Vitamin B$_1$ (thiamin) | 2.0 mg | |
| Vitamin B$_2$ (riboflavin) | 7.5 mg | |
| Vitamin B$_6$ (pyridoxine-HCl) | 3.5 mg | |
| Vitamin B$_{12}$ (cyanocobalamin) | 20 μg | |
| Niacin | 35 mg | |
| D-pantothenic acid | 10 mg | |
| Choline chloride | 460 mg | |
| Folic acid | 1.0 mg | |
| Biotin | 0.2 mg | |
| Iron | 80 mg | (267 mg $FeSO_4 \cdot H_2O$) |
| Copper | 12 mg | (48 mg $CuSO_4 \cdot 5H_2O$) |
| Manganese | 85 mg | (142 mg MnO) |
| Zinc | 60 mg | (169 mg $ZnSO_4 \cdot H_2O$) |
| Cobalt | 0.40 mg | (1.9 mg $CoSO_4 \cdot 7H_2O$) |
| Iodine | 0.8 mg | (1.1 mg KJ) |
| Selenium | 0.1 mg | (0.22 mg $Na_2SeO_3$) |
| Anti-oxidant mixture | 125 mg | Oxytrap PXN |

Animals and Housing

At the day of hatching, male day-old broiler type chickens (male byproducts of female parental line of Cobb 500) were obtained from Cobb Germany Avimex GmbH, Wiesenena (Brösenweg 80, 04509 Wiesenena).

The birds were randomly assigned in groups of 22 chickens to the experimental pens (~3 sq.m.) equipped with a bell drinker and a round feeder. After 7 days of equal rearing, number of birds per pen was reduced to 20, selecting against obviously light birds. Recorded body weights (BW) were immediately statistically evaluated. In order to ensure similar average BW between treatments and variation within treatments statistical evaluation of BW-placement of chicks was coordinated in such a way as to minimize within-pen variation and between-treatment differences of average BW.

Feed and water were freely available, feed consumption was recorded. Initial bedding consisted of wood shavings. Caked excreta patches around the drinkers were removed several times during the experimental period and more bedding material was added when required. Light and temperature regimes were managed according to the breeder's recommendations.

Birds were routinely vaccinated against Newcastle disease and Gumboro on day 18.

Data Recording and Calculation of Performance Parameters

Birds were weighed (groupwise) at placement and at the end of each fattening period. At the final weighing, birds were weighed individually. Feed offered was recorded continuously upon refilling the feeders; the feed remaining in the feeders was recorded at the end of each fattening period. From these data, feed consumption was calculated.

The weight of losses and culls was recorded upon occurrence.

Daily BW gain per bird (BW gain) and feed conversion ratio (FCR) were calculated as follows:

BWgain: difference between BW per bird at the end and at the beginning of the study divided by the number of days FCR: total feed consumption of a pen divided by total BW gain of that pen (total BW gain=total BW at the end+weight of removals and losses total BW at the beginning)

The European Production Efficiency Factor (EEF) was calculated as follows:

EEF=[(livability,% $x$ BWgain,kg)/(Study duration in days×FCR)]×100.

Statistical Analysis

Statistical unit was 'pen'. Prior to statistical analysis, an outlier test (Grubb's test) was conducted. As a consequence of this procedure no data was excluded from the dataset.

Data of performance was analysed using a bi-factorial ANOVA (procedure PROC GLM) with the fixed effects of lysozyme and phytase supplementation as well as their interaction. Differences were investigated between the various levels of each main factor (Tukey test), accounting for multiple comparisons where appropriate (phytase).

All statistical analysis was conducted using the software package SAS 9.3.

Results and Discussion

Losses and culls throughout the study ranged from 1.4 to 2.3% for individual treatments. No differences between either lysozyme levels or phytases were detected.

TABLE 5.5

FCR and EPEF results using lysozyme (SEQ ID NO: 27) and Quantum ® Blue (SEQ ID NO: 4) or RONOZYME ® HiPhos (SEQ ID NO: 10)

| Treatment | FCR | FCR change | % improvement | EPEF | EPEF change | % improvement |
|---|---|---|---|---|---|---|
| RONOZYME ® HiPhos | 1.561 | | | 333 | | |
| Quantum ® Blue | 1.586 | | | 319 | | |
| RONOZYME ® HiPhos + Lysozyme | 1.546 | −0.015 | 1.0 | 342 | 9 | 2.7 |
| Quantum ® Blue + Lysozyme | 1.561 | −0.025 | 1.6 | 338 | 19 | 6.0 |

The results show that there was an improvement in both FCR and EPEF when the GH25 lysozyme of SEQ ID NO: 27 was added to the broiler diet compared to when the diet only comprised a phytase.

Example 6: In Vivo Broiler Trial 2

The study was repeated as described in example 5 using the same set-up, diet and number of chickens, except that 2 different phytases were used as shown in table 6.1. Axtra® PHY is a commercially available animal feed *Buttiauxella* phytase whilst RONOZYME® NP is a commercially available animal feed *Peniophora lycii* variant phytase.

TABLE 6.1

Study design

| Treatment | Lysozyme (g/t) (SEQ ID NO: 27) | Phytase | Phytase | Pens | Birds per pen |
|---|---|---|---|---|---|
| 1 | — | Axtra ® PHY | 500 FTU/kg | 16 | 40 |
| 2 | — | RONOZYME ® NP | 1500 FYT/kg | 16 | 40 |
| 3 | 50 | Axtra ® PHY | 500 FTU/kg | 16 | 40 |
| 4 | 50 | RONOZYME ® NP | 1500 FYT/kg | 16 | 40 |

Results and Discussion

Losses and culls throughout the study ranged from 0.8 to 2.0% for individual treatments. No differences between either lysozyme levels or phytases were detected.

TABLE 6.2

FCR and EPEF Results using lysozyme (SEQ ID NO: 27) and Axtra ® PHY (SEQ ID NO: 17) or RONOZYME ® NP (SEQ ID NO: 22)

| Treatment | FCR | FCR change | % improvement | EPEF | EPEF change | % improvement |
|---|---|---|---|---|---|---|
| Axtra ® PHY | 1.53 | | | 327 | | |
| RONOZYME ® NP | 1.55 | | | 311 | | |
| Axtra ® PHY + Lysozyme | 1.51 | −0.02 | 1.3 | 332 | 5 | 1.5 |
| RONOZYME ® NP + Lysozyme | 1.52 | −0.03 | 1.9 | 322 | 11 | 3.5 |

The results show that there was an improvement in both FCR and EPEF when the GH25 lysozyme of SEQ ID NO: 27 was added to the broiler diet compared to when the diet only comprised a phytase.

Example 7: In Vivo Broiler Trial 3

The study was repeated as described in example 5 using the same set-up, diet and number of chickens, except that 3 different lysozymes were used as shown in table 7.1. RONOZYME® HiPhos is a commercially available animal feed *Citrobacter* phytase.

SEQ ID NO: 27 is a GH25 lysozyme from *Acremonium alcalophilum*, SEQ ID NO: 28 is a GH22 lysozyme from *Gallus gallus* (hen egg white lysozyme, HEWL (Sigma 62971, Lot 62971-50G-F)) and SEQ ID NO: 29 is a GH25 lysozyme from *Aspergillus fumigatus*.

TABLE 7.1

Study design

| Treatment | Lysozyme | Phytase | Phytase | Pens | Birds per pen |
|---|---|---|---|---|---|
| 1 | — | RONOZYME ® HiPhos | 1000 FYT/kg | 16 | 40 |
| 2 | 50 ppm SEQ ID NO: 27 | RONOZYME ® HiPhos | 1000 FYT/kg | 16 | 40 |
| 3 | 50 ppm SEQ ID NO: 29 | RONOZYME ® HiPhos | 1000 FYT/kg | 16 | 40 |
| 4 | 50 ppm SEQ ID NO: 28 | RONOZYME ® HiPhos | 1000 FYT/kg | 16 | 40 |

Results and Discussion

Losses and culls throughout the study ranged from 0.9 to 1.8% for individual treatments. No difference between the different lysozymes was detected.

Due to a bacterial infection during the trial, the broilers were administered Methaxasol-T in water on days 5 to 11 inclusive.

TABLE 7.2

FCR and EPEF Results using GH25 lysozyme (SEQ ID NO: 27), GH22 lysozyme (SEQ ID NO: 28) or GH25 lysozyme (SEQ ID NO: 29) and RONOZYME ® HiPhos (SEQ ID NO: 10)

| Treatment | FCR | FCR change | % improvement | EPEF | EPEF change | % improvement |
|---|---|---|---|---|---|---|
| RONOZYME ® HiPhos | 1.489 | | | 411 | | |
| RONOZYME ® HiPhos + 50 ppm SEQ ID NO: 27 | 1.456 | −0.034 | 2.2 | 431 | 20 | 4.8 |
| RONOZYME ® HiPhos + 50 ppm SEQ ID NO: 29 | 1.478 | −0.012 | 0.8 | 421 | 10 | 2.4 |
| RONOZYME ® HiPhos + 50 ppm SEQ ID NO: 28 | 1.505 | 0.016 | −1.0 | 395 | −16 | −3.8 |

The results show that the combination of a phytase and hen egg white lysozyme (SEQ ID NO: 28) negatively affected the performance of the chicken resulting in a worse FCR and EPEF. However, surprisingly both GH25 lysozymes (SEQ ID NO: 27 and 29) in combination with a phytase improved FCR and EPEF.

The results also show that FCR and EPEF for broilers administered either of the GH25 lysozymes improved even after a 7-day treatment with the antibiotic Methaxasol-T which is also surprising since it is well known that antibiotics alone improve animal performance.

Example 8: In Vivo Broiler Trial 4

Treatments and Diet Composition

The basal diet was based upon wheat, rye, soybean meal, fish meal and sunflower meal, and was formulated and adjusted in two phases (Starter and Grower periods of 6 and 18 days, respectively) according to the growing animals changing requirements. Diet composition was designed to meet or exceed the requirements except for metabolisable energy, phosphorus and calcium (tables 8.2 and 8.3) using the premix composition as described in table 5.4.

Starter feed did not contain lysozyme but served for a similar rearing period of 6 days and introduction of the birds to the main diet components in the Grower feeds. During the Grower period, the lysozyme (SEQ ID NO: 30) was applied at 25 g/t as a liquid formulation post pelleting. There were no other enzymes or any coccidiostats supplemented in the diets. The diets contained a commercial phytase at recommended level (Phyzyme XP10000TPT at 50 g/ton (500 FTU/kg)). Phyzyme XP10000TPT is a commercially available animal feed E. Coli variant phytase.

The diets were prepared at a feedmill specialised in experimental diets and the pelleted feed was offered ad libitum to the birds.

TABLE 8.1

Study design

| Treatment | Lysozyme (g/t) (SEQ ID NO: 30) | Phytase | Phytase | Pens | Birds per pen |
|---|---|---|---|---|---|
| 1 | — | Phyzyme XP10000TPT | 500 FTU/kg | 16 | 40 |
| 2 | 25 | Phyzyme XP10000TPT | 500 FTU/kg | 16 | 40 |

Data recording and statistical analysis was performed as described in Example 5.

TABLE 8.2

Diet composition (g/kg)

| Phase | Starter (Days 1-6) | Grower (Days 7-24) |
|---|---|---|
| Wheat | 508.55 | 466.4 |
| Rye | 50 | 100 |
| Soybean Meal (48% XP) | 261 | 216 |
| Soybean Hulls[1] | 29 | 20 |
| Fishmeal 70% XP | 50 | 20 |
| Sunflower Meal (low XP) | | 70 |
| Animal Fat (Lard) | | 30 |
| Soybean Oil | 65 | 45 |
| Premix | 5 | 5 |
| Lime fine | 13.3 | 11.8 |
| Monocalciumphosphate | 9.5 | 5 |
| Salt | 1.2 | 1.3 |
| NaHCO3 | 2.1 | 2.6 |
| L-Lysine HCl | 1.55 | 2.7 |
| DL-Methionine | 2.7 | 2.6 |
| L-Threonine | 1 | 1.1 |
| L-Valine | 0.1 | 0.5 |

[1]Soybean hulls were introduced to the diet in order to simulate low protein SBM, which was not available as a single ingredient

TABLE 8.3

Intended and analysed concentrations of nutrients (g/kg) and metabolisable energy ($AME_N$, MJ/kg)

| | Starter (Days 1-6) | | Grower (Days 7-24) | |
|---|---|---|---|---|
| Phase | Intended | Analysed | Intended | Analysed |
| AMEn, MJ/kg | 12.7 | 12.8 | 12.6 | 12.7 |
| Dry Matter | 885.4 | 894 | 886.1 | 898 |
| Crude Ash | 57.8 | 57 | 49.2 | 50 |
| Crude Protein | 227.9 | 228 | 202.1 | 200 |
| Crude Lipids | 81.4 | 88 | 90.8 | 97 |
| Crude Fibre | 31.4 | 31 | 48 | 48 |
| P | 6.6 | | 5.4 | |
| Ca | 9.1 | | 7.5 | |
| Lysine | 13.56 | | 11.98 | |
| Methionine | 6.42 | | 5.8 | |
| Methionine + Cystine | 10.01 | | 9.16 | |

Animals and Housing

At the day of hatching, male day-old Ross 308 broiler chickens were obtained from Geflügelhof Möckern (Pabsdorfer Weg 9, 39291 Möckern).

The birds were randomly assigned in groups of 42 chickens to the experimental pens (~3 sq.m.) equipped with a bell drinker and a round feeder.

After 6 days of equal rearing, the number of birds per pen was reduced to 40, selecting against obviously light birds. Recorded body weights (BW) were immediately statistically evaluated.

In order to ensure similar average BW between treatments and variation within treatments statistical evaluation of BWplacement of chicks was coordinated in such a way as to minimize within-pen variation and between-treatment differences of average BW.

Feed and water were freely available, feed consumption was recorded. Initial bedding consisted of wood shavings. Caked excreta patches around the drinkers were removed several times during the experimental period and more bedding material was added when required.

Light and temperature regimes were managed according to the breeder's recommendations. Birds were routinely vaccinated against Newcastle disease and Gumboro on day 14.

After vaccination the flock developed a general bacterial infection which caused increased losses. Therefore, an antibiotic treatment with Enro-Sleecol was initiated on day 18 for three days.

Results and Discussion

Losses and culls throughout the study ranged from 2.7 to 4.1% and from 3.4 to 5.8% for individual treatments in the 12 and 18 days feeding periods, respectively. No differences between either lysozyme nor phytase supplementation were detected.

TABLE 8.4

FCR and EPEF Results using GH25 lysozyme (SEQ ID NO: 30) and Phyzyme XP10000TPT

| Treatment | FCR | FCR change | % improvement | EPEF | EPEF change | % improvement |
|---|---|---|---|---|---|---|
| Phyzyme XP10000TPT | 1.40 | | | 433 | | |
| Phyzyme XP10000TPT + 25 ppm SEQ ID NO: 30 | 1.36 | −0.04 | 2.9 | 446 | 13 | 3.0 |

The results show that the combination of an E. Coli phytase and a GH25 lysozyme at 25 ppm (SEQ ID NO: 30) surprisingly improved both FCR and EPEF over the same phytase alone.

The results also show that FCR and EPEF improved even after a 3-day treatment with the antibiotic Enro-Sleecol which is also surprising since it is well known that antibiotics alone improve animal performance.

Example 9: In Vivo Broiler Trial 5

Treatments and Diet Composition

The basal diet was based upon wheat, rye, soybean meal, fish meal and sunflower meal, and was formulated and adjusted in two phases (Starter and Grower periods of 7 and 18 days, respectively) according to the growing animals changing requirements. Diet composition was designed to meet or exceed the requirements except for metabolisable energy, phosphorus and calcium and was very similar to that described in tables 8.2 and 8.3 using the premix composition as described in table 5.4.

Starter feed did not contain any lysozyme but served for a similar rearing period of 7 days and introduction of the birds to the main diet components. In the Grower feeds, either the lysozyme of SEQ ID NO: 30 or hen egg white lysozyme (SEQ ID NO: 28) were used as shown in table 9.1. Test products were applied as liquid formulations to mash diet. Starter and Grower diets contained a coccidiostat (Lasalocid at 100 ppm). The diets were prepared at a feedmill specialised in experimental diets and the mash feed was offered ad libitum to the birds.

TABLE 9.1

Study design

| Treatment | Lysozyme | Phytase | Phytase | Pens[1] | Birds per pen |
|---|---|---|---|---|---|
| 1 | — | RONOZYME ® NP | 1500 FYT/kg | 16/13 | 40 |
| 2 | SEQ ID NO: 30 (50 ppm) | RONOZYME ® NP | 1500 FYT/kg | 16/15 | 40 |
| 3 | SEQ ID NO: 28 (50 ppm) | RONOZYME ® NP | 1500 FYT/kg | 16/15 | 40 |

[1]Intended number of pens/Number of pens used for data evaluation. Discarded pens suffered from birds crossing pen partitions.

Data recording and statistical analysis was performed as described in Example 5.

Animals and Housing

At the day of hatching, male day-old Ross 308 broiler chickens were obtained from Geflügelhof Möckern (Pabsdorfer Weg 9, 39291 Möckern).

The birds were randomly assigned in groups of 42 chickens to the experimental pens (~3 sq.m.) equipped with a bell drinker and a round feeder.

After 7 days of equal rearing, the number of birds per pen was reduced to 40, selecting against obviously light birds. Recorded body weights (BW) were immediately statistically evaluated. In order to ensure similar average BW between treatments and variation within treatments statistical evaluation of BWplacement of chicks was coordinated in such a way as to minimize within-pen variation and between-treatment differences of average BW.

Feed and water were freely available, feed consumption was recorded. Initial bedding consisted of wood shavings. Caked excreta patches around the drinkers were removed several times during the experimental period and more bedding material was added when required.

Light and temperature regimes were managed according to the breeder's recommendations. Birds were routinely vaccinated against Newcastle disease and Gumboro on day 15.

Results and Discussion

Losses and culls throughout the study ranged from 1.4 to 3.6% throughout the study.

Example 10: Microbiota Analyses from In Vivo Broiler Trial 4 (Example 8) and In Vivo Broiler Trial 5 (Example 9)

The microbiota of broilers from the in vivo trials 4 and 5 (described in Examples 8 and 9 respectively) were analysed as described below. For in vivo trial 4 (Example 8), 45 chickens from each treatment (representing 15 individual pens each) were selected for analysis of the microbiota. For in vivo trial 5 (Example 9), 64 chickens from each of treatments 1 and 2, and 48 chickens from treatment 3 (representing 16 individual pens each) were selected for analysis of the microbiota.

Sampling

At the end of the feeding trials chickens selected for microbiota analysis were slaughtered for collection of gut content from the two ceca. The chickens were dissected directly after slaughtering and the intestines were eviscerated. The ceca were then separated from the rest of the intestines by cutting the ceca around 1 cm proximally from the ileocecal junction. This was done by use of a scissor (sterilized in an ethanol bath) or by use of disposable scalpels. The content of the two ceca were emptied collectively into one 15 ml tube. The content of the tube was mixed with an inoculation needle and the digesta was distributed into 4 separate Eppendorf tubes as small aliquots (50-500 mg). The samples were snap-freezed on dry ice and placed in a −80° C. freezer until further processing.

TABLE 9.2

FCR and EPEF Results using GH25 lysozyme (SEQ ID NO: 30) or GH22 lysozyme (SEQ ID NO: 28) and RONOZYME ® NP (SEQ ID NO: 22)

| Treatment | FCR | FCR change | % improvement | EPEF | EPEF change | % improvement |
|---|---|---|---|---|---|---|
| RONOZYME ® NP | 1.51 | — | — | 368 | — | — |
| RONOZYME ® NP + 50 ppm SEQ ID NO: 30 | 1.45 | −0.06 | 4.1% | 410 | 42 | 11.4% |
| RONOZYME ® NP + 50 ppm SEQ ID NO: 28 | 1.53 | +0.02 | −1.3% | 360 | −8 | −2.2% |

The results show that the combination of a phytase and hen egg white lysozyme (SEQ ID NO: 28) negatively affected the performance of the chicken resulting in a worse FCR and EPEF. However, surprisingly the GH25 lysozyme (SEQ ID NO: 30) in combination with a phytase improved FCR and EPEF.

DNA Extraction

DNA was extracted according to the "Nucleospin® Soil" protocol from the company Macherey-Nagel. Shortly, each individual sample from the chicken gut (50-250 mg) was suspended in buffer separating inhibitors from DNA. This was followed by bacterial cell lysis including bead beating.

DNA was then adsorped to a column in the presence of chaotropic salts. Washing steps with high-salt liquid and ethanol were used to remove contaminants and DNA was finally eluted using low-salt or water elution.

PCR Amplification of the 16S RNA Gene

After DNA extraction the extracted DNA was used as template for a PCR reaction targeting the V3-V4 variable regions of the 16S rRNA gene.

10-15 ng of extracted DNA was used as template and the PCR reaction (25 µL) contained dNTPs (400 nM of each), Phusion® Hot Start II DNA polymerase HF (2 mU), 1× Phusion® High Fidelity buffer (New England Biolabs Inc., USA), and barcoded library adaptors (400 nM) containing V3-4 specific primers as follows:

```
Amplification of V3-4 region of 16S RNA gene
Forward primer (341F):
                                         (SEQ ID NO: 31)
CCTACGGGNGGCWGCAG Reverse primer (805R):
                                         (SEQ ID NO: 32)
GACTACHVGGGTATCTAATCC
```

PCR settings: Initial denaturation at 98° C. for 2 min, 30 cycles of 98° C. for 30 s, 52° C. for 30 s, 72° C. for 30 s and final elongation at 72° C. for 5 min. The amplicon libraries were purified using the Agencourt® AMpure XP bead protocol (Beckmann Coulter, USA).

DNA Sequencing

The purified sequencing libraries were pooled and samples were paired end sequenced (280 bp×260 bp reads with dual indexes of 8 bp) on a MiSeq (Illumina) using a MiSeq Reagent kit v3, 600 cycles (Illumina) following the standard guidelines for preparing and loading samples on the MiSeq. 10% Phix control library or genomic DNA was spiked in to overcome low complexity issue often observed with amplicon samples.

Bioinformatics Processing, OTU Clustering and Classification

Forward and reverse reads were trimmed for quality using Trimmomatic v. 0.32 (Bolger, Anthony M., Marc Lohse, and Bjoern Usadel. 2014. "Trimmomatic: A flexible trimmer for Illumina sequence data." *Bioinformatics* 30 (15): 2114-20. doi:10.1093/bioinformatics/btu170) with the settings SLIDINGWINDOW:5:3 and MINLEN:275. The trimmed forward and reverse reads were merged using FLASH v. 1.2.7 (Magoc, Tanja, and Steven L Salzberg. 2011. "FLASH: fast length adjustment of short reads to improve genome assemblies." *Bioinformatics (Oxford, England)* 27 (21): 2957-63, doi:10.1093/bioinformatics/btr507) with the settings -m 25 -M 200. The merged reads were dereplicated and formatted for use in the UPARSE workflow (Edgar, Robert C. 2013. "UPARSE: highly accurate OTU sequences from microbial amplicon reads." *Nature Methods* 10 (10): 996-8. doi: 10.1038/nmeth.2604). The dereplicated reads were clustered, using the usearch v. 7.0.1090 -cluster_otus command with default settings. OTU abundances were estimated using the usearch v. 7.0.1090 -usearch_global command with -id 0.97. Taxonomy was assigned using the RDP classifier (Wang, Qiong, George M Garrity, James M Tiedje, and James R Cole. 2007. "Naive Bayesian classifier for rapid assignment of rRNA sequences into the new bacterial taxonomy." *Applied and Environmental Microbiology* 73 (16): 5261-7. doi:10.1128/AEM.00062-07.) as implemented in the parallel_assign_taxonomy_rdp.py script in QIIME (Caporaso, J Gregory, Justin Kuczynski, Jesse Stombaugh, Kyle Bittinger, Frederic D Bushman, Elizabeth K Costello, Noah Fierer, et al. 2010. "QIIME allows analysis of high-throughput community sequencing data." *Nature Methods* 7 (5), Nature Publishing Group: 335-6. doi:10.1038/nmeth.f.303), using the MiDAS database v.1.20 (McIlroy, Simon Jon, Aaron Marc Saunders, Mads Albertsen, Marta Nierychlo, Bianca McIlroy, Aviaja Anna Hansen, Søren Michael Karst, Jeppe Lund Nielsen, and Per Halkjr Nielsen. 2015. "MiDAS: the field guide to the microbes of activated sludge." *Database* 2015 (2): bav062. doi:10.1093/database/bav062).

Statistical Analysis

The results were analysed in R (R Core Team 2015) through the Rstudio IDE using the ampvis package v.1.9.1 (Albertsen, Mads, Søren M Karst, Anja S Ziegler, Rasmus H Kirkegaard, and Per H Nielsen. 2015. "Back to basics—the influence of DNA extraction and primer choice on phylogenetic analysis of activated sludge communities, PLoS ONE 10(7): e0132783, doi:10.1371/journal.pone.0132783), which builds on the R package DESeq2 (Love, Michael I., Wolfgang Huber, and Simon Anders. 2014. "Moderated estimation of fold change and dispersion for RNA-seq data with DESeq2." *Genome Biology* 15 (12): 550. doi:10.1186/s13059-014-0550-8.) for detecting species in differential abundance and vegan (Oksanen, Jari, Guillaume F Blanchet, Roeland Kindt, Pierre Legendre, Peter R. Minchin, R. B. O'Hara, Gavin L. Simpson, Peter Solymos, Henry H. Stevens, and Helene Wagner. 2015. "vegan: Community Ecology Package") for ordination and permutational manova analysis. Pens were used as statistical unit for the statistical analysis of the microbiota, meaning that the abundances of all bacteria were averaged over all the chickens in each individual pen. The detection of species of differential abundance between treatment groups was evaluated by p-values adjusted for multiple testing ($p_{adj}$) such that values of $p_{adj}$ lower than 0.05 were considered significant.

Results

The overall changes in the composition of the chicken gut microbiota upon treatment with SEQ ID NO: 30 are shown in table 9.1 below.

TABLE 9.1

Observed shift in the composition of the microbiota compared to the control group

| Trial | Lysozyme | Concentration | Significance[1] |
|---|---|---|---|
| In vivo trial 4 | SEQ ID NO: 30 | 25 ppm | +++ |
| In vivo trial 5 | SEQ ID NO: 30 | 50 ppm | +++ |
| In vivo trial 5 | SEQ ID NO: 28 | 50 ppm | – |

[1]Significant change (+++), p-value < 0.05, No significant change (–)

A shift in the microbial composition in the chicken gut is observed upon treatment with the lysozyme of SEQ ID NO: 30 and this effect is coupled to increased European Production Efficiency Factor (EPEF) in chickens. This shift is significant for in vivo trials 4 and 5 (Table 9.1). No significant shift in the microbioal composition in the chicken gut was observed upon treatment with hen egg-white lysozyme (lysozyme of SEQ ID NO: 28).

The observed changes in the composition of the chicken gut microbiota at operational taxonomic unit (OTU) level upon treatment with SEQ ID NO: 30 are shown in tables 9.2 and 9.3 below.

TABLE 9.2

Changes in the chicken gut microbiota at OTU level from in vivo trial 4

| OTU level | p-value | $p_{adj}$ | Control[1] | Lysozyme[2] | Change | Ratio | Tax. Assignment[3] (genus level) |
|---|---|---|---|---|---|---|---|
| OTU #1 | 0.0074 | 0.0932 | 20.6533 | 35.8615 | 15.2082 | 1.7364 | *Faecalibacterium* |
| OTU #5 | 0.2557 | 0.6344 | 3.1656 | 6.1311 | 2.9656 | 1.9368 | *Faecalibacterium* |

[1]Treatment 1 (no lysozyme);
[2]Treatment 2 (Lysozyme, SEQ ID NO: 30)
[3]Taxonomy Assignment

TABLE 9.3

Changes in the chicken gut microbiota at OTU level from in vivo trial 5

| OTU level | p-value | $p_{adj}$ | Control[1] | Lysozyme[2] | Change | Ratio | Tax. Assignment[3] (genus level) |
|---|---|---|---|---|---|---|---|
| OTU #1 | 0.0000 | 0.0002 | 16.4919 | 30.3170 | 13.8250 | 1.8383 | *Faecalibacterium* |
| OTU #45 | 0.0000 | 0.0003 | 2.8817 | 17.1121 | 14.2305 | 5.9383 | *Faecalibacterium* |

[1]Treatment 1 (no lysozyme);
[2]Treatment 2 (Lysozyme, SEQ ID NO: 30)
[3]Taxonomy Assignment Treatment with SEQ ID NO: 30 leads to a higher proportion of a bacterial species of the genus *Faecalibacterium* in the chicken gut and this shift is associated with increased European Production Efficiency Factor (EPEF) in chickens and this bacterial species has 96% identity to the species *Faecalibacterium prausnitzii*.

The observed changes in the composition of the chicken gut microbiota at genus level upon treatment with SEQ ID NO: 30 are shown in tables 9.4 and 9.5 below.

TABLE 9.4

Changes in the chicken gut microbiota at genus level from in vivo trial 4

| Genus level | p-value | $p_{adj}$ | Control[1] | Lysozyme[2] | Change | Ratio |
|---|---|---|---|---|---|---|
| *Faecalibacterium* | 0.0001 | 0.0018 | 34.2551 | 54.7182 | 20.4632 | 1.5974 |

[1]Treatment 1 (no lysozyme);
[2]Treatment 2 (Lysozyme, SEQ ID NO: 30)

TABLE 9.5

Composition of the chicken gut microbiota at genus level from in vivo trial 5

| Genus level | p-value | $p_{adj}$ | Control[1] | Lysozyme[2] | Change | Ratio |
|---|---|---|---|---|---|---|
| *Faecalibacterium* | 0.0000 | 0.0000 | 28.4033 | 50.3584 | 21.9551 | 1.7730 |

[1]Treatment 1 (no lysozyme);
[2]Treatment 2 (Lysozyme, SEQ ID NO: 30)

Treatment with SEQ ID NO: 30 leads to a higher proportion of bacteria of the genus *Faecalibacterium* in the chicken gut and this shift is associated with increased European Production Efficiency Factor (EPEF) in chickens.

The observed changes in the composition of the chicken gut microbiota at order level upon treatment with SEQ ID NO: 30 are shown in tables 9.6 and 9.7 below.

TABLE 9.6

Changes in the chicken gut microbiota at order level from in vivo trial 4

| Order level | p-value | $p_{adj}$ | Control | Lysozyme | Change | Ratio |
|---|---|---|---|---|---|---|
| Clostridiales | 0.3013 | 0.4522 | 75.7656 | 83.9434 | 8.1778 | 1.1079 |
| Bacteroidales | 0.2517 | 0.4522 | 10.4007 | 5.9195 | −4.4812 | 0.5691 |

[1]Treatment 1 (no lysozyme);
[2]Treatment 2 (Lysozyme, SEQ ID NO: 30)

TABLE 9.7

Changes in the chicken gut microbiota at order level from in vivo trial 5

| Order level | p-value | $p_{adj}$ | Control[1] | Lysozyme[2] | Change | Ratio |
|---|---|---|---|---|---|---|
| Clostridiales | 0.0001 | 0.0004 | 60.0516 | 74.4266 | 14.3750 | 1.2394 |
| Bacteroidales | 0.0773 | 0.1368 | 21.4920 | 9.6368 | −11.8552 | 0.4484 |

[1]Treatment 1 (no lysozyme);
[2]Treatment 2 (Lysozyme, SEQ ID NO: 30)

Treatment with SEQ ID NO: 30 leads to a higher proportion of bacteria of the order Clostridiales in the chicken gut and this shift is associated with increased European Production Efficiency Factor (EPEF) in chickens.

Treatment with SEQ ID NO: 30 leads to a lower proportion of bacteria of the order Bacteroidales in the chicken gut and this shift is associated with increased European Production Efficiency Factor (EPEF) in chickens.

A summary of the observed shift in the composition of the microbiota compared to the control group is presented in table 9.8 below.

TABLE 9.8

Observed shift in the composition of the microbiota compared to the control group

| | Significance[1] |
|---|---|
| OTU level (*Faecalibacterium* species) | |
| In vivo trial 4 (SEQ ID NO: 30 at 25 ppm) | + |
| In vivo trial 5 (SEQ ID NO: 30 at 50 ppm) | +++ |
| Genus level (*Faecalibacterium*) | |
| In vivo trial 4 (SEQ ID NO: 30 at 25 ppm) | +++ |
| In vivo trial 5 (SEQ ID NO: 30 at 50 ppm) | +++ |
| Order level (Clostridiales) | |
| In vivo trial 4 (SEQ ID NO: 30 at 25 ppm) | + |
| In vivo trial 5 (SEQ ID NO: 30 at 50 ppm) | +++ |
| Order level (Bacteroidales) | |
| In vivo trial 4 (SEQ ID NO: 30 at 25 ppm) | + |
| In vivo trial 5 (SEQ ID NO: 30 at 50 ppm) | + |

[1]Significant change (+++), $p_{adj}$ < 0.05, Numerical change (+)

In conclusion it can be seen that the GH25 lysozymes induced a significant shift in the microbial composition in the chicken gut and this effect is coupled to an increased European Production Efficiency Factor (EPEF) in chickens. Treatment with the GH25 lysozyme led to a higher proportion of bacterial species within the genus *Faecalibacterium*, and overall increased the proportion of bacteria of the order Clostridiales and decreased bacteria of the order Bacteroidales.

It can further be concluded that even though the broilers from in vivo trial 4 (Experiment 8) underwent a 3-day treatment with the antibiotic Enro-Sleecol, the GH25 lysozyme induced the same significant shift in the microbial composition in the chicken gut as when an antibiotic was not administered; i.e. a higher proportion of bacterial species within the genus *Faecalibacterium*, an overall increase in the proportion of bacteria of the order Clostridiales and a decrease in bacteria of the order Bacteroidales.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. An animal feed or animal feed additive comprising one or more polypeptides having phytase activity and one or more polypeptides having lysozyme activity, wherein:
   (a) the polypeptide having lysozyme activity is from glycosyl hydrolase family 25 and has at least 99% sequence identity to SEQ ID NO: 27; and
   (b) the polypeptide having phytase activity is an EC 3.1.3.26 phytase (4-phytase) and has at least 99% sequence identity to SEQ ID NO: 10.

2. The animal feed or animal feed additive of claim 1, wherein the animal feed or animal feed additive improves the European Production Efficiency Factor (EPEF) of an animal by at least 1%.

3. The animal feed or animal feed additive of claim 1, wherein the animal feed or animal feed additive improves the Feed Conversion Ratio (FCR) of an animal by at least 1%.

4. The animal feed or animal feed additive of claim 1, wherein the polypeptide having lysozyme activity is SEQ ID NO: 27.

5. The animal feed or animal feed additive of claim 1, wherein the polypeptide having phytase activity is SEQ ID NO: 10.

6. The animal feed or animal feed additive of claim 1, wherein the polypeptide having phytase activity is in granulate form, the polypeptide having lysozyme activity is in granulate form, or both the polypeptide having phytase activity and the polypeptide having lysozyme activity are in granulate form.

7. The animal feed or animal feed additive of claim 1, wherein the polypeptide having phytase activity is dosed at a level of 50 to 10000 FYT per kg animal feed.

8. The animal feed or animal feed additive of claim 1, wherein the polypeptide having lysozyme activity is dosed at a level of 0.1 to 150 ppm enzyme protein per kg animal feed.

9. A method of improving one or more performance parameters in an animal, comprising administering to one or more animals an animal feed or animal feed additive of claim 1, wherein the one or more performance parameters is selected from the group consisting of the European Production Efficiency Factor (EPEF) and Feed Conversion Ratio (FCR).

10. The method of claim 9, wherein the EPEF and/or FCR is improved by at least 1%.

11. A method of improving the European Production Efficiency Factor (EPEF) and/or Feed Conversion Ratio (FCR) of an animal comprising administering to the animal the animal feed or animal feed additive of claim 1.

12. The animal feed or animal feed additive of claim 1, wherein the polypeptide having lysozyme activity is SEQ ID NO: 27 and the polypeptide having phytase activity is SEQ ID NO: 10.

* * * * *

SEQUENCE LISTING

<160> NUMBER OF SEQ ID NOS: 54

<210> SEQ ID NO 1
<211> LENGTH: 410
<212> TYPE: PRT
<213> ORGANISM: E.Coli

<400> SEQUENCE: 1

```
Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
        50                  55                  60

Arg Leu Val Ala Asp Gly Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
        130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
        210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
            275                 280                 285

Tyr Gly Val Thr Leu Pro Thr Ser Val Leu Phe Ile Ala Gly His Asp
        290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
            355                 360                 365
```

```
Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 2
<211> LENGTH: 410
<212> TYPE: PRT
<213> ORGANISM: E.Coli

<400> SEQUENCE: 2

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Trp Leu Thr
            35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Ser Gln Leu Asn
                165                 170                 175

Leu Cys Leu Asn Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
        195                 200                 205

Gly Ala Val Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
            260                 265                 270

Asp Leu Ile Met Ala Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Pro Gly Gly Glu Leu Val Phe Glu
                325                 330                 335
```

```
Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 3
<211> LENGTH: 410
<212> TYPE: PRT
<213> ORGANISM: Artificial Sequence
<220> FEATURE:
<223> OTHER INFORMATION: E. Coli variant

<400> SEQUENCE: 3

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
                20                  25                  30

Thr Pro Asp Ala Trp Pro Thr Trp Pro Val Lys Leu Gly Glu Leu Thr
            35                  40                  45

Pro Arg Gly Gly Glu Leu Ile Ala Tyr Leu Gly His Tyr Trp Arg Gln
        50                  55                  60

Arg Leu Val Ala Asp Gly Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
                100                 105                 110

His Thr Gln Ala Asp Thr Ser Ser Pro Asp Pro Leu Phe Asn Pro Leu
            115                 120                 125

Lys Thr Gly Val Cys Gln Leu Asp Asn Ala Asn Val Thr Asp Ala Ile
        130                 135                 140

Leu Glu Arg Ala Gly Gly Ser Ile Ala Asp Phe Thr Gly His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
                180                 185                 190

Ala Leu Pro Ser Glu Leu Lys Val Ser Ala Asp Cys Val Ser Leu Thr
            195                 200                 205

Gly Ala Val Ser Leu Ala Ser Met Leu Thr Glu Ile Phe Leu Leu Gln
        210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Asp Leu
                245                 250                 255

Leu Gln Arg Thr Pro Glu Val Ala Arg Ser Arg Ala Thr Pro Leu Leu
                260                 265                 270

Asp Leu Ile Lys Thr Ala Leu Thr Pro His Pro Pro Gln Lys Gln Ala
            275                 280                 285
```

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
            355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 4
<211> LENGTH: 410
<212> TYPE: PRT
<213> ORGANISM: Artificial Sequence
<220> FEATURE:
<223> OTHER INFORMATION: E. Coli variant

<400> SEQUENCE: 4

Gln Ser Glu Pro Glu Leu Lys Leu Glu Ser Val Val Ile Val Ser Arg
1               5                   10                  15

His Gly Val Arg Ala Pro Thr Lys Phe Thr Gln Leu Met Gln Asp Val
            20                  25                  30

Thr Pro Asp Ala Trp Pro Thr Trp Pro Val Lys Leu Gly Glu Leu Thr
        35                  40                  45

Pro Arg Gly Gly Glu Leu Ile Ala Tyr Leu Gly His Tyr Trp Arg Gln
    50                  55                  60

Arg Leu Val Ala Asp Gly Leu Leu Pro Lys Cys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His His Gln Ala Asp Thr Ser Ser Pro Asp Pro Leu Phe Asn Pro Leu
        115                 120                 125

Lys Thr Gly Val Cys Gln Leu Asp Val Ala Asn Val Arg Arg Ala Ile
    130                 135                 140

Leu Glu Arg Ala Gly Gly Ser Ile Ala Asp Phe Thr Arg His Tyr Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190

Ala Leu Pro Ser Glu Leu Lys Val Ser Ala Asp Val Ser Leu Thr
        195                 200                 205

Gly Ala Trp Ser Leu Ala Ser Met Leu Thr Glu Ile Phe Leu Leu Gln
    210                 215                 220

Gln Ala Gln Gly Met Pro Glu Pro Gly Trp Gly Arg Ile Thr Asp Ser
225                 230                 235                 240

```
His Gln Trp Asn Thr Leu Leu Ser Leu His Asn Ala Val Phe Asp Leu
                245                 250                 255

Leu Gln Arg Thr Pro Glu Val Ala Arg Ser Arg Ala Thr Pro Leu Leu
            260                 265                 270

Asp Leu Ile Lys Thr Ala Leu Thr Pro His Pro Pro Gln Lys Gln Ala
        275                 280                 285

Tyr Gly Val Thr Leu Pro Thr Ser Val Leu Phe Ile Ala Gly His Asp
    290                 295                 300

Thr Asn Leu Ala Asn Leu Gly Gly Ala Leu Glu Leu Asn Trp Thr Leu
305                 310                 315                 320

Pro Gly Gln Pro Asp Asn Tyr Pro Pro Gly Gly Glu Leu Val Phe Glu
                325                 330                 335

Arg Trp Arg Arg Leu Ser Asp Asn Ser Gln Trp Ile Gln Val Ser Leu
            340                 345                 350

Val Phe Gln Thr Leu Gln Gln Met Arg Asp Lys Thr Pro Leu Ser Leu
        355                 360                 365

Asn Thr Pro Pro Gly Glu Val Lys Leu Thr Leu Ala Gly Cys Glu Glu
    370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 5
<211> LENGTH: 418
<212> TYPE: PRT
<213> ORGANISM: Artificial Sequence
<220> FEATURE:
<223> OTHER INFORMATION: E. Coli variant

<400> SEQUENCE: 5

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Ser
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125

Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Lys Arg Glu Lys Gln Asp Glu Ser Cys Ser Leu Thr Gln
            180                 185                 190
```

```
Ala Leu Pro Ser Glu Leu Lys Val Ser Ala Asp Asn Val Ser Leu Thr
            195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
            245                 250                 255

Leu Gln Arg Thr Pro Glu Val Ala Arg Ser Arg Ala Thr Pro Leu Leu
            260                 265                 270

Asp Leu Ile Met Ala Ala Leu Thr Pro His Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Ala Leu Glu Leu Asn Trp Thr Leu
305                 310                 315                 320

Pro Gly Gln Pro Asp Asn Thr Pro Pro Gly Gly Glu Leu Val Phe Glu
            325                 330                 335

Arg Trp Arg Arg Leu Ser Asp Asn Ser Gln Trp Ile Val Ser Leu
            340                 345                 350

Val Phe Gln Thr Leu Gln Gln Met Arg Asp Lys Thr Pro Leu Ser Leu
355                 360                 365

Asn Thr Pro Pro Gly Glu Val Lys Leu Thr Leu Ala Gly Cys Glu Glu
370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu Arg Ser His His His His
            405                 410                 415
His His

<210> SEQ ID NO 6
<211> LENGTH: 410
<212> TYPE: PRT
<213> ORGANISM: Artificial Sequence
<220> FEATURE:
<223> OTHER INFORMATION: E. Coli variant

<400> SEQUENCE: 6

Gln Ser Glu Pro Glu Leu Lys Leu Glu Ser Val Val Ile Val Ser Arg
1               5                   10                  15

His Gly Val Arg Ala Pro Thr Lys Ala Thr Gln Leu Met Gln Asp Val
            20                  25                  30

Thr Pro Asp Ala Trp Pro Thr Trp Pro Val Lys Leu Gly Trp Leu Thr
        35                  40                  45

Pro Arg Gly Gly Glu Leu Ile Ala Tyr Leu Gly His Tyr Gln Arg Gln
    50                  55                  60

Arg Leu Val Ala Asp Gly Leu Leu Ala Lys Lys Gly Cys Pro Gln Pro
65                  70                  75                  80

Gly Gln Val Ala Ile Ile Ala Asp Val Asp Glu Arg Thr Arg Lys Thr
                85                  90                  95

Gly Glu Ala Phe Ala Ala Gly Leu Ala Pro Asp Cys Ala Ile Thr Val
            100                 105                 110

His Thr Gln Ala Asp Thr Ser Ser Pro Asp Pro Leu Phe Asn Pro Leu
        115                 120                 125
```

```
Lys Thr Gly Val Cys Gln Leu Asp Asn Ala Asn Val Thr Asp Ala Ile
    130                 135                 140

Leu Ser Arg Ala Gly Gly Ser Ile Ala Asp Phe Thr Gly His Arg Gln
145                 150                 155                 160

Thr Ala Phe Arg Glu Leu Glu Arg Val Leu Asn Phe Pro Gln Ser Asn
                165                 170                 175

Leu Cys Leu Asn Arg Glu Lys Gln Asp Glu Ser Cys Ser Leu Thr Gln
            180                 185                 190

Ala Leu Pro Ser Glu Leu Lys Val Ser Ala Asp Asn Val Ser Leu Thr
                195                 200                 205

Gly Ala Val Ser Leu Ala Ser Met Leu Thr Glu Ile Phe Leu Leu Gln
210                 215                 220

Gln Ala Gln Gly Met Pro Glu Pro Gly Trp Gly Arg Ile Thr Asp Ser
225                 230                 235                 240

His Gln Trp Asn Thr Leu Leu Ser Leu His Asn Ala Gln Phe Tyr Leu
                245                 250                 255

Leu Gln Arg Thr Pro Glu Val Ala Arg Ser Arg Ala Thr Pro Leu Leu
                260                 265                 270

Asp Leu Ile Met Ala Ala Leu Thr Pro His Pro Pro Gln Lys Gln Ala
            275                 280                 285

Tyr Gly Val Thr Leu Pro Thr Ser Val Leu Phe Ile Ala Gly His Asp
            290                 295                 300

Thr Asn Leu Ala Asn Leu Gly Gly Ala Leu Glu Leu Asn Trp Thr Leu
305                 310                 315                 320

Pro Gly Gln Pro Asp Asn Thr Pro Gly Gly Glu Leu Val Phe Glu
                325                 330                 335

Arg Trp Arg Arg Leu Ser Asp Asn Ser Gln Trp Ile Gln Val Ser Leu
                340                 345                 350

Val Phe Gln Thr Leu Gln Gln Met Arg Asp Lys Thr Pro Leu Ser Leu
                355                 360                 365

Asn Thr Pro Pro Gly Glu Val Lys Leu Thr Leu Ala Gly Cys Glu Glu
            370                 375                 380

Arg Asn Ala Gln Gly Met Cys Ser Leu Ala Gly Phe Thr Gln Ile Val
385                 390                 395                 400

Asn Glu Ala Arg Ile Pro Ala Cys Ser Leu
                405                 410

<210> SEQ ID NO 7
<211> LENGTH: 411
<212> TYPE: PRT
<213> ORGANISM: Artificial Sequence
<220> FEATURE:
<223> OTHER INFORMATION: E. Coli variant

<400> SEQUENCE: 7

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
        50                  55                  60

Gln Arg Leu Val Ala Asp Gly Leu Leu Pro Lys Glu Gly Cys Pro Gln
65                  70                  75                  80
```

```
Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His His Gln Ala Asp Thr Ser Ser Pro Asp Pro Leu Phe Asn Pro
        115                 120                 125

Leu Lys Thr Gly Val Cys Gln Leu Asp Val Ala Asn Val Arg Arg Ala
130                 135                 140

Ile Leu Arg Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Tyr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 8
<211> LENGTH: 411
<212> TYPE: PRT
<213> ORGANISM: Artificial Sequence
<220> FEATURE:
<223> OTHER INFORMATION: E. Coli variant

<400> SEQUENCE: 8

Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30
```

Val Thr Pro Asp Ala Trp Pro Thr Trp Pro Val Lys Leu Gly Glu Leu
            35                  40                  45

Thr Pro Arg Gly Gly Glu Leu Ile Ala Tyr Leu Gly His Tyr Trp Arg
 50                  55                  60

Gln Arg Leu Val Ala Asp Gly Leu Leu Pro Lys Glu Gly Cys Pro Gln
 65                  70                  75                  80

Ser Gly Gln Val Ala Ile Ile Ala Asp Val Asp Glu Arg Thr Arg Lys
                 85                  90                  95

Thr Gly Glu Ala Phe Ala Ala Gly Leu Ala Pro Asp Cys Ala Ile Thr
                100                 105                 110

Val His His Gln Ala Asp Thr Ser Ser Pro Asp Pro Leu Phe Asn Pro
            115                 120                 125

Leu Lys Thr Gly Val Cys Gln Leu Asp Val Ala Asn Val Thr Arg Ala
130                 135                 140

Ile Leu Arg Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Val Ser Leu
195                 200                 205

Thr Gly Ala Val Ser Leu Ala Ser Met Leu Thr Glu Ile Phe Leu Leu
            210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
            275                 280                 285

Ala Tyr Gly Val Thr Leu Pro Thr Ser Val Leu Phe Ile Ala Gly His
290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Tyr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 9
<211> LENGTH: 411
<212> TYPE: PRT
<213> ORGANISM: Artificial Sequence
<220> FEATURE:
<223> OTHER INFORMATION: E. Coli variant

<400> SEQUENCE: 9

```
Met Gln Ser Glu Pro Glu Leu Lys Leu Glu Ser Val Val Ile Val Ser
1               5                   10                  15

Arg His Gly Val Arg Ala Pro Thr Lys Ala Met Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala His Leu Gly His Tyr Trp Arg
    50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Asn Val Arg Arg Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Cys Val Ser Leu
        195                 200                 205

Thr Gly Ala Val Ser Leu Ala Ser Met Leu Thr Glu Ile Phe Leu Leu
    210                 215                 220

Gln His Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Glu Trp Thr
305                 310                 315                 320

Leu Pro Gly Gln Pro Asp Asn Tyr Pro Pro Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
```

<210> SEQ ID NO 10
<211> LENGTH: 411
<212> TYPE: PRT
<213> ORGANISM: Citrobacter braakii ATCC 51113

<400> SEQUENCE: 10

```
Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asn Val
            20                  25                  30

Thr Pro Asp Gln Trp Pro Gln Trp Asp Val Pro Leu Gly Trp Leu Thr
        35                  40                  45

Pro Arg Gly Gly Glu Leu Val Ser Glu Leu Gly Gln Tyr Gln Arg Leu
    50                  55                  60

Trp Phe Thr Ser Lys Gly Leu Leu Asn Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Ala Phe Leu Ala Gly Leu Ala Pro Lys Cys Gln Ile Gln Val
            100                 105                 110

His Tyr Gln Lys Asp Glu Glu Lys Asn Asp Pro Leu Phe Asn Pro Val
        115                 120                 125

Lys Met Gly Lys Cys Ser Phe Asn Thr Leu Gln Val Lys Asn Ala Ile
130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
            180                 185                 190

Leu Pro Ser Glu Leu Lys Val Thr Pro Asp Asn Val Ser Leu Pro Gly
        195                 200                 205

Ala Trp Ser Leu Ser Ser Thr Leu Thr Glu Ile Phe Leu Leu Gln Glu
    210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255

Gln Arg Thr Pro Glu Val Ala Arg Ser Arg Ala Thr Pro Leu Leu Asp
            260                 265                 270

Met Ile Asp Thr Ala Leu Leu Thr Asn Gly Thr Thr Glu Asn Arg Tyr
        275                 280                 285

Gly Ile Lys Leu Pro Val Ser Leu Leu Phe Ile Ala Gly His Asp Thr
    290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Pro Gly Gly Glu Leu Val Phe Glu Lys
                325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
        355                 360                 365
```

```
Lys Pro Ala Gly Lys Val Asp Leu Lys Leu Ile Ala Cys Glu Glu Lys
        370                 375                 380
Asn Ser Gln Gly Met Cys Ser Leu Lys Ser Phe Ser Arg Leu Ile Lys
385                 390                 395                 400
Glu Ile Arg Val Pro Glu Cys Ala Val Thr Glu
                405                 410

<210> SEQ ID NO 11
<211> LENGTH: 410
<212> TYPE: PRT
<213> ORGANISM: Citrobacter gillenii

<400> SEQUENCE: 11

Asp Glu Gln Ser Gly Met Gln Leu Glu Arg Val Val Ile Val Ser Arg
1               5                   10                  15
His Gly Val Arg Ala Pro Thr Lys Phe Thr Pro Leu Met Gln Gln Val
                20                  25                  30
Thr Pro Asp Arg Trp Pro Gln Trp Asp Val Pro Leu Gly Trp Leu Thr
            35                  40                  45
Pro Arg Gly Gly Ala Leu Ile Thr Glu Leu Gly Arg Tyr Gln Arg Leu
        50                  55                  60
Arg Leu Ala Asp Lys Gly Leu Leu Asp Asn Lys Thr Cys Pro Thr Ala
65                  70                  75                  80
Gly Gln Val Ala Val Ile Ala Asp Ser Asp Gln Arg Thr Arg Lys Thr
                85                  90                  95
Gly Glu Ala Phe Leu Ala Gly Leu Ala Pro Glu Cys Lys Val Gln Val
            100                 105                 110
Tyr Tyr Gln Gln Asp Lys Ser Lys Ser Asp Pro Leu Phe Asn Pro Ile
        115                 120                 125
Lys Ala Gly Arg Cys Ser Leu Asn Thr Ser Gln Val Lys Glu Ala Ile
130                 135                 140
Leu Thr Arg Ala Gly Gly Ser Leu Asp Glu Tyr Thr Arg His Tyr Gln
145                 150                 155                 160
Pro Ala Phe Gln Ala Leu Glu Arg Val Leu Asn Phe Ser Gln Ser Glu
                165                 170                 175
Lys Cys Gln Ala Ala Gly Gln Ser Ala Gln Cys Thr Leu Thr Asp Val
            180                 185                 190
Leu Pro Ala Glu Leu Lys Val Ser Pro Glu Asn Ile Ser Leu Ser Gly
        195                 200                 205
Ser Trp Gly Leu Ala Ser Thr Leu Thr Glu Ile Phe Leu Leu Gln Gln
210                 215                 220
Ala Gln Gly Met Ser Gln Val Ala Trp Gly Arg Ile His Gly Asp Lys
225                 230                 235                 240
Glu Trp Arg Thr Leu Leu Ser Leu His Asn Ala Gln Phe Asp Leu Leu
                245                 250                 255
Gln Lys Thr Pro Glu Val Ala Arg Ser Arg Ala Thr Pro Leu Leu Asp
            260                 265                 270
Leu Ile Arg Thr Ala Leu Val Thr Gln Gly Ala Thr Glu Asn Lys Tyr
        275                 280                 285
Ala Ile Gln Leu Pro Val Ser Leu Leu Phe Ile Ala Gly His Asp Thr
290                 295                 300
Asn Leu Ala Asn Ile Ser Gly Ala Leu Gly Leu Asn Val Phe Leu Pro
305                 310                 315                 320
Gly Gln Pro Asp Asn Thr Pro Pro Gly Gly Glu Phe Val Phe Glu Arg
                325                 330                 335
```

Trp Lys Arg Val Ser Asp His Ser Asp Trp Val Gln Val Ser Phe Met
                340                 345                 350

Tyr Gln Thr Leu Gln Glu Met Arg Asp Met Gln Pro Leu Ser Leu Gln
                355                 360                 365

Ser Pro Pro Gly Lys Ile Val Leu Pro Leu Ala Ala Cys Asp Glu Lys
370                 375                 380

Asn Thr Gln Gly Met Cys Ser Leu Lys Asn Phe Ser Ala Leu Ile Asp
385                 390                 395                 400

Ser Val Arg Val Ser Glu Cys Ala Glu Lys
                405                 410

<210> SEQ ID NO 12
<211> LENGTH: 414
<212> TYPE: PRT
<213> ORGANISM: Citrobacter amalonaticus

<400> SEQUENCE: 12

Glu Val Pro Asp Asp Met Lys Leu Glu Arg Val Ile Val Ser Arg
1               5                   10                  15

His Gly Val Arg Ala Pro Thr Lys Phe Thr Pro Leu Met Gln Glu Ile
                20                  25                  30

Thr Pro Tyr His Trp Pro Gln Trp Asp Val Pro Leu Gly Trp Leu Thr
                35                  40                  45

Ala Arg Gly Gly Glu Leu Val Thr Glu Met Gly Arg Tyr Gln Gln Lys
            50                  55                  60

Val Leu Ile Asp Asn Gly Val Leu Glu Ser Asn Val Cys Pro Ser Pro
65                  70                  75                  80

Glu Gln Val Ala Val Ile Ala Asp Thr Asp Gln Arg Thr Arg Lys Thr
                85                  90                  95

Gly Glu Ala Phe Leu Ala Gly Phe Ala Pro Gly Cys Lys Asn Lys Val
                100                 105                 110

His Tyr Gln Lys Asp His Asp Lys Lys Asp Pro Leu Phe Asn Pro Val
                115                 120                 125

Lys Met Gly Val Cys Ala Phe Asn Val Gln Lys Thr Gln Glu Ala Ile
130                 135                 140

Leu Thr Arg Ala Glu Gly Asn Ile Glu Arg Tyr Thr Gln Arg Tyr Asp
145                 150                 155                 160

Ser Ala Phe Arg Thr Leu Glu Gln Val Leu Asn Phe Ser Arg Ser Ala
                165                 170                 175

Ala Cys Arg Ser Ala Ser Gln Ser Gly Cys Thr Leu Pro Gly Thr Leu
                180                 185                 190

Pro Ser Glu Leu Arg Val Ser Ala Asp Thr Val Ser Leu Ser Gly Ala
                195                 200                 205

Trp Ser Leu Ser Ser Met Leu Thr Glu Ile Phe Leu Leu Gln Glu Ala
            210                 215                 220

Gln Gly Met Pro Glu Val Ala Trp Gly Arg Ile His Gly Glu Lys Glu
225                 230                 235                 240

Trp Thr Ala Leu Leu Ser Leu His Asn Ala Gln Phe Asp Leu Leu Gln
                245                 250                 255

Arg Thr Pro Glu Val Ala Arg Ser Arg Ala Thr Pro Leu Leu Asp Leu
                260                 265                 270

Ile Ser Glu Ala Leu Val Ser Asn Gly Ser Thr Glu Asn His Tyr Gly
                275                 280                 285

Ile Lys Leu Pro Val Ser Leu Leu Phe Ile Ala Gly His Asp Thr Asn

```
                290             295             300
Leu Ala Asn Leu Ser Gly Val Phe Asp Leu Asn Trp Ser Leu Pro Gly
305                 310                 315                 320

Gln Pro Asp Asn Thr Pro Pro Gly Gly Glu Leu Val Phe Glu Arg Trp
                    325                 330                 335

Thr Arg Val Ser Asp Asn Thr Asp Trp Ile Gln Ile Ser Phe Val Tyr
                340                 345                 350

Gln Thr Leu Gln Gln Met Arg Lys Phe Lys Pro Phe Ser Ser Ser Ser
            355                 360                 365

Leu Pro Asn Lys Ile Val Leu Thr Leu Pro Ser Cys Gln Asp Lys Asn
        370                 375                 380

Pro Glu Gly Met Cys Pro Leu Lys His Phe Ile Asp Ile Val Gln Thr
385                 390                 395                 400

Ala Arg Ile Pro Gln Cys Ala Val Met Ala Asp Val Asn Arg
                405                 410

<210> SEQ ID NO 13
<211> LENGTH: 411
<212> TYPE: PRT
<213> ORGANISM: Citrobacter braakii YH-15 KCCM 10427

<400> SEQUENCE: 13

Glu Glu Gln Asn Gly Met Lys Leu Glu Arg Val Val Ile Val Ser Arg
1               5                   10                  15

His Gly Val Arg Ala Pro Thr Lys Phe Thr Pro Ile Met Lys Asp Val
                20                  25                  30

Thr Pro Asp Gln Trp Pro Gln Trp Asp Val Pro Leu Gly Trp Leu Thr
            35                  40                  45

Pro Arg Gly Gly Glu Leu Val Ser Glu Leu Gly Gln Tyr Gln Arg Leu
        50                  55                  60

Trp Phe Thr Ser Lys Gly Leu Leu Asn Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Ala Phe Leu Ala Gly Leu Ala Pro Lys Cys Gln Ile Gln Val
                100                 105                 110

His Tyr Gln Lys Asp Glu Glu Lys Asn Asp Pro Leu Phe Asn Pro Val
            115                 120                 125

Lys Met Gly Lys Cys Ser Phe Asn Thr Leu Lys Val Lys Asn Ala Ile
130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
            180                 185                 190

Leu Pro Ser Glu Phe Lys Val Thr Pro Asp Asn Val Ser Leu Pro Gly
        195                 200                 205

Ala Trp Ser Leu Ser Ser Thr Leu Thr Glu Ile Phe Leu Leu Gln Glu
210                 215                 220

Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
                245                 250                 255
```

```
Gln Arg Thr Pro Glu Val Ala Arg Ser Arg Ala Thr Pro Leu Leu Asp
            260                 265                 270

Met Ile Asp Thr Ala Leu Leu Thr Asn Gly Thr Thr Glu Asn Arg Tyr
        275                 280                 285

Gly Ile Lys Leu Pro Val Ser Leu Leu Phe Ile Ala Gly His Asp Thr
        290                 295                 300

Asn Leu Ala Asn Leu Ser Gly Ala Leu Asp Leu Lys Trp Ser Leu Pro
305                 310                 315                 320

Gly Gln Pro Asp Asn Thr Pro Pro Gly Gly Glu Leu Val Phe Glu Lys
            325                 330                 335

Trp Lys Arg Thr Ser Asp Asn Thr Asp Trp Val Gln Val Ser Phe Val
        340                 345                 350

Tyr Gln Thr Leu Arg Asp Met Arg Asp Ile Gln Pro Leu Ser Leu Glu
        355                 360                 365

Lys Pro Ala Gly Lys Val Asp Leu Lys Leu Ile Ala Cys Glu Glu Lys
        370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
            405                 410

<210> SEQ ID NO 14
<211> LENGTH: 411
<212> TYPE: PRT
<213> ORGANISM: Citrobacter freundii P3-42

<400> SEQUENCE: 14

Glu Glu Pro Asn Gly Met Lys Leu Glu Arg Val Val Ile Val Ser Arg
1               5                   10                  15

His Gly Val Arg Ala Pro Thr Lys Phe Thr Pro Ile Met Lys Asp Val
            20                  25                  30

Thr Pro Asp Gln Trp Pro Gln Trp Asp Val Pro Leu Gly Trp Leu Thr
        35                  40                  45

Pro Arg Gly Gly Glu Leu Val Ser Glu Leu Gly Gln Tyr Gln Arg Leu
    50                  55                  60

Trp Phe Thr Ser Lys Gly Leu Leu Asn Asn Gln Thr Cys Pro Ser Pro
65                  70                  75                  80

Gly Gln Val Ala Val Ile Ala Asp Thr Asp Gln Arg Thr Arg Lys Thr
                85                  90                  95

Gly Glu Ala Phe Leu Ala Gly Leu Ala Pro Lys Cys Gln Ile Gln Val
            100                 105                 110

His Tyr Gln Lys Asp Glu Glu Lys Thr Asp Pro Leu Phe Asn Pro Val
        115                 120                 125

Lys Met Gly Thr Cys Ser Phe Asn Thr Leu Lys Val Lys Asn Ala Ile
        130                 135                 140

Leu Glu Arg Ala Gly Gly Asn Ile Glu Leu Tyr Thr Gln Arg Tyr Gln
145                 150                 155                 160

Ser Ser Phe Arg Thr Leu Glu Asn Val Leu Asn Phe Ser Gln Ser Glu
                165                 170                 175

Thr Cys Lys Thr Thr Glu Lys Ser Thr Lys Cys Thr Leu Pro Glu Ala
            180                 185                 190

Leu Pro Ser Glu Leu Lys Val Thr Pro Asp Asn Val Ser Leu Pro Gly
        195                 200                 205

Ala Trp Ser Leu Ser Ser Thr Leu Thr Glu Ile Phe Leu Leu Gln Glu
        210                 215                 220
```

```
Ala Gln Gly Met Pro Gln Val Ala Trp Gly Arg Ile Thr Gly Glu Lys
225                 230                 235                 240

Glu Trp Arg Asp Leu Leu Ser Leu His Asn Ala Gln Phe Asp Leu Leu
            245                 250                 255

Gln Arg Thr Pro Glu Val Ala Arg Ser Arg Ala Thr Pro Leu Leu Asp
            260                 265                 270

Met Ile Asp Thr Ala Leu Leu Thr Asn Gly Thr Thr Glu Asn Arg Tyr
            275                 280                 285

Gly Ile Lys Leu Pro Val Ser Leu Leu Phe Ile Ala Gly His Asp Thr
            290                 295                 300

Asn Leu Ala Asn Leu Ser Gly Ala Leu Asp Leu Asn Trp Ser Leu Pro
305                 310                 315                 320

Gly Gln Pro Asp Asn Thr Pro Pro Gly Gly Glu Leu Val Phe Glu Lys
            325                 330                 335

Trp Lys Arg Thr Ser Asp Asn Thr Asp Trp Val Gln Val Ser Phe Val
            340                 345                 350

Tyr Gln Thr Leu Arg Asp Met Arg Asp Ile Gln Pro Leu Ser Leu Glu
            355                 360                 365

Lys Pro Ala Gly Lys Val Asp Leu Lys Leu Ile Ala Cys Glu Glu Lys
370                 375                 380

Asn Ser Gln Gly Met Cys Ser Leu Lys Ser Phe Ser Arg Leu Ile Lys
385                 390                 395                 400

Glu Ile Arg Val Pro Glu Cys Ala Val Thr Glu
            405                 410

<210> SEQ ID NO 15
<211> LENGTH: 413
<212> TYPE: PRT
<213> ORGANISM: Buttiauxella sp P1-29

<400> SEQUENCE: 15

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Glu Cys His Leu
            100                 105                 110

Thr Ile His His Gln Gln Asp Ile Lys Lys Ala Asp Pro Leu Phe His
        115                 120                 125

Pro Val Lys Ala Gly Thr Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175

Ser Ala Trp Cys Gln Lys His Ser Ala Asp Lys Ser Cys Asp Leu Gly
```

```
                180                 185                 190
Leu Ser Met Pro Ser Lys Leu Ser Ile Lys Asp Asn Gly Asn Lys Val
            195                 200                 205

Ala Leu Asp Gly Ala Ile Gly Leu Ser Ser Thr Leu Ala Glu Ile Phe
        210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 16
<211> LENGTH: 413
<212> TYPE: PRT
<213> ORGANISM: Buttiauxella sp. P1-29

<400> SEQUENCE: 16

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly His Leu Ile Ser Leu Met Gly Gly Phe Tyr
    50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Thr Cys Ser Met Asp Lys Thr Gln Val Gln Gln
    130                 135                 140
```

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175

Ser Ala Trp Cys Gln Lys His Ser Ala Asp Lys Ser Cys Asp Leu Gly
                180                 185                 190

Leu Ser Met Pro Ser Lys Leu Ser Ile Lys Asp Asn Gly Asn Lys Val
                195                 200                 205

Ala Leu Asp Gly Ala Ile Gly Leu Ser Ser Thr Leu Ala Glu Ile Phe
            210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Val Gln
                245                 250                 255

Phe Asp Leu Met Ala Arg Thr Pro Tyr Ile Ala Arg His Asn Gly Thr
                260                 265                 270

Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
                340                 345                 350

Ser Met Val Tyr Gln Thr Leu Glu Gln Leu Arg Ser Gln Thr Pro Leu
                355                 360                 365

Ser Leu Asn Gln Pro Ala Gly Ser Val Gln Leu Lys Ile Pro Gly Cys
            370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 17
<211> LENGTH: 413
<212> TYPE: PRT
<213> ORGANISM: Artificial Sequence
<220> FEATURE:
<223> OTHER INFORMATION: Buttiauxella variant

<400> SEQUENCE: 17

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
                35                  40                  45

Ile Thr Pro Arg Gly Glu His Leu Ile Ser Leu Met Gly Gly Phe Tyr
            50                  55                  60

Arg Gln Lys Phe Gln Gln Gln Gly Ile Leu Ser Gln Gly Ser Cys Pro
65              70                  75                  80

Thr Pro Asn Ser Ile Tyr Val Trp Thr Asp Val Ala Gln Arg Thr Leu
                85                  90                  95

-continued

```
Lys Thr Gly Glu Ala Phe Leu Ala Gly Leu Ala Pro Gln Cys Gly Leu
                100                 105                 110

Thr Ile His His Gln Gln Asn Leu Glu Lys Ala Asp Pro Leu Phe His
            115                 120                 125

Pro Val Lys Ala Gly Ile Cys Ser Met Asp Lys Thr Gln Val Gln Gln
        130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 18
<211> LENGTH: 413
<212> TYPE: PRT
<213> ORGANISM: Buttiauxella gaviniae DSM18930

<400> SEQUENCE: 18

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60
```

Arg Glu Lys Phe Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
            85                  90                  95

Lys Thr Gly Glu Ala Phe Leu Ala Gly Leu Ala Pro Gln Cys Gly Leu
        100                 105                 110

Thr Ile His His Gln Gln Asn Leu Glu Lys Ala Asp Pro Leu Phe His
    115                 120                 125

Pro Val Lys Ala Gly Thr Cys Ser Met Asp Lys Thr Arg Leu Gln Gln
130                 135                 140

Ala Val Glu Lys Glu Ala Gln Thr Pro Ile Glu Asn Leu Asn Gln His
145                 150                 155                 160

Tyr Ile Pro Ser Leu Ala Leu Met Asn Thr Thr Leu Asn Phe Ser Thr
                165                 170                 175

Ser Ala Trp Cys Gln Lys His Ser Ala Asp Lys Ser Cys Asp Leu Ala
            180                 185                 190

Gln Ser Met Pro Ser Lys Leu Ser Ile Lys Asp Asn Gly Asn Lys Val
        195                 200                 205

Ala Leu Asp Gly Ala Val Gly Leu Ser Ser Thr Leu Ala Glu Ile Phe
    210                 215                 220

Leu Leu Glu Tyr Ala Gln Gly Met Pro Gln Ala Ala Trp Gly Lys Ile
225                 230                 235                 240

His Ser Glu Gln Asp Trp Ala Glu Leu Leu Lys Leu His Asn Ala Gln
                245                 250                 255

Phe Asp Leu Met Ala Arg Thr Pro Tyr Ile Ala Arg His Asn Gly Thr
            260                 265                 270

Pro Leu Leu Gln Ala Ile Ser Asn Ala Leu Asp Pro Asn Ala Thr Ala
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Ser Gly Met Leu Asn Met Arg
305                 310                 315                 320

Trp Thr Leu Pro Gly Gln Pro Asp Asn Thr Pro Pro Gly Gly Ala Leu
                325                 330                 335

Ile Phe Glu Arg Leu Ala Asp Lys Ala Gly Lys Gln Tyr Val Ser Val
            340                 345                 350

Ser Met Val Tyr Gln Thr Leu Glu Gln Leu Arg Ala Gln Thr Pro Leu
        355                 360                 365

Ser Leu Lys Glu Pro Ala Gly Ser Val Gln Leu Lys Ile Pro Gly Cys
    370                 375                 380

Asn Asp Gln Thr Ala Glu Gly Tyr Cys Pro Leu Pro Thr Phe Lys Arg
385                 390                 395                 400

Val Val Ser Gln Ser Glu Glu Pro Gly Cys Gln Leu Gln
                405                 410

<210> SEQ ID NO 19
<211> LENGTH: 413
<212> TYPE: PRT
<213> ORGANISM: Buttiauxella agrestis DSM18931

<400> SEQUENCE: 19

Ser Asp Thr Pro Ala Ser Gly Tyr Gln Ile Glu Lys Val Val Ile Leu
1               5                   10                  15

Ser Arg His Gly Val Arg Ala Pro Thr Lys Met Thr Gln Thr Met Arg

```
            20                  25                  30
Asp Val Thr Pro Asn Ser Trp Pro Glu Trp Pro Val Lys Leu Gly Tyr
        35                  40                  45
Ile Thr Pro Arg Gly Glu His Leu Ile Ser Leu Met Gly Gly Phe Tyr
    50                  55                  60
Arg Gln Lys Phe Gln Gln Lys Gly Ile Leu Ser Gln Gly Ser Cys Pro
65                  70                  75                  80
Thr Pro Asn Ser Ile Tyr Val Trp Ala Asp Val Asp Gln Arg Thr Leu
                85                  90                  95
Lys Thr Gly Glu Ala Phe Leu Ala Gly Leu Ala Pro Gln Cys Gly Leu
            100                 105                 110
Thr Ile His His Gln Gln Asn Leu Glu Lys Ala Asp Pro Leu Phe His
        115                 120                 125
Pro Val Lys Ala Gly Thr Cys Ser Met Asp Lys Thr Gln Val Gln Gln
    130                 135                 140
Ala Val Glu Lys Glu Ala Gln Met Pro Ile Glu Asn Leu Asn Gln His
145                 150                 155                 160
Tyr Ile Pro Ser Leu Ala Leu Met Asn Thr Thr Leu Asn Phe Ser Thr
                165                 170                 175
Ser Ala Trp Cys Gln Lys His Ser Ala Asp Lys Ser Cys Asp Leu Ala
            180                 185                 190
Gln Ser Met Pro Ser Lys Leu Ser Ile Lys Asp Asn Gly Asn Lys Val
        195                 200                 205
Ala Leu Asp Gly Ala Ile Gly Leu Ser Ser Thr Leu Ala Glu Ile Phe
    210                 215                 220
Leu Leu Glu Tyr Ala Gln Gly Met Pro Gln Ala Ala Trp Gly Asn Ile
225                 230                 235                 240
His Ser Glu Gln Glu Trp Ala Ser Leu Leu Lys Leu His Asn Thr Gln
                245                 250                 255
Phe Asp Leu Met Ala Arg Thr Pro Tyr Ile Ala Ala His Asn Gly Thr
            260                 265                 270
Pro Leu Leu Gln Thr Ile Ser Asn Ala Leu Glu Pro Lys Ala Asp Val
        275                 280                 285
Ser Lys Leu Pro Asp Ile Ser Ser Asp Asn Lys Ile Leu Phe Ile Ala
    290                 295                 300
Gly His Asp Thr Asn Ile Ala Asn Ile Ala Gly Met Leu Asn Met Arg
305                 310                 315                 320
Trp Thr Leu Pro Gly Gln Pro Asp Asn Thr Pro Pro Gly Gly Ala Leu
                325                 330                 335
Val Phe Glu Arg Leu Ala Asp Lys Ser Gly Lys Gln Tyr Ile Ser Val
            340                 345                 350
Ser Met Val Tyr Gln Thr Leu Glu Gln Leu Arg Ala Gln Thr Pro Leu
        355                 360                 365
Ser Leu Asn Glu Pro Ala Gly Ser Val Gln Leu Lys Ile Pro Gly Cys
    370                 375                 380
Asn Asp Gln Thr Ala Glu Gly Tyr Cys Pro Leu Ser Thr Phe Thr Arg
385                 390                 395                 400
Val Val Ser Gln Ser Val Glu Pro Gly Cys Gln Leu Pro
                405                 410

<210> SEQ ID NO 20
<211> LENGTH: 413
<212> TYPE: PRT
<213> ORGANISM: Buttiauxella agrestis DSM18932
```

<400> SEQUENCE: 20

```
Asn Asp Thr Pro Ala Ser Gly Tyr Gln Val Glu Lys Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Lys Phe Gln Gln Gln Gly Ile Leu Ser Gln Gly Ser Cys Pro
65              70                  75                  80

Ala Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Thr Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Thr
                165                 170                 175

Ser Ala Trp Cys Gln Lys His Ser Ala Asp Lys Ser Cys Asp Leu Ala
            180                 185                 190

Gln Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Ser Leu Leu Lys Leu His Asn Ala Gln
                245                 250                 255

Phe Asp Leu Met Ala Arg Thr Pro Tyr Ile Ala Thr His Asn Gly Thr
            260                 265                 270

Pro Leu Leu Gln Thr Ile Ser Asn Ala Leu Glu Pro Lys Ala Asp Val
        275                 280                 285

Ser Lys Leu Pro Gly Ile Ser Pro Asp Asn Lys Ile Leu Phe Leu Ala
    290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
```

-continued

```
<210> SEQ ID NO 21
<211> LENGTH: 410
<212> TYPE: PRT
<213> ORGANISM: Peniophora lycii CBS No. 686.96

<400> SEQUENCE: 21

Gln Leu Pro Ile Pro Ala Gln Asn Thr Ser Asn Trp Gly Pro Tyr Asp
1               5                   10                  15

Pro Phe Phe Pro Val Glu Pro Tyr Ala Ala Pro Pro Glu Gly Cys Thr
            20                  25                  30

Val Thr Gln Val Asn Leu Ile Gln Arg His Gly Ala Arg Trp Pro Thr
        35                  40                  45

Ser Gly Ala Arg Ser Arg Gln Val Ala Ala Val Ala Lys Ile Gln Met
    50                  55                  60

Ala Arg Pro Phe Thr Asp Pro Lys Tyr Glu Phe Leu Asn Asp Phe Val
65                  70                  75                  80

Tyr Lys Phe Gly Val Ala Asp Leu Leu Pro Phe Gly Ala Asn Gln Ser
                85                  90                  95

His Gln Thr Gly Thr Asp Met Tyr Thr Arg Tyr Ser Thr Leu Phe Glu
            100                 105                 110

Gly Gly Asp Val Pro Phe Val Arg Ala Ala Gly Asp Gln Arg Val Val
        115                 120                 125

Asp Ser Ser Thr Asn Trp Thr Ala Gly Phe Gly Asp Ala Ser Gly Glu
    130                 135                 140

Thr Val Leu Pro Thr Leu Gln Val Val Leu Gln Glu Gly Asn Cys
145                 150                 155                 160

Thr Leu Cys Asn Asn Met Cys Pro Asn Glu Val Asp Gly Asp Glu Ser
                165                 170                 175

Thr Thr Trp Leu Gly Val Phe Ala Pro Asn Ile Thr Ala Arg Leu Asn
            180                 185                 190

Ala Ala Ala Pro Ser Ala Asn Leu Ser Asp Ser Asp Ala Leu Thr Leu
        195                 200                 205

Met Asp Met Cys Pro Phe Asp Thr Leu Ser Ser Gly Asn Ala Ser Pro
    210                 215                 220

Phe Cys Asp Leu Phe Thr Ala Glu Glu Tyr Val Ser Tyr Glu Tyr Tyr
225                 230                 235                 240

Tyr Asp Leu Asp Lys Tyr Tyr Gly Thr Gly Pro Gly Asn Ala Leu Gly
                245                 250                 255

Pro Val Gln Gly Val Gly Tyr Val Asn Glu Leu Leu Ala Arg Leu Thr
            260                 265                 270

Gly Gln Ala Val Arg Asp Glu Thr Gln Thr Asn Arg Thr Leu Asp Ser
        275                 280                 285

Asp Pro Ala Thr Phe Pro Leu Asn Arg Thr Phe Tyr Ala Asp Phe Ser
    290                 295                 300

His Asp Asn Thr Met Val Pro Ile Phe Ala Ala Leu Gly Leu Phe Asn
305                 310                 315                 320

Ala Thr Ala Leu Asp Pro Leu Lys Pro Asp Glu Asn Arg Leu Trp Val
                325                 330                 335

Asp Ser Lys Leu Val Pro Phe Ser Gly His Met Thr Val Glu Lys Leu
            340                 345                 350

Ala Cys Ser Gly Lys Glu Ala Val Arg Val Leu Val Asn Asp Ala Val
        355                 360                 365
```

```
Gln Pro Leu Glu Phe Cys Gly Gly Val Asp Gly Val Cys Glu Leu Ser
    370                 375                 380

Ala Phe Val Glu Ser Gln Thr Tyr Ala Arg Glu Asn Gly Gln Gly Asp
385                 390                 395                 400

Phe Ala Lys Cys Gly Phe Val Pro Ser Glu
                405                 410

<210> SEQ ID NO 22
<211> LENGTH: 410
<212> TYPE: PRT
<213> ORGANISM: Artificial Sequence
<220> FEATURE:
<223> OTHER INFORMATION: Peniophora variant

<400> SEQUENCE: 22

Gln Leu Pro Ile Pro Ala Gln Asn Thr Ser Asn Trp Gly Pro Tyr Ser
1               5                   10                  15

Pro Phe Phe Pro Val Glu Pro Tyr Ala Ala Pro Pro Glu Gly Cys Thr
                20                  25                  30

Val Thr Gln Val Asn Leu Ile Gln Arg His Gly Ala Arg Trp Pro Thr
            35                  40                  45

Ser Gly Ala Arg Ser Arg Gln Val Ala Ala Val Ala Lys Ile Gln Met
50                  55                  60

Ala Arg Pro Phe Thr Asp Pro Lys Tyr Glu Phe Leu Asn Asp Phe Val
65                  70                  75                  80

Tyr Thr Phe Gly Val Ala Asp Leu Leu Pro Phe Gly Ala Asn Gln Ser
                85                  90                  95

Tyr Gln Thr Gly Thr Asp Met Tyr Thr Arg Tyr Ser Thr Leu Phe Glu
            100                 105                 110

Gly Gly Asp Val Pro Phe Val Arg Ala Ala Gly Asp Gln Arg Val Val
        115                 120                 125

Asp Ser Ser Thr Asn Trp Thr Ala Gly Phe Gly Asp Ala Ser Gly Glu
130                 135                 140

Thr Val Leu Pro Thr Leu Gln Val Val Leu Gln Glu Glu Gly Asn Cys
145                 150                 155                 160

Thr Leu Cys Asn Asn Met Cys Pro Asn Trp Val Lys Gly Asp Glu Ser
                165                 170                 175

Thr Thr Trp Leu Gly Val Phe Ala Pro Asn Ile Thr Ala Arg Leu Asn
            180                 185                 190

Ala Ala Ala Pro Ser Ala Asn Leu Ser Asp Ser Asp Ala Leu Thr Leu
        195                 200                 205

Met Asp Met Cys Pro Phe Asp Thr Leu Ser Ser Gly Asn Ala Ser Pro
210                 215                 220

Phe Cys Asp Leu Phe Thr Ala Glu Glu Tyr Thr Ser Tyr Glu Tyr Tyr
225                 230                 235                 240

Tyr Asp Leu Asp Lys Tyr Tyr Gly Thr Gly Pro Gly Asn Ala Leu Gly
                245                 250                 255

Pro Val Gln Gly Val Gly Tyr Val Asn Glu Leu Leu Ala Arg Leu Thr
            260                 265                 270

Gly Gln Ala Val Arg Asp Glu Thr Gln Thr Asn Arg Thr Leu Asp Ser
        275                 280                 285

Asp Pro Ala Thr Phe Pro Leu Asn Arg Thr Phe Tyr Ala Asp Phe Ser
290                 295                 300

His Asp Asn Thr Met Val Ala Ile Phe Ala Ala Leu Gly Leu Phe Asn
305                 310                 315                 320
```

```
Ala Thr Ala Leu Asp Pro Leu Lys Pro Asp Glu Asn Arg Leu Trp Val
            325                 330                 335

Val Ser Lys Leu Val Pro Phe Ser Gly His Met Thr Val Glu Lys Leu
        340                 345                 350

Ala Cys Ser Gly Lys Glu Ala Val Arg Val Leu Val Asn Asp Ala Val
        355                 360                 365

Gln Pro Leu Glu Phe Cys Gly Val Asp Gly Val Cys Glu Leu Ser
    370                 375                 380

Ala Phe Val Glu Ser Gln Thr Tyr Ala Arg Glu Asn Gly Gln Gly Asp
385                 390                 395                 400

Phe Ala Lys Cys Gly Phe Val Pro Ser Glu
                405                 410

<210> SEQ ID NO 23
<211> LENGTH: 413
<212> TYPE: PRT
<213> ORGANISM: Hafnia alvei

<400> SEQUENCE: 23

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro His Gln Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Ala Asp Val Asp Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Thr Gln Gln Ala Asp Pro Leu Phe His
        115                 120                 125

Pro Val Lys Ala Gly Ile Cys Ser Met Asp Lys Ser Gln Val His Ala
    130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Ala Ile Asn Asp Asp Gly Asn Lys Val
        195                 200                 205

Ala Leu Glu Gly Ala Val Gly Leu Ala Ser Thr Leu Ala Glu Ile Phe
    210                 215                 220

Leu Leu Glu His Ala Gln Gly Met Pro Lys Val Ala Trp Gly Asn Ile
225                 230                 235                 240

His Thr Glu Gln Gln Trp Asn Ser Leu Leu Lys Leu His Asn Ala Gln
                245                 250                 255

Phe Asp Leu Met Ser Arg Thr Pro Tyr Ile Ala Lys His Asn Gly Thr
            260                 265                 270

Pro Leu Leu Gln Thr Ile Ala His Ala Leu Gly Ser Asn Ile Thr Ser
        275                 280                 285
```

```
Arg Pro Leu Pro Asp Ile Ser Pro Asp Asn Lys Ile Leu Phe Ile Ala
        290                 295                 300

Gly His Asp Thr Asn Ile Ala Asn Ile Ser Gly Met Leu Gly Met Thr
305                 310                 315                 320

Trp Thr Leu Pro Gly Gln Pro Asp Asn Thr Pro Pro Gly Gly Ala Leu
                325                 330                 335

Val Phe Glu Arg Trp Val Asp Asn Ala Gly Lys Pro Tyr Val Ser Val
                340                 345                 350

Asn Met Val Tyr Gln Thr Leu Ala Gln Leu His Asp Gln Ala Pro Leu
            355                 360                 365

Thr Leu Gln His Pro Ala Gly Ser Val Arg Leu Asn Ile Pro Gly Cys
        370                 375                 380

Ser Asp Gln Thr Pro Asp Gly Tyr Cys Pro Leu Ser Thr Phe Ser Arg
385                 390                 395                 400

Leu Val Ser His Ser Val Glu Pro Ala Cys Gln Leu Pro
                405                 410

<210> SEQ ID NO 24
<211> LENGTH: 413
<212> TYPE: PRT
<213> ORGANISM: Hafnia sp. LU11047

<400> SEQUENCE: 24

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
            20                  25                  30

Asn Val Thr Pro His Gln Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Ala Asp Val Asp Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Gln Gln Ala Asp Pro Leu Phe His
        115                 120                 125

Pro Val Lys Ala Gly Ile Cys Ser Met Asp Lys Ser Gln Ala His Ala
    130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Ala Ile Asn Asp Asp Gly Asn Lys Val
        195                 200                 205

Ala Leu Glu Gly Ala Val Gly Leu Ser Ser Thr Leu Ala Glu Ile Phe
    210                 215                 220

Leu Leu Glu His Ala Gln Gly Met Pro Lys Val Ala Trp Gly Asn Ile
225                 230                 235                 240

His Thr Glu Gln Gln Trp Asp Ser Leu Leu Lys Leu His Asn Ala Gln
```

```
                        245                 250                 255
Phe Asp Leu Met Ser Arg Thr Pro Tyr Ile Ala Lys His Asn Gly Thr
                    260                 265                 270

Pro Leu Leu Gln Thr Ile Ala His Ala Leu Gly Ser Asn Ile Ala Ser
                275                 280                 285

Arg Pro Leu Pro Asp Ile Ser Pro Asp Asn Lys Ile Leu Phe Ile Ala
            290                 295                 300

Gly His Asp Thr Asn Ile Ala Asn Ile Ser Gly Met Leu Gly Met Thr
305                 310                 315                 320

Trp Thr Leu Pro Gly Gln Pro Asp Asn Thr Pro Pro Gly Gly Ala Leu
                325                 330                 335

Val Phe Glu Arg Trp Val Asp Asn Ala Gly Lys Pro Tyr Val Ser Val
                340                 345                 350

Asn Met Val Tyr Gln Thr Leu Ala Gln Leu His Asp Gln Thr Pro Leu
                355                 360                 365

Thr Leu Gln His Pro Ala Gly Ser Val Arg Leu Asn Ile Pro Gly Cys
            370                 375                 380

Ser Asp Gln Thr Pro Asp Gly Tyr Cys Pro Leu Ser Thr Phe Ser Arg
385                 390                 395                 400

Leu Val Asn His Ser Val Glu Pro Ala Cys Gln Leu Pro
                405                 410
```

<210> SEQ ID NO 25
<211> LENGTH: 414
<212> TYPE: PRT
<213> ORGANISM: Artificial Sequence
<220> FEATURE:
<223> OTHER INFORMATION: Hafnia variant

<400> SEQUENCE: 25

```
Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
                20                  25                  30

Asn Val Thr Pro His Gln Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Ala Asp Val Asp Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Asn Ile Gln Gln Ala Asp Pro Leu Phe His
        115                 120                 125

Pro Val Lys Ala Gly Ile Cys Ser Met Asp Lys Ser Gln Ala His Ala
            130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Ala Ile Asn Asp Asp Gly Asn Lys Val
```

```
                195                 200                 205
Ala Leu Glu Gly Ala Val Gly Leu Ser Ser Thr Leu Ala Glu Ile Phe
210                 215                 220

Leu Leu Glu His Ala Gln Gly Met Pro Lys Val Ala Trp Gly Asn Ile
225                 230                 235                 240

His Thr Glu Gln Gln Trp Asp Ser Leu Leu Lys Leu His Asn Ala Gln
                245                 250                 255

Phe Asp Leu Met Ser Arg Thr Pro Tyr Ile Ala Lys His Asn Gly Thr
            260                 265                 270

Pro Leu Leu Gln Thr Ile Ala His Ala Leu Gly Ser Asn Ile Ala Ser
        275                 280                 285

Arg Pro Leu Pro Asp Ile Ser Pro Asp Asn Lys Ile Leu Phe Ile Ala
    290                 295                 300

Gly His Asp Thr Asn Ile Ala Asn Ile Ser Gly Met Leu Gly Met Thr
305                 310                 315                 320

Trp Thr Leu Pro Gly Gln Pro Asp Asn Thr Pro Pro Gly Gly Leu
                325                 330                 335

Val Phe Glu Leu Trp Gln Asn Pro Asp Asn His Gln Gln Tyr Val Ala
            340                 345                 350

Val Lys Met Phe Tyr Gln Thr Met Asp Gln Leu Arg Asn Ser Glu Lys
        355                 360                 365

Leu Asp Leu Lys Ser His Pro Ala Gly Ile Val Pro Ile Glu Ile Glu
    370                 375                 380

Gly Cys Glu Asn Ile Gly Thr Asp Lys Leu Cys Gln Leu Asp Thr Phe
385                 390                 395                 400

Gln Lys Arg Val Ala Gln Val Ile Glu Pro Ala Cys His Ile
                405                 410

<210> SEQ ID NO 26
<211> LENGTH: 414
<212> TYPE: PRT
<213> ORGANISM: Artificial Sequence
<220> FEATURE:
<223> OTHER INFORMATION: Hafnia variant

<400> SEQUENCE: 26

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro His Gln Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Thr Asp Val Asn Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Thr Gln Val Asp Pro Leu Phe His
        115                 120                 125

Pro Val Lys Ala Gly Ile Cys Ser Met Asn Lys Ser Gln Thr Tyr Glu
    130                 135                 140

Ala Val Glu Lys Gln Ala Gly Gly Pro Ile Glu Thr Leu Asn Gln Arg
```

```
                145                 150                 155                 160
Tyr Gln Ala Glu Leu Ala Leu Met Ser Ser Val Leu Asp Phe Pro Lys
                165                 170                 175
Ser Pro Tyr Cys Gln Gln His Asn Ile Gly Lys Leu Cys Asp Phe Ser
            180                 185                 190
Gln Ala Met Pro Ser Arg Leu Asn Ile Ser Asp Asp Gly Asn Glu Val
        195                 200                 205
Gln Leu Glu Gly Ala Val Gly Leu Gly Ser Thr Leu Ala Glu Ile Phe
    210                 215                 220
Leu Leu Glu Tyr Ala Gln Gly Met Pro Val Val Ala Trp Gly Asn Ile
225                 230                 235                 240
His Asn Glu Ser Gln Trp Lys Ser Leu Leu Asn Leu His Asn Ala His
                245                 250                 255
Phe Asn Leu Met His Arg Thr Pro Tyr Ile Ala Lys His Gln Gly Thr
            260                 265                 270
Pro Leu Leu Gln Ala Ile Ser Asn Ala Leu Asn Pro Asn Ala Thr Glu
        275                 280                 285
Ser Lys Leu Pro Asp Ile Ser Pro Asp Asn Lys Ile Leu Phe Ile Ala
    290                 295                 300
Gly His Asp Thr Asn Ile Ala Asn Ile Gly Gly Met Leu Gly Met Asn
305                 310                 315                 320
Trp Thr Leu Pro Gly Gln Pro Asp Asn Thr Pro Pro Gly Gly Gly Leu
                325                 330                 335
Val Phe Glu Leu Trp Gln Asn Pro Asp Asn His Gln Gln Tyr Val Ala
            340                 345                 350
Val Lys Met Ile Tyr Gln Thr Met Asp Gln Leu Arg Asn Ser Glu Lys
        355                 360                 365
Leu Asp Leu Lys Ser Asn Pro Ala Gly Ile Val Pro Ile Glu Ile Glu
    370                 375                 380
Gly Cys Glu Asn Ile Gly Thr Asp Lys Leu Cys Gln Leu Asp Thr Phe
385                 390                 395                 400
Gln Lys Arg Val Ala Gln Val Ile Glu Pro Ala Cys Gln Ile
                405                 410

<210> SEQ ID NO 27
<211> LENGTH: 213
<212> TYPE: PRT
<213> ORGANISM: Artificial Sequence
<220> FEATURE:
<223> OTHER INFORMATION: Wild type sequence with N-terminal SPIRR

<400> SEQUENCE: 27

Ser Pro Ile Arg Arg Ile Pro Gly Phe Asp Ile Ser Gly Trp Gln
1               5                   10                  15

Pro Thr Thr Asp Phe Ala Arg Ala Tyr Ala Asn Gly Asp Arg Phe Val
            20                  25                  30

Tyr Ile Lys Ala Thr Glu Gly Thr Phe Lys Ser Ser Ala Phe Ser
        35                  40                  45

Arg Gln Tyr Thr Gly Ala Thr Gln Asn Gly Phe Ile Arg Gly Ala Tyr
    50                  55                  60

His Phe Ala Gln Pro Ala Ser Ser Gly Ala Gln Ala Arg Tyr
65                  70                  75                  80

Phe Ala Ser Asn Gly Gly Gly Trp Ser Lys Asp Gly Ile Thr Leu Pro
                85                  90                  95

Gly Ala Leu Asp Ile Glu Tyr Asn Pro Asn Gly Ala Thr Cys Tyr Gly
```

```
            100             105              110
Leu Ser Gln Ser Ala Met Val Asn Trp Ile Glu Asp Phe Val Thr Thr
        115                 120                 125

Tyr His Gly Ile Thr Ser Arg Trp Pro Val Ile Tyr Thr Thr Thr Asp
    130                 135                 140

Trp Trp Thr Gln Cys Thr Gly Asn Ser Asn Arg Phe Ala Asn Arg Cys
145                 150                 155                 160

Pro Leu Trp Ile Ala Arg Tyr Ala Ser Ser Val Gly Thr Leu Pro Asn
                165                 170                 175

Gly Trp Gly Phe Tyr Thr Phe Trp Gln Tyr Asn Asp Lys Tyr Pro Gln
            180                 185                 190

Gly Gly Asp Ser Asn Trp Phe Asn Gly Asp Ala Ser Arg Leu Arg Ala
        195                 200                 205

Leu Ala Asn Gly Asp
    210

<210> SEQ ID NO 28
<211> LENGTH: 129
<212> TYPE: PRT
<213> ORGANISM: gallus gallus

<400> SEQUENCE: 28

Lys Val Phe Gly Arg Cys Glu Leu Ala Ala Ala Met Lys Arg His Gly
1               5                   10                  15

Leu Asp Asn Tyr Arg Gly Tyr Ser Leu Gly Asn Trp Val Cys Ala Ala
            20                  25                  30

Lys Phe Glu Ser Asn Phe Asn Thr Gln Ala Thr Asn Arg Asn Thr Asp
        35                  40                  45

Gly Ser Thr Asp Tyr Gly Ile Leu Gln Ile Asn Ser Arg Trp Trp Cys
    50                  55                  60

Asn Asp Gly Arg Thr Pro Gly Ser Arg Asn Leu Cys Asn Ile Pro Cys
65                  70                  75                  80

Ser Ala Leu Leu Ser Ser Asp Ile Thr Ala Ser Val Asn Cys Ala Lys
                85                  90                  95

Lys Ile Val Ser Asp Gly Asn Gly Met Asn Ala Trp Val Ala Trp Arg
            100                 105                 110

Asn Arg Cys Lys Gly Thr Asp Val Gln Ala Trp Ile Arg Gly Cys Arg
        115                 120                 125

Leu

<210> SEQ ID NO 29
<211> LENGTH: 218
<212> TYPE: PRT
<213> ORGANISM: Aspergillus fumigatus

<400> SEQUENCE: 29

Leu Pro Ser Gln Pro Glu Ala Arg Ala Thr Thr Val Gln Gly Phe Asp
1               5                   10                  15

Ile Ser Asn His Gln Lys Ser Val Asn Phe Glu Ala Ala Lys Lys Asp
            20                  25                  30

Gly Ala Gln Phe Val Met Ile Lys Ala Thr Glu Gly Thr Thr Tyr Lys
        35                  40                  45

Asp Thr Val Phe Asn Ser His Tyr Thr Gly Ala Thr Lys Ala Gly Leu
    50                  55                  60

Leu Arg Gly Gly Tyr His Phe Ala Arg Pro Asp Lys Ser Thr Gly Ser
65                  70                  75                  80
```

```
Thr Gln Ala Lys Phe Phe Leu Lys Asn Gly Gly Trp Ser Asp Asp
                85                  90                  95

Asn Arg Thr Leu Pro Gly Met Leu Asp Ile Glu Tyr Asn Pro Tyr Gly
            100                 105                 110

Ala Thr Cys Tyr Gly Leu Ser His Ser Gln Met Val Ala Trp Ile His
            115                 120                 125

Asp Phe Val Asn Glu Tyr His His Ala Thr Ser Arg Trp Pro Met Ile
130                 135                 140

Tyr Thr Thr Ala Asp Trp Trp Asn Arg Cys Thr Gly Asn Ala Lys Gly
145                 150                 155                 160

Phe Gly Asp Lys Cys Pro Leu Val Leu Ala Ala Tyr Ser Ser Ser Pro
                165                 170                 175

Pro Lys Thr Ile Pro Gly Asp Trp Lys Thr Trp Thr Ile Trp Gln Asn
            180                 185                 190

Ser Asp Lys Tyr Lys His Gly Gly Asp Ser Asp Lys Phe Asn Gly Pro
            195                 200                 205

Met Thr Gln Leu Arg Lys Leu Ala Ser Gly
210                 215

<210> SEQ ID NO 30
<211> LENGTH: 208
<212> TYPE: PRT
<213> ORGANISM: Acremonium alcalophilum

<400> SEQUENCE: 30

Arg Ile Pro Gly Phe Asp Ile Ser Gly Trp Gln Pro Thr Thr Asp Phe
1               5                   10                  15

Ala Arg Ala Tyr Ala Asn Gly Asp Arg Phe Val Tyr Ile Lys Ala Thr
                20                  25                  30

Glu Gly Thr Thr Phe Lys Ser Ser Ala Phe Ser Arg Gln Tyr Thr Gly
            35                  40                  45

Ala Thr Gln Asn Gly Phe Ile Arg Gly Ala Tyr His Phe Ala Gln Pro
        50                  55                  60

Ala Ala Ser Ser Gly Ala Ala Gln Ala Arg Tyr Phe Ala Ser Asn Gly
65                  70                  75                  80

Gly Gly Trp Ser Lys Asp Gly Ile Thr Leu Pro Gly Ala Leu Asp Ile
                85                  90                  95

Glu Tyr Asn Pro Asn Gly Ala Thr Cys Tyr Gly Leu Ser Gln Ser Ala
            100                 105                 110

Met Val Asn Trp Ile Glu Asp Phe Val Thr Thr Tyr His Gly Ile Thr
            115                 120                 125

Ser Arg Trp Pro Val Ile Tyr Thr Thr Thr Asp Trp Trp Thr Gln Cys
        130                 135                 140

Thr Gly Asn Ser Asn Arg Phe Ala Asn Arg Cys Pro Leu Trp Ile Ala
145                 150                 155                 160

Arg Tyr Ala Ser Ser Val Gly Thr Leu Pro Asn Gly Trp Gly Phe Tyr
                165                 170                 175

Thr Phe Trp Gln Tyr Asn Asp Lys Tyr Pro Gln Gly Gly Asp Ser Asn
            180                 185                 190

Trp Phe Asn Gly Asp Ala Ser Arg Leu Arg Ala Leu Ala Asn Gly Asp
            195                 200                 205

<210> SEQ ID NO 31
<211> LENGTH: 17
<212> TYPE: DNA
```

```
<213> ORGANISM: Artificial Sequence
<220> FEATURE:
<223> OTHER INFORMATION: forward primer 341F
<220> FEATURE:
<221> NAME/KEY: misc_feature
<222> LOCATION: (9)..(9)
<223> OTHER INFORMATION: n is a, c, g, or t

<400> SEQUENCE: 31
cctacgggng gcwgcag                                                   17

<210> SEQ ID NO 32
<211> LENGTH: 21
<212> TYPE: DNA
<213> ORGANISM: Artificial Sequence
<220> FEATURE:
<223> OTHER INFORMATION: reverse primer 805R

<400> SEQUENCE: 32
gactachvgg gtatctaatc c                                              21

<210> SEQ ID NO 33
<211> LENGTH: 440
<212> TYPE: DNA
<213> ORGANISM: Faecalibacterium sp.

<400> SEQUENCE: 33
cctacggggg gctgcagtgg ggaatattgc acaatggggg aaaccctgat gcagcgacgc    60
cgcgtggagg aagaaggtct tcggattgta aactcctgtt gttggggaaa agaaggatgg   120
tacccaacaa ggaagtgacg gctaactacg tgccagcagc cgcggtaaaa cgtaggtcac   180
gagcgttgtc cggaattact gggtgtaaag ggagcgcagg cgggtatgca agttgggagt   240
gaaatacatg gctcaaccc atgaactgct ctcaaaactg tgtatcttga gtagtgcaga    300
ggtaggcgga attcccggtg tagcggtgga atgcgtagat atcggagga acaccagtgg    360 cgaaggcggc ctactgggca ccaactgacg ctgaggctcg aaagtgtggg tagcaaacag   420
gattagatac cccagtagtc                                               440

<210> SEQ ID NO 34
<211> LENGTH: 440
<212> TYPE: DNA
<213> ORGANISM: Faecalibacterium sp.

<400> SEQUENCE: 34
cctacggggg gctgcagtgg ggaatattgc acaatggagg aaactctgat gcagcgacgc    60
cgcgtggagg aagaaggtct tcggattgta aactcctgtt gttgaggacg ataatgacgg   120
tactcaacaa ggaagtgacg gctaactacg tgccagcagc cgcggtaaaa cgtaggtcac   180
aagcgttgtc cggaattact gggtgtaaag ggagcgcagg cgggaatgca agttgggagt   240
gaaatctacg gctcaaccc gtaaactgct ctcaaaactg tatttcttga gtagtgcaga    300
ggtaggcgga attcccggtg tagcggtgga atgcgtagat atcggagga acaccagtgg   360 cgaaggcggc ctactgggca ccaactgacg ctgaggctcg aaagtgtggg tagcaaacag   420
gattagatac cccagtagtc                                               440

<210> SEQ ID NO 35
<211> LENGTH: 440
<212> TYPE: DNA
<213> ORGANISM: Faecalibacterium sp.

<400> SEQUENCE: 35
```

```
cctacgggag gcagcagtgg ggaatattgc acaatggggg aaaccctgat gcagcgacgc    60
cgcgtggagg aagaaggtct tcggattgta aactcctgtt gttagggaaa atcgagatgg   120
tacctaacaa ggaagtgacg gctaactacg tgccagcagc cgcggtaaaa cgtaggtcac   180
aagcgttgtc cggaattact gggtgtaaag ggagcgcagg cgggtatgca agttggaagt   240
gaaatacatg ggctcaaccc atgaactgct ttcaaaactg tgtatcttga gtagtgcaga   300
ggtaggcgga attcccggtg tagcggtgga atgcgtagat atcggagga acaccagtgg   360 cgaaggcggc ctactgggta ccaactgacg ctgaggctcg aaagtgtggg tagcaaacag   420
gattagatac ccgggtagtc                                               440
```

<210> SEQ ID NO 36
<211> LENGTH: 440
<212> TYPE: DNA
<213> ORGANISM: Faecalibacterium sp.

<400> SEQUENCE: 36

```
cctacggggg gctgcagtgg ggaatattgc acaatggggg aaaccctgat gcagcgacgc    60
cgcgtggagg aagaaggtct tcggattgta aactcctgtt gttggggaaa agaaggatgg   120
tacccaacaa ggaagtgacg gctaactacg tgccagcagc cgcggtaaaa cgtaggtcac   180
gagcgttgtc cggaattact gggtgtaaag ggagcgcagg cggaccggca agttggaagt   240
gaaatctatg ggctcaaccc ataaattgct ttcaaaactg ctggccttga gtagtgcaga   300
ggtaggtgga attcccggtg tagcggtgga atgcgtagat atcggagga acaccagtgg   360 cgaaggcggc ctactgggca ccaactgacg ctgaggctcg aaagtgtggg tagcaaacag   420
gattagatac cccagtagtc                                               440
```

<210> SEQ ID NO 37
<211> LENGTH: 440
<212> TYPE: DNA
<213> ORGANISM: Faecalibacterium sp.

<400> SEQUENCE: 37

```
cctacggggg gctgcagtgg ggaatattgc acaatggggg aaaccctgat gcagcgacgc    60
cgcgtggagg aagaaggtct tcggattgta aactcctgtt gttggggaaa agaaggatgg   120
tacccaacaa ggaagtgacg gctaactacg tgccagcagc cgcggtaaaa cgtaggtcac   180
gagcgttgtc cggaattact gggtgtaaag ggagcgcagg cggattggta agttggaggt   240
gaaattcatg ggctcaaccc atgacctgcc ttcaaaacta ccagtcttga gtggtgcaga   300
ggtaggcgga attcccggtg tagcggtgga atgcgtagat atcgggagga acaccagtgg   360
cgaaggcggc ctactgggca ccaactgacg ctgaggctcg aaagtgtggg tagcaaacag   420
gattagatac cccagtagtc                                               440
```

<210> SEQ ID NO 38
<211> LENGTH: 440
<212> TYPE: DNA
<213> ORGANISM: Faecalibacterium sp.

<400> SEQUENCE: 38

```
cctacggggg gctgcagtgg ggaatattgc acaatggggg aaaccctgat gcagcgacgc    60
cgcgtggagg aagaaggtct tcggattgta aactcctgtt gttggggaaa agaaggatgg   120
tacccaacaa ggaagtgacg gctaactacg tgccagcagc cgcggtaaaa cgtaggtcac   180
```

```
gagcgttgtc cggaattact gggtgtaaag ggagcgcagg cgggtatgca agttgggagt    240
gaaatcccgg ggcttaactc cggaactgct ttcaaaactg ctggtcttga gtgatggaga    300
ggcaggcgga attccgtgtg tagcggtgaa atgcgtagat attaggagga acaccagtgg    360
cgaaggcggc ctactgggca ccaactgacg ctgaggctcg aaagtgtggg tagcaaacag    420
gattagatac ccctgtagtc                                                440
```

<210> SEQ ID NO 39
<211> LENGTH: 440
<212> TYPE: DNA
<213> ORGANISM: Faecalibacterium sp.

<400> SEQUENCE: 39

```
cctacgggag gcagcagtgg ggaatattgc acaatggggg aaaccctgat gcagcgacgc     60
cgcgtggagg aagaaggtct tcggattgta aactcctgtt gttggggaaa agaaggatgg    120
tacccaacaa ggaagtgacg gctaactacg tgccagcagc cgcggtaaaa cgtaggtcac    180
gagcgttgtc cggaattact gggtgtaaag ggagcgcagg cgggtcggca agttggaggt    240
gaaagctgtg ggctcaactc acaaactgcc ttcaaaactg ccggtcttga gtggtgtaga    300
ggtaggcgga attcccggtg tagcggtgga atgcgtagat atcgggagga acaccagtgg    360
cgaaggcggc ctactgggca ccaactgacg ctgaggctcg aaagtgtggg tagcaaacag    420
gattagatac ccttgtagtc                                                440
```

<210> SEQ ID NO 40
<211> LENGTH: 440
<212> TYPE: DNA
<213> ORGANISM: Faecalibacterium sp.

<400> SEQUENCE: 40

```
cctacgggg gctgcagtgg ggaatattgc acaatggggg aaaccctgat gcagcgacgc     60
cgcgtggagg aagaaggtct tcggattgta aactcctgtt gttggggaaa agaaggatgg    120
tacccaacaa ggaagtgacg gctaactacg tgccagcagc cgcggtaaaa cgtaggtcac    180
gagcgttgtc cggaattact gggtgtaaag ggtgcgtagg cggctcggca agtcagaggt    240
gaaatccatg ggcttaaccc atgaactgcc tttgaaactg tcgaacttga gtgaagtaga    300
ggtaggcgga attcccggtg tagcggtgga atgcgtagat atcgggagga acaccagtgg    360
cgaaggcggc ctactgggca ccaactgacg ctgaggctcg aaagtgtggg tagcaaacag    420
gattagatac ccctgtagtc                                                440
```

<210> SEQ ID NO 41
<211> LENGTH: 440
<212> TYPE: DNA
<213> ORGANISM: Faecalibacterium sp.

<400> SEQUENCE: 41

```
cctacgggg gctgcagtgg ggaatattgc acaatggggg aaaccctgat gcagcgacgc     60
cgcgtggagg aagaaggtct tcggattgta aactcctgtt gttggggaaa agaggatgg    120 tacccaacaa ggaagtgacg gctaactacg tgccagcagc cgcggtaaaa cgtaggtcac    180
aagcgttgtc cggaattact gggtgtaaag ggcgtgtagg cgggaaggca agtcagacgt    240
gaaaaccacg ggctcaacct gtggcctgcg tttgagactg ttttttcttga gtagtgcaga    300 ggtaggcgga attcccggtg tagcggtgga atgcgtagat atcgggagga acaccagtgg    360
cgaaggcggc ctactgggca ccaactgacg ctgaggctcg aaagtgtggg tagcaaacag    420
```

```
gattagatac cccggtagtc                                           440
```

<210> SEQ ID NO 42
<211> LENGTH: 440
<212> TYPE: DNA
<213> ORGANISM: Faecalibacterium sp.

<400> SEQUENCE: 42

```
cctacgggtg gcagcagtgg ggaatattgc acaatggggg aaaccctgat gcagcgacgc   60
cgcgtggagg aagaaggtct tcggattgta aactcctgtt gttagggaaa atcgagatgg  120
tacctaacaa ggaagtgacg gctaactacg tgccagcagc cgcggtaaaa cgtaggtcac  180
aagcgttgtc cggaattact gggtgtaaag ggcgagtagg cgggctggta agttggaagt  240
gaaatcccgg ggcttaaccc cggaactgct ttcaaaactg tgtatcttga gtagtgcaga  300
ggtaggcgga attcccggtg tagcggtgga atgcgtagat atcgggagga acaccagtgg  360
cgaaggcggc ctactgggca ccaactgacg ctgaggctcg aaagtgtggg tagcaaacag  420
gattagatac ccttgtagtc                                           440
```

<210> SEQ ID NO 43
<211> LENGTH: 440
<212> TYPE: DNA
<213> ORGANISM: Faecalibacterium sp.

<400> SEQUENCE: 43

```
cctacggggg gctgcagtgg ggaatattgc acaatggggg aaaccctgat gcagcgacgc   60
cgcgtggagg aagaaggtct tcggattgta aactcctgtt gttggggaaa agaaggatgg  120
tacccaacaa ggaagtgacg gctaactacg tgccagcagc cgcggtaaaa cgtaggtcac  180
gagcgttgtc cggaattact gggtgtaaag ggagcgcagg cgggtatgca agttgggagt  240
gaaatacatg ggctcaaccc atgaactgct ctcaaaactg tgtatcttga gtagtgcaga  300
ggtaggcgga attcccggtg tagcggtgga atgcgtagat atcgggagga acaccagtgg  360
cgaaggcggc ctactgggca ccaactgacg ctgaggctcg aaagtgtggg tagcaaacag  420
gattagatac cccagtagtc                                           440
```

<210> SEQ ID NO 44
<211> LENGTH: 440
<212> TYPE: DNA
<213> ORGANISM: Faecalibacterium sp.

<400> SEQUENCE: 44

```
cctacggggg gctgcagtgg ggaatattgc acaatggagg aaactctgat gcagcgacgc   60
cgcgtggagg aagaaggtct tcggattgta aactcctgtt gttgaggacg ataatgacgg  120
tactcaacaa ggaagtgacg gctaactacg tgccagcagc cgcggtaaaa cgtaggtcac  180
aagcgttgtc cggaattact gggtgtaaag ggagcgcagg cgggaatgca agttgggagt  240
gaaatctacg ggctcaaccc gtaaactgct ctcaaaactg tatttcttga gtagtgcaga  300
ggtaggcgga attcccggtg tagcggtgga atgcgtagat atcgggagga acaccagtgg  360
cgaaggcggc ctactgggca ccaactgacg ctgaggctcg aaagtgtggg tagcaaacag  420
gattagatac cccagtagtc                                           440
```

<210> SEQ ID NO 45
<211> LENGTH: 440
<212> TYPE: DNA

<213> ORGANISM: Faecalibacterium sp.

<400> SEQUENCE: 45

```
cctacggggg gctgcagtgg ggaatattgc acaatggggg aaaccctgat gcagcgacgc    60
cgcgtggagg aagaaggtct tcggattgta aactcctgtt gttggggaaa agaaggatgg   120
tacccaacaa ggaagtgacg gctaactacg tgccagcagc cgcggtaaaa cgtaggtcac   180
gagcgttgtc cggaattact gggtgtaaag ggagcgcagg cgggctgtca agttggaagt   240
gaaatctatg ggctcaaccc ataaattgct ttcaaaactg atggtcttga gtagtgcaga   300
ggtaggcgga attcccggtg tagcggtgga atgcgtagat atcggagga acaccagtgg   360
cgaaggcggc ctactgggca ccaactgacg ctgaggctcg aaagtgtggg tagcaaacag   420
gattagatac cccagtagtc                                               440
```

<210> SEQ ID NO 46
<211> LENGTH: 440
<212> TYPE: DNA
<213> ORGANISM: Faecalibacterium sp.

<400> SEQUENCE: 46

```
cctacgggag gcagcagtgg ggaatattgc acaatggggg aaaccctgat gcagcgacgc    60
cgcgtggagg aagaaggtct tcggattgta aactcctgtt gttgaggaag aaaaggacgg   120
tactcaacaa ggaagtgacg gctaactacg tgccagcagc cgcggtaaaa cgtaggtcac   180
gagcgttgtc cggaattact gggtgtaaag ggagcgcagg cgggtagaca agttgggagt   240
gaaatgcatg ggctcaaccc atgaactgct ctcaaaactg tagatcttga gtagtgcaga   300
ggtaggcgga attcccggtg tagcggtgga atgcgtagat atcggagga acaccagtgg   360
cgaaggcggc ctactgggca ccaactgacg ctgaggctcg aaagtgtggg tagcaaacag   420
gattagatac ccgtgtagtc                                               440
```

<210> SEQ ID NO 47
<211> LENGTH: 440
<212> TYPE: DNA
<213> ORGANISM: Faecalibacterium sp.

<400> SEQUENCE: 47

```
cctacgggag gctgcagtgg ggaatattgc acaatggggg aaaccctgat gcagcgacgc    60
cgcgtggagg aagaaggtct tcggattgta aactcctgtt gttggggaaa agaaggatgg   120
tacccaacaa ggaagtgacg gctaactacg tgccagcagc cgcggtaaaa cgtaggtcac   180
gagcgttgtc cggaattact gggtgtaaag ggagcgcagg cggattggta agttggaggt   240
gaaattcatg ggctcaaccc atgacctgcc ttcaaaacta ccagtcttga gtggtgcaga   300
ggtaggcgga attcccggtg tagcggtgga atgcgtagat atcggagga acaccagtgg   360
cgaaggcggc ctactgggca ccaactgacg ctgaggctcg aaagtgtggg tagcaaacag   420
gattagatac ccctgtagtc                                               440
```

<210> SEQ ID NO 48
<211> LENGTH: 440
<212> TYPE: DNA
<213> ORGANISM: Faecalibacterium sp.

<400> SEQUENCE: 48

```
cctacgggcg gctgcagtgg ggaatattgc acaatggggg aaaccctgat gcagcgacgc    60
cgcgtggagg aagaaggtct tcggattgta aactcctgtt gttggggaaa agaaggatgg   120
```

```
tacccaacaa ggaagtgacg gctaactacg tgccagcagc cgcggtaaaa cgtaggtcac    180
gagcgttgtc cggaattact gggtgtaaag ggagtgcagg cggacgcca agttggaagt    240 gaaacccatg gcttaaccc atgaactgct ttcaaaactg tcgttcttga gtggtgcaga    300
ggtaggcgga attcccggtg tagcggtgga atgcgtagat atcgggagga acaccagtgg    360
cgaaggcggc ctactgggca ccaactgacg ctgaggctcg aaagtgtggg tagcaaacag    420
gattagatac ccctgtagtc                                                 440

<210> SEQ ID NO 49
<211> LENGTH: 440
<212> TYPE: DNA
<213> ORGANISM: Faecalibacterium sp.

<400> SEQUENCE: 49
cctacggggg gctgcagtgg ggaatattgc acaatggggg aaaccctgat gcagcgacgc    60
cgcgtggagg aagaaggtct tcggattgta aactcctgtt gttggggaaa agaaggatgg    120
tacccaacaa ggaagtgacg gctaactacg tgccagcagc cgcggtaaaa cgtaggtggc    180
aagcgttgtc cggaattact gggtgtaaag ggagcgcagg cgggtcggca agttggaggt    240
gaaagctgtg ggctcaactc acaaactgcc ttcaaaactg ccggtcttga gtggtgtaga    300
ggtaggcgga attcccggtg tagcggtgga atgcgtagat atcgggagga acaccagtgg    360
cgaaggcggc ctactgggca ccaactgacg ctgaggctcg aaagtgtggg tagcaaacag    420
gattagatac ccttgtagtc                                                 440

<210> SEQ ID NO 50
<211> LENGTH: 440
<212> TYPE: DNA
<213> ORGANISM: Faecalibacterium sp.

<400> SEQUENCE: 50
cctacgggag gcagcagtgg ggaatattgc acaatggggg aaaccctgat gcagcgacgc    60
cgcgtggagg aagaaggtct tcggattgta aactcctgtt gttggggaaa agaaggatgg    120
tacccaacaa ggaagtgacg gctaactacg tgccagcagc cgcggtaaaa cgtaggtcac    180
gagcgttgtc cggaattact gggtgtaaag ggagcgcagg cgggaatgca agttgggagt    240
gaaatctacg gctcaaccc gtaaactgct ctcaaaactg tatttcttga gtagtgcaga    300
ggtaggcgga attcccggtg tagcggtgga atgcgtagat atcgggagga acaccagtgg    360
cgaaggcggc ctactgggca ccaactgacg ctgaggctcg aaagcatggg tagcgaacag    420
gattagatac ccgagtagtc                                                 440

<210> SEQ ID NO 51
<211> LENGTH: 440
<212> TYPE: DNA
<213> ORGANISM: Faecalibacterium sp.

<400> SEQUENCE: 51
cctacgggtg gcagcagtgg ggaatattgc acaatggggg aaaccctgat gcagcgacgc    60
cgcgtggagg aagaaggtct tcggattgta aactcctgtt gttagggaaa atcgagatgg    120
tacctaacaa ggaagtgacg gctaactacg tgccagcagc cgcggtaaaa cgtaggtcac    180
aagcgttgtc cggaattact gggtgtaaag ggagcgcagg cgggtatgca agttggaagt    240
gaaatacatg gctcaaccc atgaactgct ttcaaaactg tgtatcttga gtagtgcaga    300
```

```
ggtaggcgga attcccggtg tagcggtgga atgcgtagat atcgggagga acaccagtgg    360
cgaaggcggc ctactgggta ccaactgacg ctgaggctcg aaagtgtggg tagcaaacag    420
gattagatac ccttgtagtc                                                440
```

```
<210> SEQ ID NO 52
<211> LENGTH: 444
<212> TYPE: DNA
<213> ORGANISM: Faecalibacterium sp.

<400> SEQUENCE: 52 cctacgggg gctgcagtgg ggaatattgc acaatgggg aaaccctgat gcagcgacgc      60
cgcgtggagg aagaaggtct tcggattgta aactgttgtc gcgagggaag aaggaagatg   120
acggtacctc gtgagaaagt cacggctaac tacgtgccag cagccgcggt aaaacgtagg   180
tcacgagcgt tgtccggaat tactgggtgt aaagggagcg caggcgggta tgcaagttgg   240
gagtgaaata catgggctca acccatgaac tgctctcaaa actgtgtatc ttgagtagtg   300
cagaggtagg cggaattccc ggtgtagcgg tggaatgcgt agatatcggg aggaacacca   360
gtggcgaagg cggcctactg ggcaccaact gacgctgagg ctcgaaagtg tgggtagcaa   420
acaggattag ataccctgt agtc                                            444
```

```
<210> SEQ ID NO 53
<211> LENGTH: 443
<212> TYPE: DNA
<213> ORGANISM: Faecalibacterium sp.

<400> SEQUENCE: 53 cctacgggg gctgcagtgg ggaatattgc acaatgggg aaaccctgat gcagcgacgc      60
cgcgtggagg aagaaggtct tcggattgta aacttctgta gacagggacg aagaaagtga   120
cggtacctgt aaagtaagcc acggctaact acgtgccagc agccgcggta aaacgtaggt   180
cacgagcgtt gtccggaatt actgggtgta aaggagcgc aggcgggtat gcaagttggg   240
agtgaaatac atgggctcaa cccatgaact gctctcaaaa ctgtgtatct tgagtagtgc   300
agaggtaggc ggaattcccg gtgtagcggt ggaatgcgta gatatcggga ggaacaccag   360
tggcgaaggc ggcctactgg gcaccaactg acgctgaggc tcgaaagtgt gggtagcaaa   420
caggattaga taccccagta gtc                                            443
```

```
<210> SEQ ID NO 54
<211> LENGTH: 443
<212> TYPE: DNA
<213> ORGANISM: Faecalibacterium sp.

<400> SEQUENCE: 54 cctacgggg gcagcagtgg ggaatattgc acaatgggg aaaccctgat gcagcgacgc      60
cgcgtggagg aagaaggtct tcggattgta aagttctgtg acggggacg aacacaatga   120 cggtaccccg atagcaagcc acggctaact acgtgccagc agccgcggta aaacgtaggt   180
cacgagcgtt gtccggaatt actgggtgta aaggagcgc aggcgggtat gcaagttggg   240
agtgaaatac atgggctcaa cccatgaact gctctcaaaa ctgtgtatct tgagtagtgc   300
agaggtaggc ggaattcccg gtgtagcggt ggaatgcgta gatatcggga ggaacaccag   360
tggcgaaggc ggcctactgg gcaccaactg acgctgaggc tcgaaagtgt gggtagcaaa   420
caggattaga taccccagta gtc                                            443
```

UNITED STATES PATENT AND TRADEMARK OFFICE
CERTIFICATE OF CORRECTION

PATENT NO. : 10,959,942 B2
APPLICATION NO. : 15/580081
DATED : March 30, 2021
INVENTOR(S) : Sandvang et al.

Page 1 of 1

It is certified that error appears in the above-identified patent and that said Letters Patent is hereby corrected as shown below:

In the Specification

Please delete Example 10 from Column 100, Line 17 – Column 106, Line 34.

Signed and Sealed this
Twenty-fifth Day of May, 2021

Drew Hirshfeld
*Performing the Functions and Duties of the*
*Under Secretary of Commerce for Intellectual Property and*
*Director of the United States Patent and Trademark Office*